US012590158B2

(12) United States Patent (10) Patent No.: US 12,590,158 B2
Yuan et al. (45) Date of Patent: Mar. 31, 2026

(54) ANTI-TRKA ANTIBODY OR ANTIGEN-BINDING FRAGMENT THEREOF, PREPARATION METHOD THEREOF, AND APPLICATION THEREOF

(71) Applicant: XIYUAN ANJIAN MEDICINE (SHANGHAI) CO., LTD, Shanghai (CN)

(72) Inventors: Xiaohui Yuan, Shanghai (CN); Guoyong Wang, Shanghai (CN); Yujiao Liu, Shanghai (CN); Donghong Zheng, Shanghai (CN)

(73) Assignee: XIYUAN ANJIAN MEDICINE (SHANGHAI) CO., LTD, Shanghai (CN)

( * ) Notice: Subject to any disclaimer, the term of this patent is extended or adjusted under 35 U.S.C. 154(b) by 585 days.

(21) Appl. No.: 18/040,042

(22) PCT Filed: Feb. 23, 2022

(86) PCT No.: PCT/CN2022/077414
§ 371 (c)(1),
(2) Date: Jan. 31, 2023

(87) PCT Pub. No.: WO2022/179516
PCT Pub. Date: Sep. 1, 2022

(65) Prior Publication Data
US 2023/0303703 A1 Sep. 28, 2023

(30) Foreign Application Priority Data
Feb. 28, 2021 (CN) .......................... 202110222357.4

(51) Int. Cl.
*C07K 16/28* (2006.01)
*A61K 39/00* (2006.01)
*A61P 25/04* (2006.01)

(52) U.S. Cl.
CPC .......... *C07K 16/2863* (2013.01); *A61K 39/00* (2013.01); *A61P 25/04* (2018.01); *A61K 2039/505* (2013.01); *C07K 2317/20* (2013.01);

*C07K 2317/24* (2013.01); *C07K 2317/565* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | | |
|---|---|---|---|---|
| 10,618,974 B2 * | 4/2020 | Beidler | .................. | A61P 29/02 |
| 2017/0218087 A1 | 8/2017 | Blein et al. | | |
| 2017/0362327 A1 | 12/2017 | Walmsley et al. | | |

FOREIGN PATENT DOCUMENTS

| | | | |
|---|---|---|---|
| CN | 112010978 A | | 12/2020 |
| CN | 112961244 A | * | 6/2021 |
| CN | 117264068 A | * | 12/2023 |
| KR | 101782857 B1 | | 9/2017 |
| WO | 2020/238998 A1 | | 12/2020 |

OTHER PUBLICATIONS

International Search Report issued in International Patent Application No. PCT/CN2022/077414; mailed Apr. 15, 2022; 9 pgs.
Written Opinion issued in International Patent Application No. PCT/CN2022/077414; mailed Apr. 15, 2022; 9 pgs.
First Office Action issued in Chinese Patent Application No. 202110222357.4; May 11, 2022; mailed 14 pgs.

* cited by examiner

*Primary Examiner* — Marianne P Allen
(74) *Attorney, Agent, or Firm* — HAUPTMAN HAM, LLP

(57) ABSTRACT

The present invention provides an anti-TrkA antibody or an antigen-binding fragment thereof, a preparation method, and an application thereof. The present invention also provides an isolated polynucleotide encoding the anti-TrkA antibody or the antigen-binding fragments thereof, and a vector comprising the isolated polynucleotide. The present invention also provides a use of the antibody or the antigen-binding fragment thereof in the preparation of a drug for treating pain.

5 Claims, 10 Drawing Sheets

Specification includes a Sequence Listing.

Pain threshold 24h post dosing

Pain threshold 48h post dosing

ANTI-TRKA ANTIBODY OR ANTIGEN-BINDING FRAGMENT THEREOF, PREPARATION METHOD THEREOF, AND APPLICATION THEREOF

RELATED APPLICATIONS

The present application is a U.S. National Phase of International Application Number PCT/CN2022/077414, filed Feb. 23, 2022, and claims priority to Chinese Application Number 202110222357.4, filed Feb. 28, 2021.

INCORPORATION BY REFERENCE

The sequence listing provided in the file entitled S220019_IPUS_Sequence_Listing_Rev1.txt, which is an ASCII text file that was created on Jan. 5, 2023, and which comprises 52,809 bytes, is hereby incorporated by reference in its entirety.

FIELD OF THE INVENTION

The present invention belongs to the technical field of biological immunity, and in particular relates to anti-TrkA antibodies or antigen-binding fragments thereof capable of specifically binding to human Tropomyosin Receptor Kinase A. The present invention also relates to preparation methods and uses of the antibodies or antigen-binding fragments thereof.

BACKGROUND OF THE INVENTION

Tropomyosin Receptor Kinase (TrkA, also known as high affinity nerve growth factor receptor, neurotrophic tyrosine kinase receptor type 1, or TRK1-transforming tyrosine kinase protein) is a member of Tropomyosin Receptor Kinase (Trk) family, which is encoded by NTRK1 (Neurotrophic Receptor Tyrosine Kinase 1) gene. The Trk family includes three receptors, namely TrkA, TrkB and TrkC, each exerting different biological roles by binding to specific neurotrophin ligands. Trk receptors are transmembrane receptors, consisting of an extracellular region containing a ligand-binding domain, a transmembrane domain (TM), and an intracellular domain containing a tyrosine kinase domain. TrkA is predominantly expressed in neural crest neurons, sympathetic neurons, and cholinergic neurons within the basal forebrain and striatum (Holtzman D M et al. (1992) Neuron 9(3): 465-78; Verge V M et al. (1992) J. Neurosci. 12 (10): 4011-22), and it is also expressed in some non-neuronal tissues and cells including B lymphocytes (Torcia M et al. (1996) Cell 85(3): 345-56). TrkA selectively binds to Nerve Growth Factor (NGF) and is a high-affinity receptor for NGF. NGF binding to TrkA activates TrkA kinase activity, resulting in activation of multiple signaling pathways, including Ras/MAPK, PI3K/Akt, and PLCγ pathway. In addition to TrkA, NGF also binds to the p75 common neurotrophin receptor (p75 neurotrophin receptor, p75NTR, also known as the "low-affinity" NGF receptor).

The NGF/TrkA signaling pathway is involved in cell differentiation, proliferation, survival and pain. Among them, NGF/TrkA is related to the occurrence of pain and peripheral nociceptive sensitization. The activation of NGF/TrkA pathway can increase the phosphorylation of Transient Receptor Potential Vanilloid subtype 1 (TRPV1), thereby making it sensitive. Further, NGF/TrkA can increase the expression of multiple proteins, including TRPV1, Na/Ca/K ion channels, CGRP, substance P, and Brain-Derived Neurotrophic Factor (BDNF), etc., these proteins subsequently sensitize nociceptive neurons, increase nociception signals, which are transmitted from the dorsal root ganglia to the center to promote the activation of secondary neurons in the central nervous system (Denk F et al. (2017) Annu. Rev. Neurosci. 40: 307-325). In the injured and inflammatory tissues, NGF is highly expressed, and the activation of nociceptive neurons by TrkA is triggered by multiple mechanisms, resulting in pain signals. Association between the NGF/TrkA signaling pathway and pain has been demonstrated in animal models: after injected with NGF, thermal stimulus-induced paw withdrawal latency in rats was significantly shortened (Lewin et al. (1994) Eur J Neurosci, 6: 1903-1912); while the pain was suppressed by blocking the NGF/TrkA signal by administering the rats anti-NGF antibodies, TrkA-IgG, small molecule TrkA inhibitors, etc. (Woolf C J et al. (1994) Neuroscience 62: 327-331; McMahon S B et al. (1995) Net. Med. 1: 774-780; Koltzenburg M et al. (1999) Eur. J. Neurosci. 11: 1698-1704; Bagal S K et al. (2019) J Med Chem. 62(1): 247-265). In humans, NGF levels were elevated in patients with pain such as rheumatoid arthritis, interstitial cystitis, pancreatitis, prostatitis, diabetic neuropathy, and cancer pain (Aloe et al. (1992) Arthritis and Rheumatism 35: 351-355; Mantyh P W et al. (2011) Anesthesiology 115(1): 189-204). After injected with NGF, healthy persons would suffer from hyperalgesia and local pain (Petty et al. (1994) Ann Neurol. 36: 244-246), suggesting that the increased level of NGF is required for hyperalgesia. Homozygous missense mutations occurring in the NGF R gene can cause HSANS symptoms in humans, such patients were insensitive to pain, cold, and heat (Larsson et al. (2009) Neurobiol Dis, 33: 221-228). A genetic study on patients with Congenital Insensitivity to Pain with Anhidrosis (CIPA) shows that mutations within the extracellular or intracellular domain of TrkA gene (NTRK1) can cause CIPA, in such patients TrkA can not be activated by NGF, resulting in loss of pain perception in the patients (Mardy S et al. (2001) Human mutation 18: 462-471).

Globally, tens of millions of patients are suffering from chronic pain, and this number continues to increase as the population increases. Currently, agents clinically used for the treatment of chronic pain include non-steroidal anti-inflammatory agents, anticonvulsants, opioids, etc. However, these agents have many disadvantages. Among them, the non-steroidal anti-inflammatory agents have limited efficacy, and have side effects including gastrointestinal bleeding and kidney toxicity; while opioids have side effects such as addiction. Only less than 30% of chronic pain patients benefit from existing treatments (Kalso E et al. (2004) Pain 112(3): 372-80). There is an urgent need for non-toxic and abuse-free non-opioid analgesics that can relieve pain in the field. As a new analgesic mechanism, NGF/TrkA provides a possibility to solve this problem. So far, several anti-human NGF antibodies are in the R&D or clinical development stage. Clinical trials have shown that NGF antibodies have a strong and wide-ranging analgesic effect on joint pain associated with degenerative joint disease, on chronic low back pain, and on bladder pain associated with interstitial cystitis (Lane N E et al. (2010) N Engl J Med 363: 1521-1531. On the other hand, clinical trials of multiple NGF antibodies have also shown that NGF antibodies increase the risk of accelerated progression of osteoarthritis in patients (Thomas J S et al. (2019) JAMA 322: 37-48), and these NGF antibodies may face problems such as being restricted to severely ill people, not for a long-term use, and dose limitations, making the clinical application of NGF antibodies need further safety verification.

TrkA-targeting antibodies are theoretically better options for treatment than NGF inhibitors, since TrkA antibodies do not affect the binding of NGF to p75 receptor, the function of which is related to neuron development, osteoblast differentiation, proliferation, myoblast differentiation, muscle repair, etc. (Akiyama Y et al. (2014) Differentiation, 87: 111-118; Deponti et al. (2009) Molecular Biology of the Cell, 20: 3620-3627; Mikami et al. (2012) Differentiation, 84: 392-399). TrkA antibodies have superior performance in terms of safety.

Based on this, there is currently a need for TrkA antibodies with higher affinity and stronger specificity.

SUMMARY OF THE INVENTION

Based on the deficiency of the prior art, the main purpose of the present invention is to provide an anti-TrkA antibody with higher affinity and stronger specificity. The invention also provides methods for preparing the antibodies and uses thereof. The anti-TrkA antibodies of the invention are useful for the treatment of pain, including inflammatory pain, postoperative pain, neuropathic pain, cancer pain, osteoarthritis, etc. Compared with the prior art, the anti-TrkA antibodies or antigen binding fragments thereof developed in the invention have higher affinities, better specificities and stronger activities.

In one aspect, the present invention provides an antibody or antigen-binding fragment thereof capable of specifically binding to TrkA, the antibody or antigen-binding fragment thereof comprising:

(a) a heavy chain variable region (VH) comprising the following three complementarity determining regions (CDRs):

(i) VH CDR1 consisting of the following sequence: SEQ ID NO:1, or a sequence having one or more amino acid substitutions, deletions or additions (e.g. 1, 2 or 3 amino acid substitutions, deletions or additions) compared to the same, (ii) VH CDR2 consisting of the following sequence: SEQ ID NO:2, or a sequence having one or more amino acid substitutions, deletions or additions (e.g. 1, 2 or 3 amino acid substitutions, deletions or additions) compared to the same, and (iii) VH CDR3 consisting of the following sequence: SEQ ID NO:3, or a sequence having one or more amino acid substitutions, deletions or additions (e.g. 1, 2 or 3 amino acid substitutions, deletions or additions) compared to the same, and/or (b) a light chain variable region (VL) comprising the following three complementarity determining regions (CDRs):

(iv) VL CDR1 consisting of the following sequence: SEQ ID NO:25, or a sequence having one or more amino acid substitutions, deletions or additions (e.g. 1, 2 or 3 amino acid substitutions, deletions or additions) compared to the same, (v) VL CDR2 consisting of the following sequence: SEQ ID NO:26, or a sequence having one or more amino acid substitutions, deletions or additions (e.g. 1, 2 or 3 amino acid substitutions, deletions or additions) compared to the same, and (vi) VL CDR3 consisting of the following sequence: SEQ ID NO:27, or a sequence having one or more amino acid substitutions, deletions or additions (e.g. 1, 2 or 3 amino acid substitutions, deletions or additions) compared to the same;

preferably, the substitution(s) described in any one from (i) to (vi) is (are) conservative substitution(s);

preferably, the VH of the antibody or antigen-binding fragment thereof comprises: VH CDR1 as shown in SEQ ID NO: 1, VH CDR2 as shown in SEQ ID NO: 2, and VH CDR3 as shown in SEQ ID NO: 3; and the VL of the antibody or antigen-binding fragment thereof comprises: VL CDR1 as shown in SEQ ID NO: 25, VL CDR2 as shown in SEQ ID NO: 26, and VL CDR3 as shown in SEQ ID NO: 27.

In one aspect, the present invention provides an anti-TrkA antibody or antigen-binding fragment thereof capable of specifically binding to TrkA, the antibody or antigen-binding fragment thereof comprising:

(a) a heavy chain variable region (VH) comprising the following three complementarity determining regions (CDRs):

(i) VH CDR1 consisting of the following sequence: SEQ ID NO:4, or a sequence having one or more amino acid substitutions, deletions or additions (e.g. 1, 2 or 3 amino acid substitutions, deletions or additions) compared to the same, (ii) VH CDR2 consisting of the following sequence: SEQ ID NO:5, or a sequence having one or more amino acid substitutions, deletions or additions (e.g. 1, 2 or 3 amino acid substitutions, deletions or additions) compared to the same, and (iii) VH CDR3 consisting of the following sequence: SEQ ID NO:6, or a sequence having one or more amino acid substitutions, deletions or additions (e.g. 1, 2 or 3 amino acid substitutions, deletions or additions) compared to the same;

and/or (b) a light chain variable region (VL) comprising the following three complementarity determining regions (CDRs):

(iv) VL CDR1 consisting of the following sequence: SEQ ID NO:28, or a sequence having one or more amino acid substitutions, deletions or additions (e.g. 1, 2 or 3 amino acid substitutions, deletions or additions) compared to the same, (v) VL CDR2 consisting of the following sequence: SEQ ID NO:29, or a sequence having one or more amino acid substitutions, deletions or additions (e.g. 1, 2 or 3 amino acid substitutions, deletions or additions) compared to the same, and (vi) VL CDR3 consisting of the following sequence: SEQ ID NO:30, or a sequence having one or more amino acid substitutions, deletions or additions (e.g. 1, 2 or 3 amino acid substitutions, deletions or additions) compared to the same;

preferably, the substitution(s) described in any one from (i) to (vi) is (are) conservative substitution(s);

preferably, the VH of the antibody or antigen-binding fragment thereof comprises: VH CDR1 as shown in SEQ ID NO: 4, VH CDR2 as shown in SEQ ID NO: 5, and VH CDR3 as shown in SEQ ID NO: 6; and the VL of the antibody or antigen-binding fragment thereof comprises: VL CDR1 as shown in SEQ ID NO: 28, VL CDR2 as shown in SEQ ID NO: 29, and VL CDR3 as shown in SEQ ID NO: 30.

In one aspect, the present invention provides an antibody or antigen-binding fragment thereof capable of specifically binding to TrkA, the antibody or antigen-binding fragment thereof comprising:

(a) a heavy chain variable region (VH) comprising the following three complementarity determining regions (CDRs):

(i) VH CDR1 consisting of the following sequence: SEQ ID NO:7, or a sequence having one or more amino acid substitutions, deletions or additions (e.g. 1, 2 or 3 amino acid substitutions, deletions or additions) compared to the same, (ii) VH CDR2 consisting of the following sequence: SEQ ID NO:8, or a sequence having one or more amino acid substitutions, deletions or additions (e.g. 1, 2 or 3 amino acid substitutions, deletions or additions) compared to the same, and (iii) VH CDR3 consisting of the following sequence: SEQ ID NO:9, or a sequence having one or more amino acid substitutions, deletions or additions (e.g. 1, 2 or 3 amino acid substitutions, deletions or additions) compared to the same;

and/or (b) a light chain variable region (VL) comprising the following three complementarity determining regions (CDRs):

(iv) VL CDR1 consisting of the following sequence: SEQ ID NO:31, or a sequence having one or more amino acid substitutions, deletions or additions (e.g. 1, 2 or 3 amino acid substitutions, deletions or additions) compared to the same, (v) VL CDR2 consisting of the following sequence: SEQ ID NO:32, or a sequence having one or more amino acid substitutions, deletions or additions (e.g. 1, 2 or 3 amino acid substitutions, deletions or additions) compared to the same, and (vi) VL CDR3 consisting of the following sequence: SEQ ID NO:33, or a sequence having one or more amino acid substitutions, deletions or additions (e.g. 1, 2 or 3 amino acid substitutions, deletions or additions) compared to the same;

preferably, the substitution(s) described in any one from (i) to (vi) is (are) conservative substitution(s);

preferably, the VH of the antibody or antigen-binding fragment thereof comprises: VH CDR1 as shown in SEQ ID NO: 7, VH CDR2 as shown in SEQ ID NO: 8, and VH CDR3 as shown in SEQ ID NO: 9; and the VL of the antibody or antigen-binding fragment thereof comprises: VL CDR1 as shown in SEQ ID NO: 31, VL CDR2 as shown in SEQ ID NO: 32, and VL CDR3 as shown in SEQ ID NO: 33.

In one aspect, the present invention provides an antibody or antigen-binding fragment thereof capable of specifically binding to TrkA, the antibody or antigen-binding fragment thereof comprising:

(a) a heavy chain variable region (VH) comprising the following three complementarity determining regions (CDRs):

(i) VH CDR1 consisting of the following sequence: SEQ ID NO:10, or a sequence having one or more amino acid substitutions, deletions or additions (e.g. 1, 2 or 3 amino acid substitutions, deletions or additions) compared to the same, (ii) VH CDR2 consisting of the following sequence: SEQ ID NO:11, or a sequence having one or more amino acid substitutions, deletions or additions (e.g. 1, 2 or 3 amino acid substitutions, deletions or additions) compared to the same, and (iii) VH CDR3 consisting of the following sequence: SEQ ID NO:12, or a sequence having one or more amino acid substitutions, deletions or additions (e.g. 1, 2 or 3 amino acid substitutions, deletions or additions) compared to the same;

and/or (b) a light chain variable region (VL) comprising the following three complementarity determining regions (CDRs):

(iv) VL CDR1 consisting of the following sequence: SEQ ID NO:34, or a sequence having one or more amino acid substitutions, deletions or additions (e.g. 1, 2 or 3 amino acid substitutions, deletions or additions) compared to the same, (v) VL CDR2 consisting of the following sequence: SEQ ID NO:35, or a sequence having one or more amino acid substitutions, deletions or additions (e.g. 1, 2 or 3 amino acid substitutions, deletions or additions) compared to the same, and (vi) VL CDR3 consisting of the following sequence: SEQ ID NO:36, or a sequence having one or more amino acid substitutions, deletions or additions (e.g. 1, 2 or 3 amino acid substitutions, deletions or additions) compared to the same;

preferably, the substitution(s) described in any one from (i) to (vi) is (are) conservative substitution(s);

preferably, the VH of the antibody or antigen-binding fragment thereof comprises: VH CDR1 as shown in SEQ ID NO: 10, VH CDR2 as shown in SEQ ID NO: 11, and VH CDR3 as shown in SEQ ID NO: 12; and the VL of the antibody or antigen-binding fragment thereof comprises: VL CDR1 as shown in SEQ ID NO: 34, VL CDR2 as shown in SEQ ID NO: 35, and VL CDR3 as shown in SEQ ID NO: 36.

In one aspect, the present invention provides an antibody or antigen-binding fragment thereof capable of specifically binding to TrkA, the antibody or antigen-binding fragment thereof comprising:

(a) a heavy chain variable region (VH) comprising the following three complementarity determining regions (CDRs):

(i) VH CDR1 consisting of the following sequence: SEQ ID NO:13, or a sequence having one or more amino acid substitutions, deletions or additions (e.g. 1, 2 or 3 amino acid substitutions, deletions or additions) compared to the same, (ii) VH CDR2 consisting of the following sequence: SEQ ID NO:14, or a sequence having one or more amino acid substitutions, deletions or additions (e.g. 1, 2 or 3 amino acid substitutions, deletions or additions) compared to the same, and (iii) VH CDR3 consisting of the following sequence: SEQ ID NO:15, or a sequence having one or more amino acid substitutions, deletions or additions (e.g. 1, 2 or 3 amino acid substitutions, deletions or additions) compared to the same;

and/or (b) a light chain variable region (VL) comprising the following three complementarity determining regions (CDRs):

(iv) VL CDR1 consisting of the following sequence: SEQ ID NO: 37, or a sequence having one or more amino acid substitutions, deletions or additions (e.g. 1, 2 or 3 amino acid substitutions, deletions or additions) compared to the same, (v) VL CDR2 consisting of the following sequence: SEQ ID NO:38, or a sequence having one or more amino acid substitutions, deletions or additions (e.g. 1, 2 or 3 amino acid substitutions, deletions or additions) compared to the same, and (vi) VL CDR3 consisting of the following sequence: SEQ ID NO:39, or a sequence having one or more amino acid substitutions, deletions or additions (e.g. 1, 2 or 3 amino acid substitutions, deletions or additions) compared to the same;

preferably, the substitution(s) described in any one from (i) to (vi) is (are) conservative substitution(s);

preferably, the VH of the antibody or antigen-binding fragment thereof comprises: VH CDR1 as shown in SEQ ID NO:13, VH CDR2 as shown in SEQ ID NO:14 and VH CDR3 as shown in SEQ ID NO:15, and the VL of the antibody or antigen-binding fragment thereof comprises: VL CDR1 as shown in SEQ ID NO: 37, VL CDR2 as shown in SEQ ID NO: 38, and VL CDR3 as shown in SEQ ID NO: 39.

In one aspect, the present invention provides an antibody or antigen-binding fragment thereof capable of specifically binding to TrkA, the antibody or antigen-binding fragment thereof comprising:

(a) a heavy chain variable region (VH) comprising the following three complementarity determining regions (CDRs):

(i) VH CDR1 consisting of the following sequence: SEQ ID NO:16, or a sequence having one or more amino acid substitutions, deletions or additions (e.g. 1, 2 or 3 amino acid substitutions, deletions or additions) compared to the same, (ii) VH CDR2 consisting of the following sequence: SEQ ID NO:17, or a sequence having one or more amino acid substitutions, deletions or additions (e.g. 1, 2 or 3 amino acid substitutions, deletions or additions) compared to the same, and (iii) VH CDR3 consisting of the following sequence: SEQ ID NO:18, or a sequence having one or more amino acid substitutions, deletions or additions (e.g. 1, 2 or 3 amino acid substitutions, deletions or additions) compared to the same;

and/or (b) a light chain variable region (VL) comprising the following three complementarity determining regions (CDRs):

(iv) VL CDR1 consisting of the following sequence: SEQ ID NO:40, or a sequence having one or more amino acid substitutions, deletions or additions (e.g. 1, 2 or 3 amino acid substitutions, deletions or additions) compared to the same, (v) VL CDR2 consisting of the following sequence: SEQ ID NO:41, or a sequence having one or more amino acid substitutions, deletions or additions (e.g. 1, 2 or 3 amino acid substitutions, deletions or additions) compared to the same, and (vi) VL CDR3 consisting of the following sequence: SEQ ID NO:42, or a sequence having one or more amino acid substitutions, deletions or additions (e.g. 1, 2 or 3 amino acid substitutions, deletions or additions) compared to the same;

preferably, the substitution(s) described in any one from (i) to (vi) is (are) conservative substitution(s);

preferably, the VH of the antibody or antigen-binding fragment thereof comprises: VH CDR1 as shown in SEQ ID NO:16, VH CDR2 as shown in SEQ ID NO:17 and VH CDR3 as shown in SEQ ID NO:18, and the VL of the antibody or antigen-binding fragment thereof comprises: VL CDR1 as shown in SEQ ID NO: 40, VL CDR2 as shown in SEQ ID NO: 41, and VL CDR3 as shown in SEQ ID NO: 42.

In one aspect, the present invention provides an anti-TrkA antibody or antigen-binding fragment thereof capable of specifically binding to TrkA, the antibody or antigen-binding fragment thereof comprising:

(a) a heavy chain variable region (VH) comprising the following three complementarity determining regions (CDRs):

(i) VH CDR1 consisting of the following sequence: SEQ ID NO:19, or a sequence having one or more amino acid substitutions, deletions or additions (e.g. 1, 2 or 3 amino acid substitutions, deletions or additions) compared to the same, (ii) VH CDR2 consisting of the following sequence: SEQ ID NO:20, or a sequence having one or more amino acid substitutions, deletions or additions (e.g. 1, 2 or 3 amino acid substitutions, deletions or additions) compared to the same, and (iii) VH CDR3 consisting of the following sequence: SEQ ID NO:21, or a sequence having one or more amino acid substitutions, deletions or additions (e.g. 1, 2 or 3 amino acid substitutions, deletions or additions) compared to the same;

and/or (b) a light chain variable region (VL) comprising the following three complementarity determining regions (CDRs):

(iv) VL CDR1 consisting of the following sequence: SEQ ID NO:43, or a sequence having one or more amino acid substitutions, deletions or additions (e.g. 1, 2 or 3 amino acid substitutions, deletions or additions) compared to the same, (v) VL CDR2 consisting of the following sequence: SEQ ID NO:44, or a sequence having one or more amino acid substitutions, deletions or additions (e.g. 1, 2 or 3 amino acid substitutions, deletions or additions) compared to the same, and (vi) VL CDR3 consisting of the following sequence: SEQ ID NO:45, or a sequence having one or more amino acid substitutions, deletions or additions (e.g. 1, 2 or 3 amino acid substitutions, deletions or additions) compared to the same;

preferably, the substitution(s) described in any one from (i) to (vi) is (are) conservative substitution(s);

preferably, the VH of the antibody or antigen-binding fragment thereof comprises: VH CDR1 as shown in SEQ ID NO:19, VH CDR2 as shown in SEQ ID NO:20 and VH CDR3 as shown in SEQ ID NO:21, and the VL of the antibody or antigen-binding fragment thereof comprises: VL CDR1 as shown in SEQ ID NO: 43, VL CDR2 as shown in SEQ ID NO: 44, and VL CDR3 as shown in SEQ ID NO: 45.

In one aspect, the present invention provides an antibody or antigen-binding fragment thereof capable of specifically binding to TrkA, the antibody or antigen-binding fragment thereof comprising:

(a) a heavy chain variable region (VH) comprising the following three complementarity determining regions (CDRs):

(i) VH CDR1 consisting of the following sequence: SEQ ID NO:22, or a sequence having one or more amino acid substitutions, deletions or additions (e.g. 1, 2 or 3 amino acid substitutions, deletions or additions) compared to the same,

(ii) VH CDR2 consisting of the following sequence: SEQ ID NO:23, or a sequence having one or more amino acid substitutions, deletions or additions (e.g. 1, 2 or 3 amino acid substitutions, deletions or additions) compared to the same, and (iii) VH CDR3 consisting of the following sequence: SEQ ID NO:24, or a sequence having one or more amino acid substitutions, deletions or additions (e.g. 1, 2 or 3 amino acid substitutions, deletions or additions) compared to the same;

and/or (b) a light chain variable region (VL) comprising the following three complementarity determining regions (CDRs):

(iv) VL CDR1 consisting of the following sequence: SEQ ID NO:46, or a sequence having one or more amino acid substitutions, deletions or additions (e.g. 1, 2 or 3 amino acid substitutions, deletions or additions) compared to the same, (v) VL CDR2 consisting of the following sequence: SEQ ID NO:47, or a sequence having one or more amino acid substitutions, deletions or additions (e.g. 1, 2 or 3 amino acid substitutions, deletions or additions) compared to the same, and (vi) VL CDR3 consisting of the following sequence: SEQ ID NO:48, or a sequence having one or more amino acid substitutions, deletions or additions (e.g. 1, 2 or 3 amino acid substitutions, deletions or additions) compared to the same;

preferably, the substitution(s) described in any one from (i) to (vi) is (are) conservative substitution(s);

preferably, the VH of the antibody or antigen-binding fragment thereof comprises: VH CDR1 as shown in SEQ ID NO: 22, VH CDR2 as shown in SEQ ID NO: 23, and VH CDR3 as shown in SEQ ID NO: 24, and the VL of the antibody or antigen-binding fragment thereof comprises: VL CDR1 as shown in SEQ ID NO: 46, VL CDR2 as shown in SEQ ID NO: 47, and VL CDR3 as shown in SEQ ID NO: 48.

In one aspect, the present invention provides an antibody or antigen-binding fragment thereof capable of specifically binding to TrkA, the antibody or antigen-binding fragment thereof comprising a heavy chain variable region and a light chain variable region, wherein:

the heavy chain variable region comprises three CDRs comprised in the heavy chain variable region as shown in any one of SEQ ID NOs: 49-56; and the light chain variable region comprises three CDRs comprised in the light chain variable region as shown in any one of SEQ ID NOs: 57-64;

preferably, the three CDRs comprised in the heavy chain variable region and/or the three CDRs comprised in the light chain variable region are defined by the Kabat or IMGT numbering system.

The antibody or antigen-binding fragment thereof according to the present invention, wherein the antibody or antigen-binding fragment thereof comprises:

(a) a heavy chain variable region (VH) comprising amino acid sequence selected from:

(i) sequence as shown in SEQ ID NO: 49;

(ii) sequence having one or more amino acid substitutions, deletions or additions (e.g. 1, 2, 3, 4 or 5 amino acid substitutions, deletions or additions) compared to SEQ ID NO:49; or (iii) sequence having at least 80%, at least 85%, at least 90%, at least 91%, at least 92%, at least 93%, at least 94%, at least 95%, at least 96%, at least 97%, at least 98%, at least 99%, or 100% sequence identity to the sequence as shown in SEQ ID NO:49;

and/or, (b) a light chain variable region (VL) comprising amino acid sequence selected from:

(iv) sequence as shown in SEQ ID NO:57;

(v) sequence having one or more amino acid substitutions, deletions or additions (e.g. 1, 2, 3, 4 or 5 amino acid substitutions, deletions or additions) compared to SEQ ID NO:57; or (vi) sequence having at least 80%, at least 85%, at least 90%, at least 91%, at least 92%, at least 93%, at least 94%, at least 95%, at least 96%, at least 97%, at least 98%, at least 99%, or 100% sequence identity to the sequence as shown in SEQ ID NO:57;

preferably, the substitution(s) described in (ii) or (v) is (are) conservative substitution(s);

preferably, the antibody or antigen-binding fragment thereof comprises: VH having sequence as shown in SEQ ID NO:49 and VL having sequence as shown in SEQ ID NO:57.

The antibody or antigen-binding fragment thereof according to the present invention, wherein the antibody or antigen-binding fragment thereof comprises:

(a) a heavy chain variable region (VH) comprising amino acid sequence selected from:

(i) sequence as shown in SEQ ID NO: 50;

(ii) sequence having one or more amino acid substitutions, deletions or additions (e.g. 1, 2, 3, 4 or 5 amino acid substitutions, deletions or additions) compared to SEQ ID NO:50; or (iii) sequence having at least 80%, at least 85%, at least 90%, at least 91%, at least 92%, at least 93%, at least 94%, at least 95%, at least 96%, at least 97%, at least 98%, at least 99%, or 100% sequence identity to the sequence as shown in SEQ ID NO:50;

and/or, (b) a light chain variable region (VL) comprising amino acid sequence selected from:

(iv) sequence as shown in SEQ ID NO:58;

(v) sequence having one or more amino acid substitutions, deletions or additions (e.g. 1, 2, 3, 4 or 5 amino acid substitutions, deletions or additions) compared to SEQ ID NO:58; or (vi) sequence having at least 80%, at least 85%, at least 90%, at least 91%, at least 92%, at least 93%, at least 94%, at least 95%, at least 96%, at least 97%, at least 98%, at least 99%, or 100% sequence identity to the sequence as shown in SEQ ID NO:58;

preferably, the substitution(s) described in (ii) or (v) is (are) conservative substitution(s);

preferably, the antibody or antigen-binding fragment thereof comprises: a VH having sequence as shown in SEQ ID NO: 50 and a VL having sequence as shown in SEQ ID NO: 58.

The antibody or antigen-binding fragment thereof according to the present invention, wherein the antibody or antigen-binding fragment thereof comprises:

(a) a heavy chain variable region (VH) comprising amino acid sequence selected from:

(i) sequence as shown in SEQ ID NO: 51;

(ii) sequence having one or more amino acid substitutions, deletions or additions (e.g. 1, 2, 3, 4 or 5 amino acid substitutions, deletions or additions) compared to SEQ ID NO:51; or (iii) sequence having at least 80%, at least 85%, at least 90%, at least 91%, at least 92%, at least 93%, at least 94%, at least 95%, at least 96%, at least 97%, at least 98%, at least 99%, or 100% sequence identity to the sequence as shown in SEQ ID NO:51;

and/or, (b) a light chain variable region (VL) comprising amino acid sequence selected from:

(iv) sequence as shown in SEQ ID NO:59;

(v) sequence having one or more amino acid substitutions, deletions or additions (e.g. 1, 2, 3, 4 or 5 amino acid substitutions, deletions or additions) compared to SEQ ID NO:59; or (vi) sequence having at least 80%, at least 85%, at least 90%, at least 91%, at least 92%, at least 93%, at least 94%, at least 95%, at least 96%, at least 97%, at least 98%, at least 99%, or 100% sequence identity to the sequence as shown in SEQ ID NO:59;

preferably, the substitution(s) described in (ii) or (v) is (are) conservative substitution(s);

preferably, the antibody or antigen-binding fragment thereof comprises: a VH having sequence as shown in SEQ ID NO:51 and a VL having sequence as shown in SEQ ID NO:59.

The antibody or antigen-binding fragment thereof according to the present invention, wherein the antibody or antigen-binding fragment thereof comprises:

(a) a heavy chain variable region (VH) comprising amino acid sequence selected from:

(i) sequence as shown in SEQ ID NO: 52;

(ii) sequence having one or more amino acid substitutions, deletions or additions (e.g. 1, 2, 3, 4 or 5 amino acid substitutions, deletions or additions) compared to SEQ ID NO:52; or (iii) sequence having at least 80%, at least 85%, at least 90%, at least 91%, at least 92%, at least 93%, at least 94%, at least 95%, at least 96%, at least 97%, at least 98%, at least 99%, or 100% sequence identity to the sequence as shown in SEQ ID NO:52;

and/or, (b) a light chain variable region (VL) comprising amino acid sequence selected from:

(iv) sequence as shown in SEQ ID NO:60;

(v) sequence having one or more amino acid substitutions, deletions or additions (e.g. 1, 2, 3, 4 or 5 amino acid substitutions, deletions or additions) compared to SEQ ID NO:60; or (vi) sequence having at least 80%, at least 85%, at least 90%, at least 91%, at least 92%, at least 93%, at least 94%, at least 95%, at least 96%, at least 97%, at least 98%, at least 99%, or 100% sequence identity to the sequence as shown in SEQ ID NO:60;

preferably, the substitution(s) described in (ii) or (v) is (are) conservative substitution(s);

preferably, the antibody or antigen-binding fragment thereof comprises: a VH having sequence as shown in SEQ ID NO: 52 and a VL having sequence as shown in SEQ ID NO: 60.

The antibody or antigen-binding fragment thereof according to the present invention, wherein the antibody or antigen-binding fragment thereof comprises:

(a) a heavy chain variable region (VH) comprising amino acid sequence selected from:

(i) sequence as shown in SEQ ID NO: 53;

(ii) sequence having one or more amino acid substitutions, deletions or additions (e.g. 1, 2, 3, 4 or 5 amino acid substitutions, deletions or additions) compared to SEQ ID NO:53; or (iii) sequence having at least 80%, at least 85%, at least 90%, at least 91%, at least 92%, at least 93%, at least 94%, at least 95%, at least 96%, at least 97%, at least 98%, at least 99%, or 100% sequence identity to the sequence as shown in SEQ ID NO:53;

and/or, (b) a light chain variable region (VL) comprising amino acid sequence selected from:

(iv) sequence as shown in SEQ ID NO:61;

(v) sequence having one or more amino acid substitutions, deletions or additions (e.g. 1, 2, 3, 4 or 5 amino acid substitutions, deletions or additions) compared to SEQ ID NO:61; or (vi) sequence having at least 80%, at least 85%, at least 90%, at least 91%, at least 92%, at least 93%, at least 94%, at least 95%, at least 96%, at least 97%, at least 98%, at least 99%, or 100% sequence identity to the sequence as shown in SEQ ID NO:61;

preferably, the substitution(s) described in (ii) or (v) is (are) conservative substitution(s);

preferably, the antibody or antigen-binding fragment thereof comprises: a VH having sequence as shown in SEQ ID NO: 53 and a VL having sequence as shown in SEQ ID NO: 61.

The antibody or antigen-binding fragment thereof according to the present invention, wherein the antibody or antigen-binding fragment thereof comprises:

(a) a heavy chain variable region (VH) comprising amino acid sequence selected from:

(i) sequence as shown in SEQ ID NO: 54;

(ii) sequence having one or more amino acid substitutions, deletions or additions (e.g. 1, 2, 3, 4 or 5 amino acid substitutions, deletions or additions) compared to SEQ ID NO:54; or (iii) sequence having at least 80%, at least 85%, at least 90%, at least 91%, at least 92%, at least 93%, at least 94%, at least 95%, at least 96%, at least 97%, at least 98%, at least 99%, or 100% sequence identity to the sequence as shown in SEQ ID NO:54;

and/or, (b) a light chain variable region (VL) comprising amino acid sequence selected from:

(iv) sequence as shown in SEQ ID NO:62;

(v) sequence having one or more amino acid substitutions, deletions or additions (e.g. 1, 2, 3, 4 or 5 amino acid substitutions, deletions or additions) compared to SEQ ID NO:62; or (vi) sequence having at least 80%, at least 85%, at least 90%, at least 91%, at least 92%, at least 93%, at least 94%, at least 95%, at least 96%, at least 97%, at least 98%, at least 99%, or 100% sequence identity to the sequence as shown in SEQ ID NO:62;

preferably, the substitution(s) described in (ii) or (v) is (are) conservative substitution(s);

preferably, the antibody or antigen-binding fragment thereof comprises: a VH having sequence as shown in SEQ ID NO: 54 and a VL having sequence as shown in SEQ ID NO: 62.

The antibody or antigen-binding fragment thereof according to the present invention, wherein the antibody or antigen-binding fragment thereof comprises:

(a) a heavy chain variable region (VH) comprising amino acid sequence selected from:

(i) sequence as shown in SEQ ID NO: 55;

(ii) sequence having one or more amino acid substitutions, deletions or additions (e.g. 1, 2, 3, 4 or 5 amino acid substitutions, deletions or additions) compared to SEQ ID NO:55; or (iii) sequence having at least 80%, at least 85%, at least 90%, at least 91%, at least 92%, at least 93%, at least 94%, at least 95%, at least 96%, at least 97%, at least 98%, at least 99%, or 100% sequence identity to the sequence as shown in SEQ ID NO:55;

and/or, (b) a light chain variable region (VL) comprising amino acid sequence selected from:

(iv) sequence as shown in SEQ ID NO:63;

(v) sequence having one or more amino acid substitutions, deletions or additions (e.g. 1, 2, 3, 4 or 5 amino acid substitutions, deletions or additions) compared to SEQ ID NO:63; or (vi) sequence having at least 80%, at least 85%, at least 90%, at least 91%, at least 92%, at least 93%, at least 94%, at least 95%, at least 96%, at least 97%, at least 98%, at least 99%, or 100% sequence identity to the sequence as shown in SEQ ID NO:63;

preferably, the substitution(s) described in (ii) or (v) is (are) conservative substitution(s);

preferably, the antibody or antigen-binding fragment thereof comprises: a VH having sequence as shown in SEQ ID NO: 55 and a VL having sequence as shown in SEQ ID NO: 63.

The antibody or antigen-binding fragment thereof according to the present invention, wherein the antibody or antigen-binding fragment thereof comprises:

(a) a heavy chain variable region (VH) comprising amino acid sequence selected from:

(i) sequence as shown in SEQ ID NO: 56;

(ii) sequence having one or more amino acid substitutions, deletions or additions (e.g. 1, 2, 3, 4 or 5 amino acid substitutions, deletions or additions) compared to SEQ ID NO:56; or (iii) sequence having at least 80%, at least 85%, at least 90%, at least 91%, at least 92%, at least 93%, at least 94%, at least 95%, at least 96%, at least 97%, at least 98%, at least 99%, or 100% sequence identity to the sequence as shown in SEQ ID NO:56;

and/or, (b) a light chain variable region (VL) comprising amino acid sequence selected from:

(iv) sequence as shown in SEQ ID NO:64;

(v) sequence having one or more amino acid substitutions, deletions or additions (e.g. 1, 2, 3, 4 or 5 amino acid substitutions, deletions or additions) compared to SEQ ID NO:64; or (vi) sequence having at least 80%, at least 85%, at least 90%, at least 91%, at least 92%, at least 93%, at least 94%, at least 95%, at least 96%, at least 97%, at least 98%, at least 99%, or 100% sequence identity to the sequence as shown in SEQ ID NO:64;

preferably, the substitution(s) described in (ii) or (v) is (are) conservative substitution(s);

preferably, the antibody or antigen-binding fragment thereof comprises: a VH having sequence as shown in SEQ ID NO: 56 and a VL having sequence as shown in SEQ ID NO: 64.

The antibody or antigen-binding fragment thereof according to the present invention, wherein the antibody or antigen-binding fragment thereof further comprises:

(a) a heavy chain constant region (CH) of human immunoglobulin or a variant thereof, the variant having one or more amino acid substitutions, deletions or additions (e.g., up to 20, up to 15, up to 10, or up to 5 amino acid substitutions, deletions or additions; e.g., 1, 2, 3, 4 or 5 amino acid substitutions, deletions or additions) compared to the sequence from which it is derived; and (b) a light chain constant region (CL) of human immunoglobulin or a variant thereof, the variant having up to 20 conservative amino acid substitutions (e.g. up to 15, up to 10, or up to 5 amino acid conservative substitutions; e.g. 1, 2, 3, 4 or 5 conservative amino acid substitutions) compared to the sequence from which it is derived;

preferably, the heavy chain constant region is IgG heavy chain constant region, such as IgG1, IgG2, IgG3 or IgG4 heavy chain constant region;

preferably, the light chain constant region is kappa light chain constant region.

The antibody or antigen-binding fragment thereof according to the present invention, wherein the antigen-binding fragment is selected from Fab, Fab', (Fab')₂, Fv, disulfide-linked Fv, scFv, diabody and single domain antibody (sdAb); and/or, the antibody is a murine antibody, chimeric antibody, humanized antibody, bispecific antibody or multispecific antibody.

The antibody or antigen-binding fragment thereof according to the present invention, wherein the humanized antibody comprises:

(a) a heavy chain variable region (VH) comprising amino acid sequence selected from:

(i) sequence as shown in any one of SEQ ID NOs: 81, 85, 89, 97, 99 and 101;

(ii) sequence having one or more amino acid substitutions, deletions or additions (e.g. 1, 2, 3, 4 or 5 amino acid substitutions, deletions or additions) compared to the sequence as shown in any one of SEQ ID NOs: 81, 85, 89, 97, 99 and 101; or (iii) sequence having at least 80%, at least 85%, at least 90%, at least 91%, at least 92%, at least 93%, at least 94%, at least 95%, at least 96%, at least 97%, at least 98%, at least 99%, or 100% sequence identity to the sequence as shown in any one of SEQ ID NOs: 81, 85, 89, 97, 99 and 101;

and/or, (b) a light chain variable region (VL) comprising amino acid sequence selected from:

(iv) sequence as shown in any one of SEQ ID NOs: 83, 87, 91, 93 and 95;

(v) sequence having one or more amino acid substitutions, deletions or additions (e.g. 1, 2, 3, 4 or 5 amino acid substitutions, deletions or additions) compared to the sequence as shown in any one of SEQ ID NOs: 83, 87, 91, 93 and 95; or (vi) sequence having at least 80%, at least 85%, at least 90%, at least 91%, at least 92%, at least 93%, at least 94%, at least 95%, at least 96%, at least 97%, at least 98%, at least 99%, or 100% sequence identity to the sequence as shown in any one of SEQ ID NOs: 83, 87, 91, 93 and 95;

preferably, the substitution(s) described in (ii) or (v) is (are) conservative substitution(s);

preferably, the antibody or antigen-binding fragment thereof comprises: a VH having sequence as shown in any one of SEQ ID NOs: 81, 85, 89, 97, 99 and 101, and a VL having sequence as shown in any one of SEQ ID NOs: 83, 87, 91, 93 and 95.

More preferably, the humanized antibody is selected from 42F5-01, 42F5-03, 42F5-04, 42F5-05, 42F5-08, 42F5-11, 42F5-13, 42F5-14 or 42F5-15.

The antibody or antigen-binding fragment thereof according to the present invention, wherein the antibody or antigen-binding fragment thereof is labeled; preferably, the antibody or antigen-binding fragment thereof is labeled with a detectable marker, such as enzyme (e.g. horseradish peroxidase), radioisotope, fluorescent dye, luminescent substance (such as chemiluminescent substance), or biotin.

In another aspect, the present invention provides an isolated nucleic acid molecule encoding the antibody or antigen-binding fragment thereof, or the heavy chain variable region and/or light chain variable region thereof;
preferably, the polynucleotide comprises nucleotide coding sequence as shown in any one of SEQ ID NOs: 65-80, 82, 84, 86, 88, 90, 92, 94, 96, 98, 100 and 102.

The present invention also provides a vector comprising the isolated nucleic acid molecule; preferably, the vector is a cloning vector or an expression vector.

The present invention also provides a host cell comprising the isolated nucleic acid molecule or the vector.

The present invention also provides a method for preparing the antibody or antigen-binding fragment thereof, comprising culturing the host cell under conditions that allow the expression of the antibody or antigen-binding fragment thereof, and recovering the antibody or antigen-binding fragment thereof from the cultured host cell culture;
preferably, the host cell is a mammalian cell, more preferably a human, murine, sheep, horse, dog or cat cell, further preferably a Chinese hamster ovary cell.

The present invention also provides a bispecific or multispecific molecule comprising the antibody or antigen-binding fragment thereof;
preferably, the bispecific or multispecific molecule specifically binds to TrkA, and additionally specifically binds to one or more other targets;
preferably, the bispecific or multispecific molecule at least further comprises a second specifically binding molecule (e.g., a second antibody) for a second target.

The present invention also provides a pharmaceutical composition, comprising the antibody or antigen-binding fragment thereof, bispecific or multispecific molecule, and a pharmaceutically acceptable carrier and/or excipient. The present invention further provides the use of the antibody or antigen-binding fragment thereof, or the bispecific or multispecific molecule, or the pharmaceutical composition or the host cell in the preparation of a medicament for the treatment of various conditions or diseases.

The present invention also provides a method for treating various conditions or diseases, including administering to a subject in need (suitably a mammalian subject, particularly a human subject) a therapeutically effective amount of the antibody or antigen-binding fragment thereof, or the bispecific or multispecific molecule, or the pharmaceutical composition or the host cell. The condition or disease is pain, preferably chronic pain or acute pain, more preferably chronic pain; further the pain may be associated with any of the following: inflammatory pain, postoperative pain, neuropathic pain, cancer pain, etc.; more preferably, the pain may be associated with any of the following: pain in pancreatitis, pain in nephrolithiasis, pain in endometriosis, pain in IBD, pain in postoperative adhesion, pain in gallstone, headache, dysmenorrhea, musculoskeletal pain, pain in sprain, visceral pain, pain in ovarian cyst, pain in prostatitis, pain in cystitis, pain in interstitial cystitis, postoperative pain, migraine, trigeminal neuralgia, burn and/or wound pain, trauma-related pain, neuropathic pain, pain associated with musculoskeletal disease, pain in rheumatoid arthritis, pain in osteoarthritis, pain in ankylosing spondylitis, peri-articular pathological pain, tumor pain, pain due to bone metastases, pain in HIV infection. The condition or disease is neuroma or neuronal disorder. The antibodies provided by the present invention for use as medicaments have stronger binding ability and specificity compared with the existing antibodies.

DESCRIPTION OF THE DRAWINGS

Hereinafter, the embodiments of the present invention will be described in detail with reference to the accompanying drawings, wherein.

DETAILED DESCRIPTION OF THE INVENTION

Example 1: Preparation of Murine Anti-TrkA Antibodies

As an immunogen, recombinant human TrkA protein containing murine Fc tag (Beijing ACROBiosystems Co., Ltd. TRA-H5254) was mixed and emulsified with an equal volume of Freund's complete adjuvant (Sigma-Alderich, F5881) for initial immunization. Ten of each of 6-week-old BALB/c and C57 mice (Jiangsu Huafukang) were prepared, and each animal was injected subcutaneously with 50 µg Immunogen (excluding the weight of the adjuvant, similarly hereafter). The immunogen was mixed and emulsified with incomplete Freund's adjuvant (Sigma-Alderich, F5506) for subsequent booster immunizations. Two weeks after the initial immunization, each animal was injected intraperitoneally with 25 µg immunogen for the first booster immunization; 2 weeks later, each animal was injected subcutaneously with 25 µg immunogen for the second booster immunization. 4-5 weeks later, 25 µg immunogen was injected intraperitoneally for the last immunization shock.

Mouse B cells were separated after the last immunization, mixed with SP2/0 cells (Cell Bank of Chinese Academy of Sciences, TCM18), and fused according to the operation manual available from Electroporator, BTX. The fusion cells were cultured, and then screened for hybridoma cells capable of binding to TrkA and of inhibiting human TrkA to bind to ligand NGF by Enzyme Linked Immunosorbent Assay (ELISA). Subcloning was performed by limiting dilution method, and eight positive hybridoma monoclonal cell lines were obtained by screening with the same ELISA method, named 5A3, 11G8, 26E9, 33H5, 40D6, 42F5, 42H6 and 42A11 respectively.

The hybridoma monoclonal cell lines were expanded and cultured with serum-free medium, and the medium was pooled and purified by protein G column to obtain murine anti-human TrkA monoclonal antibodies 5A3, 11G8, 26E9, 33H5, 40D6, 42F5, 42H6 and 42A11.

Example 2: ELISA Detection of the Binding of Murine Anti-TrkA Antibodies to Human TrkA The binding abilities of the anti-TrkA antibodies were detected by using a TrkA extracellular region (33-417) protein comprising human Fc (Beijing ACROBiosystems Co., Ltd., TRA-H5259). Each well of a 96-well microtiter plate was coated with 50 ng of human TrkA, washed and blocked, and then added with serially diluted antibodies, and incubated at room temperature for 1 hour. After washing three times, horseradish peroxidase-conjugated goat anti-mouse Fc antibody (Biolegend, 405306) was added and incubated at room temperature for 1 hour. After washing three time, tetramethylbenzidine (TMB, Biolegend, 421101) was added for color development. 1M HCl was used to terminate the color development, and the absorbance values were read at 450 nm with a microplate reader.

Figure 1:
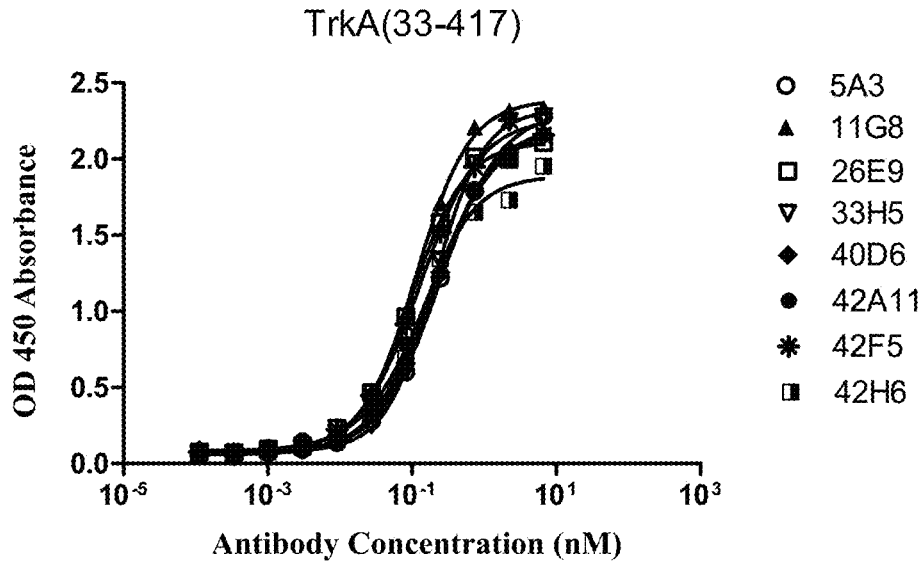
FIG. 1 shows the ELISA results of the binding of the anti-TrkA antibodies of the present invention to human TrkA protein.

All of the anti-TrkA antibodies secreted by the eight hybridomas bound to human TrkA extracellular region in a dose-dependent manner (FIG. 1), and the EC50 values of the eight antibodies binding to human TrkA are shown in Table 1.

Figure 2:
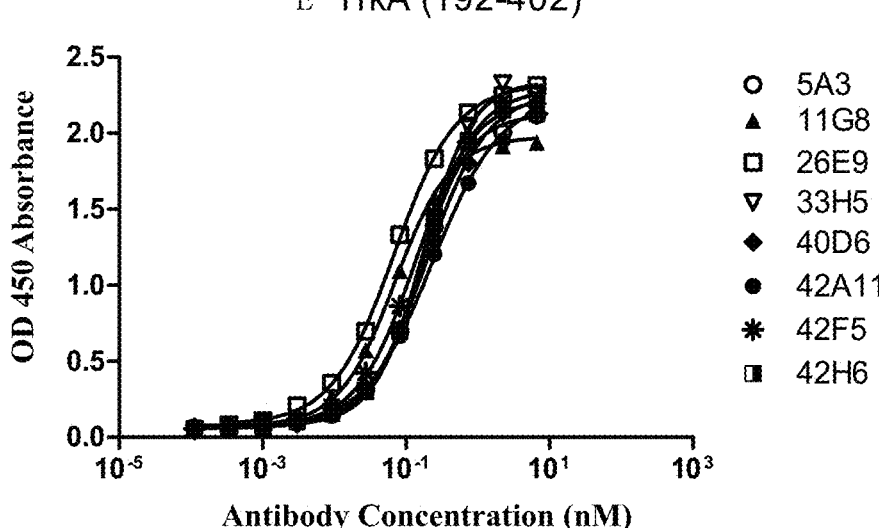
FIG. 2 shows the ELISA results of the binding of the anti-TrkA antibodies of the present invention to the extracellular region of TrkA protein (192-402).

Next, the binding abilities of the anti-TrkA antibodies were detected with a fusion protein (fused to human Fc) containing only the portion of human TrkA extracellular region that binds to the ligand NGF (TrkA 192-402) (Beijing ACROBiosystems Co., Ltd., TRA-H5258). ELISA results show that the anti-TrkA antibodies bind to the amino acid region 192-402 of the TrkA extracellular region, as shown in FIG. 2, and the EC50 is shown in Table 2.

Figure 3:
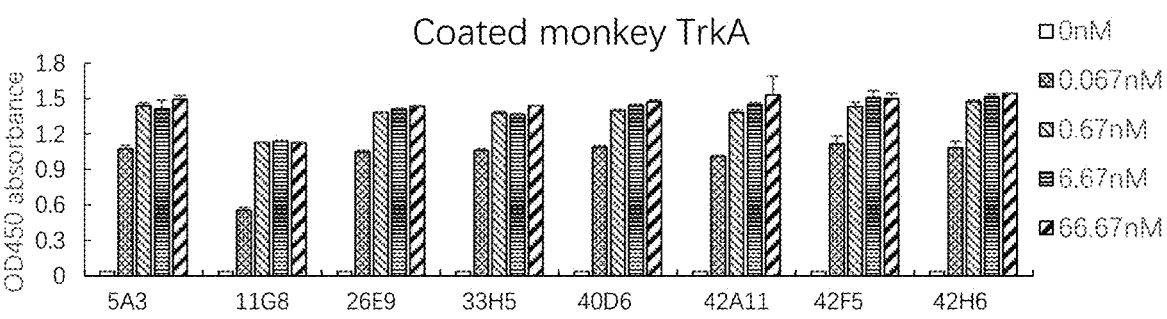
FIG. 3 shows the ELISA results of the binding of the anti-TrkA antibodies of the present invention to monkey TrkA protein.
Figure 4:
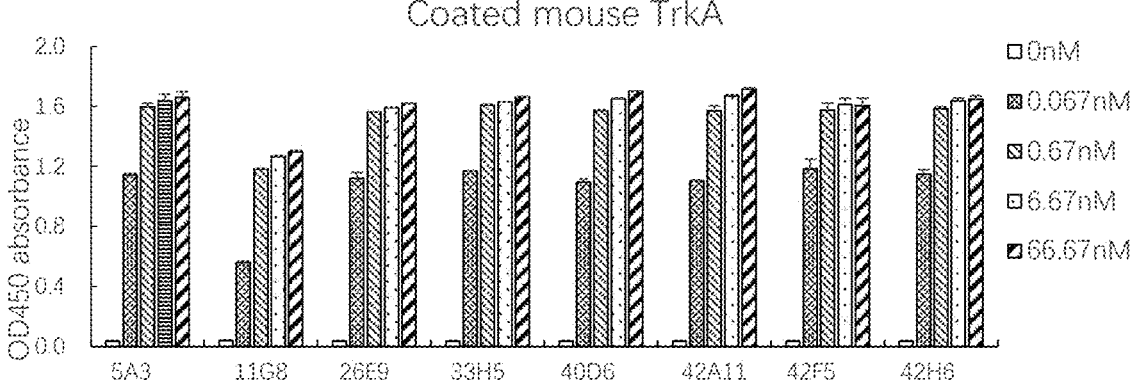
FIG. 4 shows the ELISA results of the binding of the anti-TrkA antibodies of the present invention to mouse TrkA protein.
Figure 5:
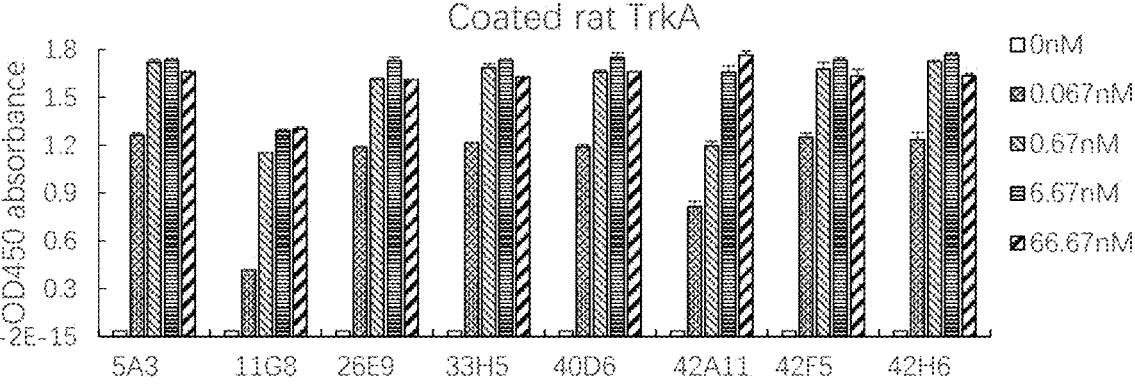
FIG. 5 shows the ELISA results of the binding of the anti-TrkA antibodies of the present invention to rat TrkA protein.

In addition, the species cross-reactivities of anti-TrkA antibodies were detected with monkey TrkA (Hangzhou Haoyang Biotechnology Co., Ltd., HSP037-05), rat TrkA (Beijing Yiqiao Shenzhou Technology Co., Ltd., 80243-R03H), mouse TrkA (Beijing Yiqiao Shenzhou Technology Co., Ltd., 51103-M02H) extracellular region fusion protein (fused to human Fc). The ELISA results show that all of the eight anti-TrkA antibodies can strongly bind to TrkA proteins of the three other species. The results are shown in FIGS. 3-5.

TABLE 1

| EC50 values of the eight anti-TrkA antibodies binding to human TrkA (33-417) | | | | | | | |
|---|---|---|---|---|---|---|---|
| Antibodies | 5A3 | 11G8 | 26E9 | 33H5 | 40D6 | 42F5 | 42H6 | 42A11 |
| EC50 (nM) | 0.242 | 0.114 | 0.099 | 0.204 | 0.202 | 0.128 | 0.135 | 0.187 |

TABLE 2

| EC50 values of the eight anti-TrkA antibodies binding to human TrkA (192-402) | | | | | | | |
|---|---|---|---|---|---|---|---|
| Antibodies | 5A3 | 11G8 | 26E9 | 33H5 | 40D6 | 42F5 | 42H6 | 42A11 |
| EC50 (nM) | 0.154 | 0.071 | 0.068 | 0.173 | 0.195 | 0.134 | 0.175 | 0.234 |

Example 3: Affinity Assay of Murine Anti-TrkA Antibodies Binding to Human TrkA The affinities of the antibodies were detected with Biomolecular Interaction Detection Platform (ForteBio Octet Red96 (PALL)).

Human TrkA extracellular region (33-417) protein containing human Fc tag was fixed onto a chip by using an anti-human Fc capture sensor (Fortebio, 18-5088), and then bound to gradient concentrations of anti-TrkA antibody. Buffer (1×Kinetics Buffer: PBS+0.1% BSA+0.05% Tween20) was added for dissociation, and finally the affinity kinetic constants of antigen-antibody binding were calculated by instrument algorithm. The results are shown in Table 3.

TABLE 3

| Affinities of anti-TrkA antibodies binding to human TrkA | | | |
|---|---|---|---|
| Antibodies | $K_D$ (M) | $k_{on}$ (1/Ms) | $k_{dis}$ (1/s) |
| 5A3 | 1.55E−11 | 1.21E+06 | 1.88E−05 |
| 11G8 | <1.0E−12 | 9.92E+05 | <1.0E−07 |
| 26E9 | 2.67E−11 | 9.23E+05 | 2.46E−05 |
| 33H5 | 1.62E−11 | 1.29E+06 | 2.09E−05 |
| 40D6 | 2.71E−11 | 9.18E+05 | 2.49E−05 |
| 42F5 | 2.18E−12 | 9.47E+05 | 2.07E−06 |
| 42H6 | 6.77E−12 | 1.47E+06 | 9.91E−06 |
| 42A11 | 1.42E−12 | 8.89E+05 | 1.26E−06 |

Figure 6:
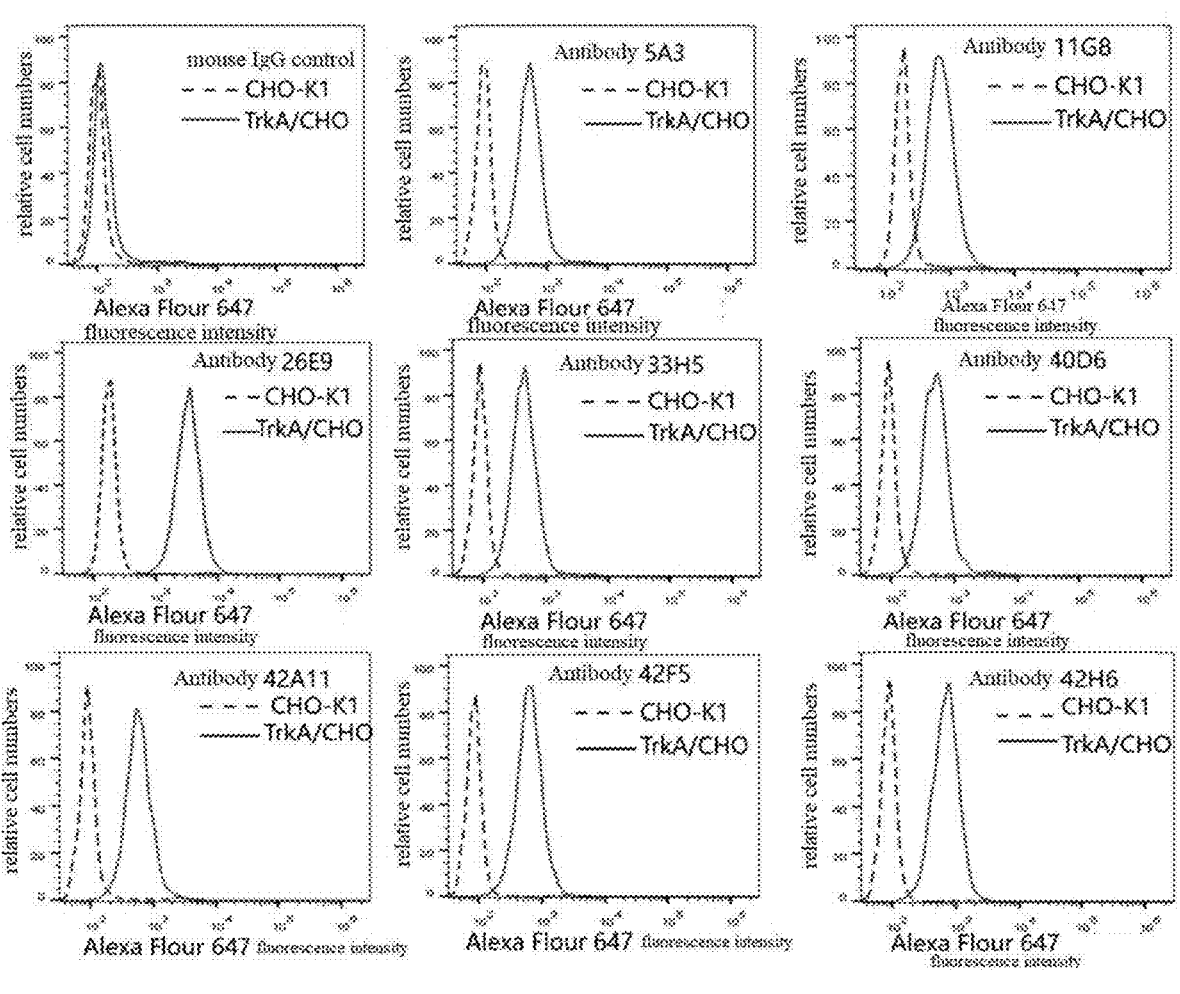
FIG. 6 shows the FACS results of the binding of the anti-TrkA antibodies of the present invention to CHO cells expressing human TrkA protein.

Example 4: Detection of Murine Anti-TrkA Antibodies Binding to TrkA/CHO Cells by Flow Cytometry The binding of anti-TrkA antibodies to CHO-K1 cells expressing full-length TrkA (TrkA/CHO) was detected by flow cytometry (FACS). TrkA/CHO cells were cultured in F12K medium (Hyclone, SH30026) containing 10% FBS and 5 μg/mL puromycin, and the negative control cells CHO-K1 were cultured in F12K medium containing 10% FBS. Cells were collected during the logarithmic growth phase, resuspended in PBS containing 2% FBS, and added to each well of a 96-well plate at $10^5$ cells (50 μl). 50 μl of 20 μg/mL anti-TrkA antibody, or mouse IgG control was added, and reacted at room temperature for 1 hour. 1 μg/mL Alexa Flour 647-labeled goat anti-mouse IgG antibody (Jackson, 115-605-062) was added and incubated at room temperature for 30 minutes. The binding of antibodies was detected by flow cytometry (BioRad, ZE5). As shown in FIG. 6, all of the eight anti-TrkA antibodies bind to TrkA/CHO cells, but not to CHO-K1 cells; the control antibody mouse IgG neither binds to CHO-K1 nor to TrkA/CHO.

Example 5: Murine Anti-TrkA Antibodies Block the Binding of Human TrkA to the Ligand NGF A control antibody BXhVH5VL1 was synthesized based on the sequence information provided by Chinese patent application CN101939337A, with reference to the optimal antibody BXhVH5VL1 therein, having the heavy chain variable region of (SEQ ID NO: 5) and the light chain variable region of (SEQ ID NO: 7).

Each well of a 96-well microtiter plate was coated with 50 ng of TrkA extracellular region (33-417) protein fused to human Fc, washed three times and blocked with 3% BSA for 1 hour. 10,000 ng/mL (66.67 nM) anti-TrkA antibody was 3-fold serially diluted up to 10 concentrations, until to 0.17 ng/mL (0.0011 nM). Each well was added with 100 μl and incubated at room temperature for 30 minutes. 100 μl of 1 μg/mL biotin-labeled human NGF was added, incubated at room temperature for 1 hours, and washed for three times. Streptavidin-labeled horseradish peroxidase (Streptavidin-HRP, Biolegend, 405210) was added and incubated for 0.5 hours. After washing three times, TMB was added to the plate, and the absorbance at 450 nm was read by a microplate reader after the color development was terminated.

Figure 7:
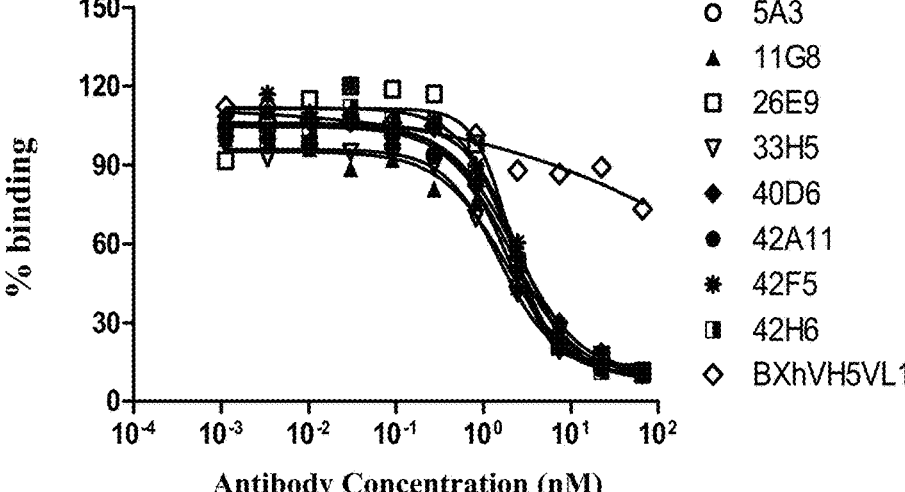
FIG. 7 is a schematic diagram showing efficiencies of the anti-TrkA antibodies of the present invention and of the prior art to block the binding of human TrkA to ligand NGF.

The results are shown in FIG. 7. The anti-TrkA antibodies of the present invention can block the binding of human TrkA to the ligand NGF, and the blocking effect is significantly enhanced with the increase of antibody concentration. When the antibody concentration reaches 20 nM, the eight anti-TrkA antibodies can almost completely block the binding of TrkA to NGF. While the control antibody BXhVH5VL1 has no significant effect on blocking TrkA binding to NGF at all of the tested concentrations (0.001-100 nM). The IC50 values of the eight anti-TrkA antibodies of the present invention and BXhVH5VL1 for blocking the binding of human TrkA to the ligand NGF are shown in Table 4.

TABLE 4

| IC50 of anti-TrkA antibodies for blocking TrkA-NGF binding | | | | | | | | |
|---|---|---|---|---|---|---|---|---|
| Antibodies | 5A3 | 11G8 | 26E9 | 33H5 | 40D6 | 42F5 | 42H6 | 42A11 | BXhVH5VL1 |
| IC50 (nM) | 1.763 | 1.900 | 2.040 | 1.498 | 2.284 | 2.352 | 2.185 | 2.054 | >100 |

Example 6: Detection of the In Vitro Neutralization Activities of Murine Anti-TrkA Antibodies

A. NGF-Induced TF-1 Cell Proliferation

Figure 8:
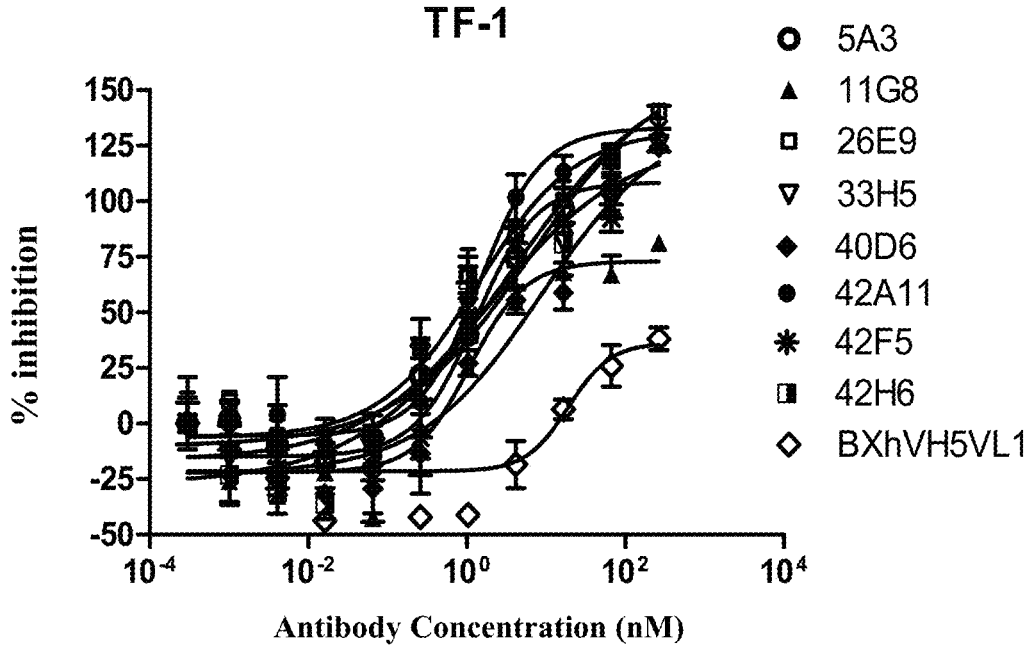
FIG. 8 is a schematic diagram showing efficiencies of the anti-TrkA antibodies of the present invention and of the prior art to inhibit NGF-induced TF-1 cell proliferation.

The growth of TF-1 cells (human blood leukemia cells, ATCC, CRL-2003) is highly dependent on GM-CSF (Granulocyte-Macrophage Colony-Stimulating Factor). NGF can also induce the growth of TF-1 cells after binding to TrkA on the surface of TF-1 cells to activate the downstream signaling pathway, thereby eliminating the need of GM-CSF. TF-1 cells were cultured in RPMI 1640 culture medium (HyClone, SH30027) containing 10% FBS (Gibco, 10091148) and 2 μg/mL GM-CSF (R&D, 215-GM-010), cells were collected during logarithmic growth phase, washed thoroughly to remove the GM-CSF comprised in the original medium, and resuspended with GM-CSF-free medium. 5000 cells per well were diluted in 80 μl medium and plated into a white 96-well cell culture plate with transparent bottom (Corning, 3610). Anti-TrkA antibody was 4-fold serially diluted, starting from 400 μg/mL (2666.67 nM) to prepare 10 concentrations, 10 μL was added into each well, and incubated at room temperature for 0.5 hours. 10 μL of 50 ng/mL human NGF was added to each well. After incubation at 37° C., 5% $CO_2$ for 72 hours, 100 μL of CellTiter-Glo® Cell Viability Detection Reagent (Promega, G7573) was added, and the optical luminescence signals were read by using a Multimode Reader (Spectra- Max). As shown in FIG. 8, the anti-TrkA antibodies of the present invention are capable of inhibiting the proliferation of TF-1 cells induced by human NGF, and the IC50 values are shown in Table 5. The inhibitory effect of antibody BXhVH5VL1 on the proliferation of TF-1 cells is much weaker than those of the antibodies of the present invention. When the antibody concentration is 40 μg/mL (266.67 nM), the anti-TrkA antibodies of the present invention can completely inhibit the NGF-induced TF-1 cell proliferation, whereas the inhibition rate of the antibody BXhVH5VL1 on the NGF-induced TF-1 cell proliferation at this concentration is less than 40%.

TABLE 5

| IC50 values of the anti-TrkA antibodies inhibiting NGF-induced TF-1 cell proliferation | | | | | | | | |
|---|---|---|---|---|---|---|---|---|
| Antibodies | 5A3 | 11G8 | 26E9 | 33H5 | 40D6 | 42F5 | 42H6 | 42A11 | BXhVH5VL1 |
| IC50 (nM) | 6.487 | 1.092 | 1.393 | 2.136 | 8.532 | 1.302 | 3.576 | 1.462 | >200 |

B. Assay of NGF-Induced TrkA/Ba/F3 Cell Proliferation

The growth of Ba/F3 cells involves two pathways: IL3-dependent and IL3-independent. The IL3-independent growth requires Ba/F3 cells to stably express active kinases. Ba/F3 cells expressing full-length human TrkA (TrkA/Ba/F3) were constructed, and the proliferation of such cells requires the addition of NGF for induction.

TrkA/Ba/F3 cells were cultured in RPMI 1640 culture medium containing 10% FBS and 100 ng/mL NGF. The cells were collected and washed thoroughly to remove NGF comprised in the original growth medium, 3000 cells per well were resuspended in 80 μL of NGF-free medium and plated in a white 96-well cell culture plate with transparent bottom (Corning, 3610). 10 μL of serially diluted anti-TrkA antibody was added to the cells in each well, incubated at room temperature for 0.5 hours, and 10 μL of 50 ng/mL human NGF was added to each well at the final concentration of 5 ng/mL. The highest concentration of serially diluted anti-NGF antibody was 40 μg/mL (266.67 nM). After incubation at 37° C., 5% $CO_2$ for 48 hours, 100 μL of CellTiter-Glo® Cell Viability Detection Reagent (Promega, G7573) was added. Optical luminescence signals were read by using a Multimode Reader (SpectraMax).

Figure 9:
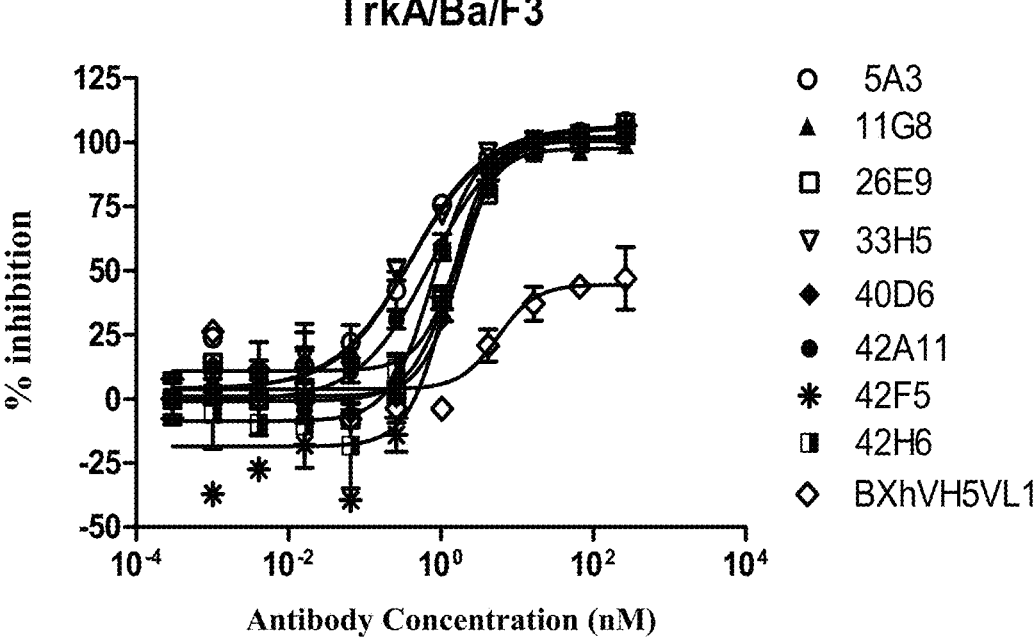
FIG. 9 is a schematic diagram showing efficiencies of the anti-TrkA antibodies of the present invention and of the prior art to inhibit NGF-induced TrkA/Ba/F3 cell proliferation.

During the observation of the growth of TrkA/Ba/F3 cells, the proliferation of the cells added with human NGF is normal; the eight anti-TrkA antibodies of the present invention can all inhibit the NGF-induced TrkA/Ba/F3 cell proliferation, and the inhibitory effect is increased with the increase of the concentration. When the antibody concentration is increased to 2.5 μg/mL (16.67 nM) or higher, the anti-TrkA antibodies inhibit the TrkA/Ba/F3 cell proliferation by 100%; while the inhibition rate of antibody BXhVH5VL1 at the highest concentration of 40 μg/mL (266.67 nM) for TrkA/Ba/F3 cell proliferation is less than 50% (FIG. 9). IC50 values are as shown in Table 6.

Example 7: Detection of the Binding of Murine Anti-TrkA Antibodies to TrkA Proteins of the Same Family Each well of a 96-well microtiter plate was coated with 50 ng of human TrkA extracellular region protein, human TrkB extracellular region protein (Beijing Yiqiao Shenzhou Technology Co., Ltd., 10047-H03H), human TrkC extracellular region protein (Beijing Yiqiao Shenzhou Technology Co., Ltd., 10048-H03H). The bindings of the anti-TrkA antibodies to human TrkA and the two proteins of the same family were detected according to the method described in Example 2.

Figure 10:
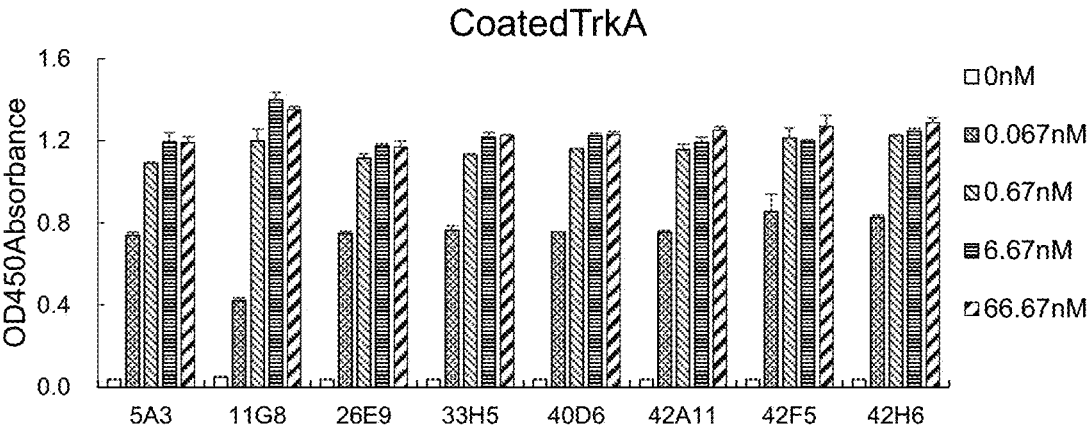
FIG. 10 shows the ELISA results of the binding of the anti-TrkA antibodies of the present invention to human TrkA.
Figure 11:
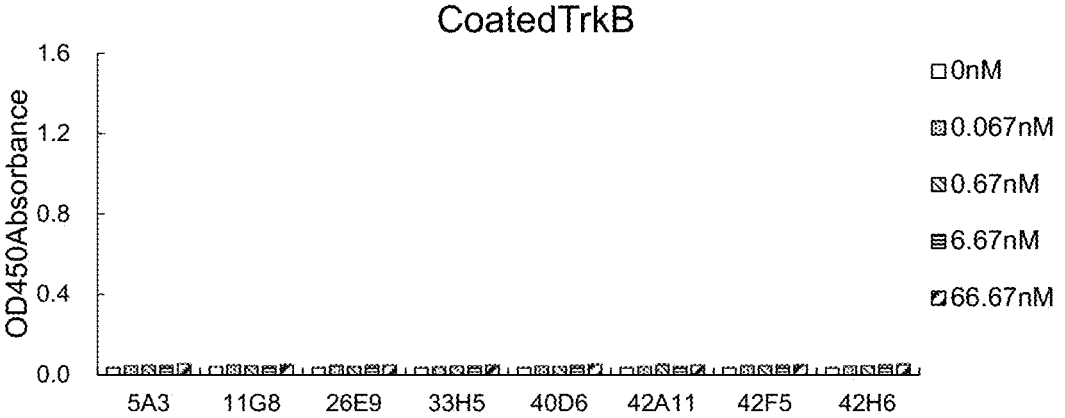
FIG. 11 shows the ELISA results of the binding of the anti-TrkA antibodies of the present invention to human TrkB.
Figure 12:
FIG. 12 shows the ELISA results of the binding of the anti-TrkA antibodies of the present invention to human TrkC.
Figure 13:
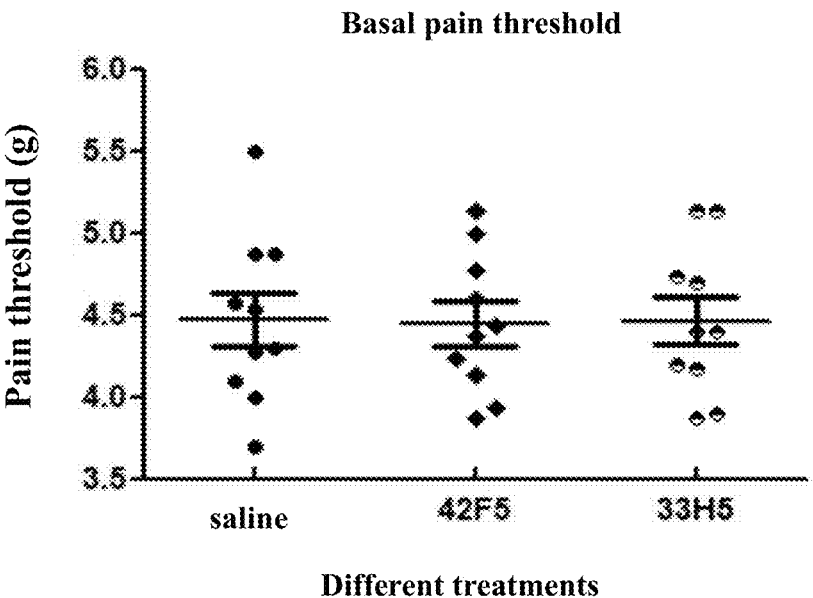
FIG. 13 shows the basal pain threshold of the CFA-induced inflammatory mouse model, which was measured by VonFrey before the injection of the modeling agent CFA into the planta.

Eight murine anti-TrkA antibodies can bind to TrkA with high affinity (FIG. 10), but substantially do not bind to TrkB (FIG. 11) and TrkC (FIG. 12).

Example 8: The Effects of Anti-TrkA Antibodies on CFA-Induced Inflammatory Pain in Mice C57BL/6 mice (Zhejiang Weitong Lihua Laboratory Animal Technology Co., Ltd.), male, SPF grade, 6-8 weeks old, were kept for 5-day adaptive feeding. After the adaptation, the animals were divided into 3 groups, namely the saline group, the anti-TrkA antibody 33H5 group, and the anti-TrkA antibody 42F5 group, 10 animals in each group. The pain threshold (i.e., basal pain threshold) was measured by VonFrey before the injection of the modeling agent CFA into the planta.

Figure 14:
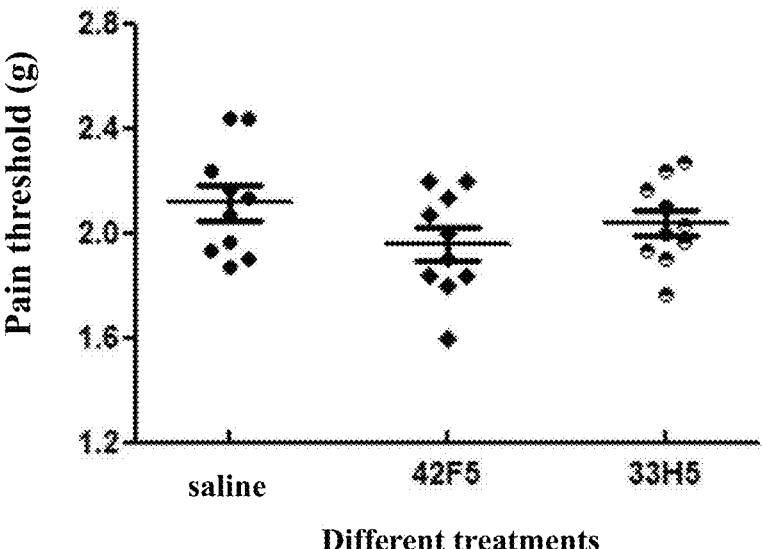
FIG. 14 shows the pain threshold (i.e., pre-dose pain threshold) of the CFA-induced inflammatory mouse model about 24 hours after the injection of the modeling agent CFA into the planta.

On the next day, mice were injected with 25 μl CFA to the planta to induce inflammation. After the toes were significantly swollen (about 24 hours after modeling), the pain threshold was measured in mouse planta in a similar way, which was taken as the pre-dose pain threshold (FIG. 14).

Figure 15:
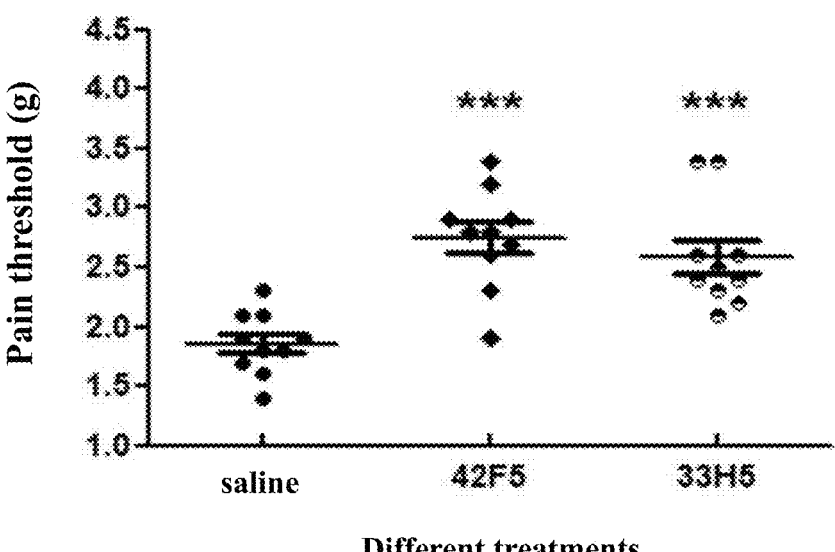
FIG. 15 shows the pain threshold of the CFA-induced inflammatory mouse model 24 hours after being treated with the anti-TrkA antibodies 33H5 and 42F5 of the present invention, wherein *P<0.05 v.s. normal saline; ***P<0.001 v.s. normal saline.
Figure 16:
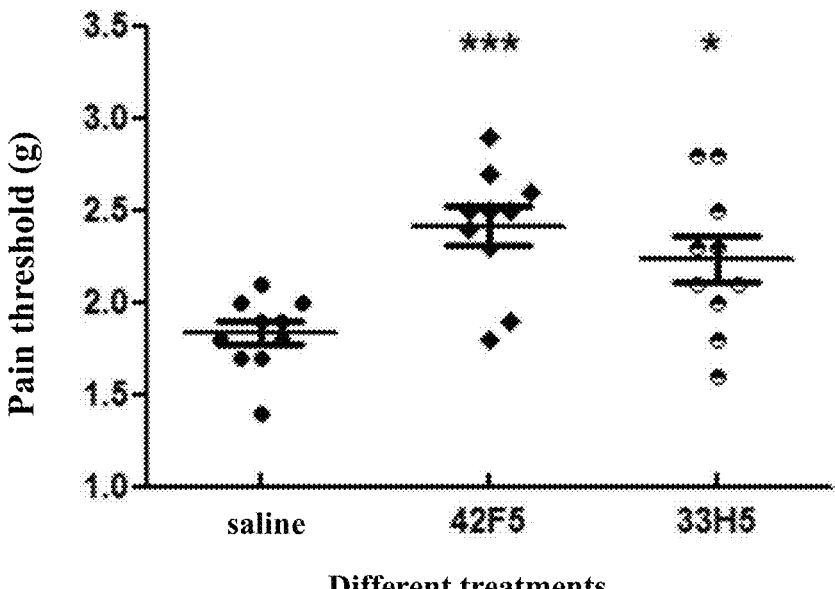
FIG. 16 shows the pain threshold of the CFA-induced inflammatory mouse model 48 hours after being treated with the anti-TrkA antibodies 33H5 and 42F5 of the present invention, wherein *P<0.05 v.s. normal saline; ***P<0.001 v.s. normal saline.

Subsequently, each group were subcutaneously injected with normal saline, anti-TrkA antibody 33H5, or anti-TrkA antibody 42F5 at a dose of 10 mg/kg, and the pain thresholds were measured at 24 hours and 48 hours post administration (FIGS. 15-16). The effects of the test substances on pain threshold were evaluated.

The results are shown in FIGS. 13-16. Both anti-TrkA antibodies 33H5 and 42F5 can significantly improve the CFA-induced decrease in pain threshold at 24 h and 48 h post administration, and there are statistical differences compared to the normal saline group.

TABLE 6

| IC50 values of the anti-TrkA antibodies inhibiting NGF-induced TrkA/Ba/F3 cell proliferation | | | | | | | | |
|---|---|---|---|---|---|---|---|---|
| Antibodies | 5A3 | 11G8 | 26E9 | 33H5 | 40D6 | 42F5 | 42H6 | 42A11 | BXhVH5VL1 |
| IC50 (nM) | 0.422 | 1.646 | 1.539 | 0.413 | 1.805 | 1.252 | 0.782 | 0.738 | >200 |

Example 9: Sequencing and Sequence Analysis of Murine Anti-TrkA Antibody Variable Regions Total RNA of hybridoma cells was extracted by using TRIzol kit (Ambion, 15596-026), and was used as a template to synthesize the first-strand cDNA (Takara). The antibody light chain and heavy chain fragments were obtained by rapid amplification of cDNA ends (RACE), and the amplified fragments were cloned into standard vectors respectively. After sequencing, the sequences of the heavy chain and light chain variable regions of the anti-TrkA antibodies 5A3, 11G8, 26E9, 33H5, 40D6, 42F5, 42H6 and 42A11 obtained are as follows:

```
Anti-TrkA Antibody 5A3:
Amino acid sequence of the heavy chain variable region:
                                            (SEQ ID NO: 49)
QVQLQQSGAELMKPGASVKISCKAIGYTFSRYWIEWVKQRPGHGLEWIGEILPGRGVTN

YNENFKGKATFTVDISSTTTYIQFSSLTSEDSAVYYCARSNYGDYDFWGQGTSLTVSS

Nucleic acid sequence of the heavy chain variable region:
                                            (SEQ ID NO: 65)
CAGGTTCAGCTGCAGCAGTCTGGAGCTGAGCTGATGAAGCCTGGGGCCTCAGTGAA

GATATCCTGCAAGGCTATTGGGTACACATTCAGTAGGTACTGGATAGAGTGGGTAAAGCAG

AGGCCTGGACATGGCCTTGAGTGGATTGGAGAGATTTTACCTGGAAGAGGTGTTACTAAC

TACAATGAGAACTTCAAGGGCAAGGCCACATTCACTGTAGATATATCCTCCACCACAACCT

ACATTCAATTCAGCAGCCTGACATCTGAGGACTCTGCCGTCTATTACTGTGCAAGATCGAA

TTATGGTGACTACGACTTCTGGGGCCAAGGCACCTCTCTCACAGTCTCCTCA

Amino acid sequence of the light chain variable region:
                                            (SEQ ID NO: 57)
QTVVTQESALTTSPGETVTLTCRSSSGAVTTSNHANWVQEKPDHLFTSLMGGTNNRAPG

VPARFSGSLIGDKAALTITGAQTEDEAIYFCALWYSNHWVFGGGTKLTVL

Nucleic acid sequence of the light chain variable region:
                                            (SEQ ID NO: 66)
CAGACTGTTGTGACTCAGGAATCTGCACTCACCACATCACCTGGTGAAACAGTCACA

CTCACTTGTCGCTCAAGTTCTGGGGCTGTTACAACTAGTAACCATGCCAACTGGGTCCAA

GAAAAACCTGATCATTTATTCACTAGTCTAATGGGTGGTACCAATAACCGAGCTCCAGGTG

TTCCTGCCAGATTCTCAGGCTCCCTGATTGGCGACAAGGCTGCCCTCACCATCACAGGGG

CGCAGACTGAGGATGAGGCAATATATTTCTGTGCTCTCTGGTACAGCAACCATTGGGTGTT

CGGTGGAGGAACTAAACTGACTGTCCTA

Anti-TrkA Antibody 11G8:
Amino acid sequence of the heavy chain variable region:
                                            (SEQ ID NO: 50)
QVQLQQPGAELVKPGASVKLSCKASGYTFTSYWMHWVKQRPGQGLEWIGEINPNNGL

TNYDEKFKTKATLTIDKSSRTAYIQLSSLTSEDSAVYYCAKYGNYVAFAFWGQGTLVTVSA

Nucleic acid sequence of the heavy chain variable region:
                                            (SEQ ID NO: 67)
CAGGTCCAACTGCAGCAGCCTGGGGCTGAACTGGTGAAGCCTGGGGCTTCAGTGAA

GCTGTCCTGCAAGGCTTCCGGCTACACCTTTACCAGCTACTGGATGCACTGGGTGAAGCA

GAGGCCTGGACAAGGCCTTGAGTGGATTGGAGAGATTAATCCTAACAACGGTCTTACTAA

CTACGATGAGAAATTCAAGACCAAGGCCACACTGACCATAGACAAATCCTCCAGAACAGC

CTACATACAACTCAGCAGCCTGACATCTGAGGACTCTGCGGTCTATTACTGTGCAAAATAT

GGTAACTACGTCGCGTTTGCTTTCTGGGGCCAAGGGACTCTGGTCACTGTCTCTGCA

Amino acid sequence of the light chain variable region:
                                            (SEQ ID NO: 58)
DIQMTQSPASLSATVGETVTITCRASENIYSYVAWYQQKQGKSPQLLVHNAKTLAEGVPS

RFSGSGSGTQFSLKINGLHPEDFGSYYCQHHYGIPLTFGAGTKLELK
```

-continued

Nucleic acid sequence of the light chain variable region:

(SEQ ID NO: 68)

GACATTCAGATGACTCAGTCTCCAGCCTCCCTATCTGCAACTGTGGGAGAAACTGTC

ACCATCACATGTCGAGCAAGTGAAAATATTTACAGTTATGTAGCATGGTATCAGCAGAAAC

AGGGAAAATCTCCTCAACTCCTGGTCCATAATGCAAAAACCTTAGCAGAAGGTGTACCAT

CAAGGTTCAGTGGCAGTGGATCAGGCACACAGTTTTCTCTGAAGATCAACGGCCTGCACC

CTGAAGATTTTGGGAGTTATTACTGTCAACATCATTATGGTATTCCGCTCACGTTCGGCGCT

GGGACCAAGCTGGAGCTGAAA

Anti-TrkA Antibody 26E9:
Amino acid sequence of the heavy chain variable region:

(SEQ ID NO: 51)

QVQLQQPGAELVKPGASVKLSCKSSGYTFTNYWMHWVKQRPGQGLEWIGEIYPSNGRT

NYNEKFKNRATLTVDISSSTAYMQLSSLTSEDSAVYYCARSRYDPMEDWGQGTSVTVSS

Nucleic acid sequence of the heavy chain variable region:

(SEQ ID NO: 69)

CAGGTCCAACTGCAGCAGCCTGGGGCTGAACTGGTGAAGCCTGGGGCTTCTGTGAA

GCTGTCCTGCAAGTCTTCTGGCTATACCTTCACCAACTACTGGATGCACTGGGTGAAGCA

GCGGCCTGGACAAGGCCTTGAGTGGATTGGAGAGATTTATCCTAGCAACGGTCGTACTAA

CTACAATGAGAAGTTCAAAAACAGGGCCACACTGACTGTAGACATTTCCTCCAGCACAGC

CTACATGCAACTCAGCAGCCTGACATCTGAGGACTCTGCGGTCTATTACTGTGCAAGGAG

TAGGTACGACCCTATGGAAGACTGGGGTCAAGGAACCTCAGTCACCGTCTCCTCT

Amino acid sequence of the light chain variable region:

(SEQ ID NO: 59)

QIVLTQSPAIMSASPGEKVTMTCSASSSVGYMHWYQQKSGTSPKRWIYDTSKLASGVPT

RFSGSGSGTSYSLTISSMEAEDAATYYCQQWSSIPLTFGSGTKLEIK

Nucleic acid sequence of the light chain variable region:

(SEQ ID NO: 70)

CAAATTGTTCTCACCCAGTCTCCAGCAATCATGTCTGCATCTCCAGGGGAGAAGGTC

ACCATGACCTGCAGTGCCAGCTCAAGTGTGGGTTACATGCACTGGTACCAGCAGAAGTCA

GGCACCTCCCCCAAAAGATGGATTTATGACACATCCAAACTGGCTTCTGGAGTCCCAACT

CGCTTCAGTGGCAGTGGGTCTGGGACCTCTTACTCTCTCACAATCAGCAGCATGGAGGCT

GAGGATGCTGCCACTTATTACTGCCAGCAGTGGAGTAGTATCCCACTCACGTTCGGCTCGG

GGACAAAGTTGGAAATAAAG

Anti-TrkA Antibody 33H5:
Amino acid sequence of the heavy chain variable region:

(SEQ ID NO: 52)

QVQLQQPGAELVKPGASVQLSCKASGYTFTSYWIHWVKQRPGQGLEWIGEINPNNGLT

NYIEKFKNKATLTIDKSSNTAYMQLSGLTPEDSAVYYCAKYGNYVAFAYWGQGTLVTVSA

Nucleic acid sequence of the heavy chain variable region:

(SEQ ID NO: 71)

CAGGTCCAACTGCAGCAGCCTGGGGCTGAACTGGTGAAGCCTGGGGCTTCAGTGCA

GCTGTCCTGCAAGGCTTCTGGCTACACCTTCACCAGTTACTGGATACACTGGGTGAAACA

GAGGCCTGGACAAGGCCTTGAGTGGATTGGAGAGATTAATCCTAACAACGGTCTTACTAA

CTACATTGAGAAATTCAAGAACAAGGCCACACTGACTATTGACAAATCCTCCAACACAGC

CTACATGCAACTCAGCGGCCTGACACCTGAGGACTCTGCGGTCTATTACTGTGCAAAATAT

GGTAACTACGTCGCGTTTGCTTACTGGGGCCAGGGGACTCTGGTCACTGTCTCTGCA

Amino acid sequence of the light chain variable region:
                                         (SEQ ID NO: 60)
DIQMTQSPASLSASVGDTVTITCRASENIYTYLAWYQQKQGKSPQLLVHNTKTLAEGVP

SRFSGSGSGTQFSLKISSLQPEDFGTYYCQHHYGVPLTFGAGTKLELK

Nucleic acid sequence of the light chain variable region:
                                         (SEQ ID NO: 72)
GACATCCAGATGACTCAGTCTCCAGCCTCCCTATCTGCATCTGTGGGAGACACTGTCA

CCATCACATGTCGAGCAAGTGAAAATATCTACACTTATTTAGCTTGGTATCAGCAGAAACA

GGGAAAATCTCCTCAACTCCTGGTCCATAATACAAAAACCTTAGCAGAAGGTGTGCCCTC

AAGGTTCAGTGGCAGTGGATCAGGCACACAGTTTTCTCTGAAGATCAGCAGCCTGCAGCC

TGAAGATTTTGGGACTTATTACTGTCAACATCATTATGGTGTTCCGCTCACGTTCGGTGCTG

GGACCAAGCTGGAGCTGAAA

Anti-TrkA Antibody 40D6:
Amino acid sequence of the heavy chain variable region:
                                         (SEQ ID NO: 53)
QVQLQQSGTELMKPGASVKISCKATGYTFSRYWIEWVKQRPGHGLEWIGEILPGRSSTN

YNEKFKGKATFTADTSSNTAYMQLSSLTSEDSAVYYCTRVSQLHIYFDYWGQGTTVTVSS

Nucleic acid sequence of the heavy chain variable region:
                                         (SEQ ID NO: 73)
CAGGTTCAGCTGCAGCAGTCTGGAACTGAACTGATGAAGCCTGGGGCCTCAGTGAA

GATATCCTGCAAGGCTACTGGCTACACATTCAGTAGATACTGGATAGAGTGGGTAAAACAG

AGGCCTGGACATGGCCTTGAGTGGATTGGAGAGATTTTACCTGGAAGGAGTAGTACTAAC

TACAATGAGAAGTTCAAGGGCAAGGCCACATTCACTGCCGATACATCCTCCAACACAGCC

TACATGCAACTCAGCAGCCTGACATCTGAGGACTCTGCCGTCTATTACTGTACAAGAGTTT

CCCAACTGCACATTTACTTTGACTACTGGGGCCAAGGGACCACTGTCACAGTCTCCTCC

Amino acid sequence of the light chain variable region:
                                         (SEQ ID NO: 61)
DIVMTQVVPSVPVTPGESVSISCRSSKSLLHSNGNTYLYWFQQRPGQSPQLLIYRMSNLA

SGVPDRFSGSGSGTAFTLRISRVEAEDVAFYYCMQHLEFPLTFGAGTKLELK

Nucleic acid sequence of the light chain variable region:
                                         (SEQ ID NO: 74)
GATATTGTGATGACTCAGGTTGTACCCTCTGTACCTGTCACTCCTGGAGAGTCAGTAT

CCATCTCCTGCAGGTCTAGTAAGAGTCTCCTGCATAGTAATGGCAACACTTACTTATATTGG

TTCCAGCAGAGGCCAGGCCAGTCTCCTCAGCTCCTGATATATCGGATGTCCAACCTTGCCT

CAGGAGTCCCAGACAGGTTCAGTGGCAGTGGGTCAGGAACTGCTTTCACATTGAGAATC

AGTAGAGTGGAGGCTGAGGATGTGGCTTTTTATTACTGTATGCAACATCTAGAATTTCCGC

TCACGTTCGGTGCTGGGACCAAGTTGGAGCTGAAA

Anti-TrkA Antibody 42F5:
Amino acid sequence of the heavy chain variable region:
                                         (SEQ ID NO: 54)
QVQLQQPGAELVKPGASVKLSCKSSGYTFTNYWMHWVRQRPGQGLEWIGEIYPNNGR

VNYNEKFKNRATLTVDISSSTAYMQLSSLTSEDSAVYYCARSRYDPMEDWGQGTSVTVSS

Nucleic acid sequence of the heavy chain variable region:
                                         (SEQ ID NO: 75)
CAGGTCCAACTGCAGCAGCCTGGGGCTGAACTGGTGAAACCTGGGGCTTCAGTGAA

GCTGTCCTGCAAGTCTTCTGGCTATACCTTCACCAACTACTGGATGCACTGGGTGAGGCA

GAGGCCTGGACAAGGCCTTGAGTGGATTGGAGAGATCTATCCTAACAACGGTCGTGTTAA

CTACAATGAGAAGTTCAAGAACAGGGCCACACTGACTGTAGACATATCCTCCAGCACAGC

-continued

```
CTACATGCAACTCAGCAGCCTGACATCTGAGGACTCTGCGGTCTATTACTGTGCAAGGAG

TAGGTACGACCCTATGGAAGACTGGGGTCAAGGAACCTCAGTCACCGTCTCCTCT
```

Amino acid sequence of the light chain variable region:
(SEQ ID NO: 62)
```
QVVLTQSPAIMSASPGEKVTMTCSASSSVGYMHWYQQKSGTSPKRWIYDTSKLASGVP

TRFSGSGSGTSYSLTISSMEAEDAATYFCQQWSSIPLTFGSGTRLEIK
```

Nucleic acid sequence of the light chain variable region:
(SEQ ID NO: 76)
```
CAAGTTGTTCTCACCCAGTCTCCAGCAATCATGTCTGCATCTCCAGGGGAGAAGGTC

ACCATGACCTGCAGTGCCAGCTCAAGTGTAGGTTACATGCACTGGTACCAGCAGAAGTCA

GGCACCTCCCCCAAAAGATGGATTTATGACACATCCAAACTGGCTTCTGGAGTCCCAACT

CGCTTCAGTGGCAGTGGGTCTGGGACCTCTTACTCTCTCACAATCAGCAGCATGGAGGCT

GAGGATGCTGCCACTTATTTCTGCCAGCAGTGGAGTAGTATCCCACTCACGTTCGGCTCGG

GGACAAGGTTGGAAATAAAG
```

Anti-TrkA Antibody 42H6:
Amino acid sequence of the heavy chain variable region:
(SEQ ID NO: 55)
```
QVQLQQPGVELVKPGASVKLSCKTSGYTFTSYWMHWVKQRPGQGLEWIGEIYSSNGLT

NYNEKFKNKATLTVDKSSSTAYMQLTSLTSEDSAIYYCARHWYVFLDHWGQGTTLTVSS
```

Nucleic acid sequence of the heavy chain variable region:
(SEQ ID NO: 77)
```
CAGGTCCAACTGCAGCAGCCTGGGGTTGAACTGGTGAAGCCTGGGGCTTCAGTGAA

GCTGTCCTGCAAGACTTCTGGCTACACCTTCACCAGCTACTGGATGCACTGGGTGAAGCA

GAGGCCTGGACAAGGCCTTGAATGGATTGGAGAGATTTATTCCAGTAACGGTCTTACTAA

CTACAATGAGAAGTTCAAGAATAAGGCCACACTGACTGTAGATAAATCCTCCAGCACAGC

CTACATGCAACTCACCAGCCTGACATCTGAAGACTCTGCGATCTATTACTGTGCAAGACAT

TGGTACGTCTTCCTTGACCACTGGGGCCAAGGCACCACTCTCACAGTCTCCTCA
```

Amino acid sequence of the light chain variable region:
(SEQ ID NO: 63)
```
QAVVTQESALTTSPGETVTLTCRSSTGAVTTSNHANWVQEKPDHLFTGLIGGINNRAPGV

PARFSGSLIGDKAALTITGAQTEDEAIYFCALWYSNHWVFGGGTRLTVL
```

Nucleic acid sequence of the light chain variable region:
(SEQ ID NO: 78)
```
CAGGCTGTTGTGACTCAGGAATCTGCACTCACCACATCACCTGGTGAAACAGTCACA

CTCACTTGTCGCTCAAGTACTGGGGCTGTTACAACTAGTAACCATGCCAACTGGGTCCAA

GAAAAACCAGATCATTTATTCACTGGTCTAATAGGTGGTATCAACAACCGAGCTCCAGGTG

TTCCTGCCAGATTCTCAGGCTCCCTGATTGGAGACAAGGCTGCCCTCACCATCACAGGGG

CACAGACTGAGGATGAGGCAATATATTTCTGTGCTCTATGGTACAGCAATCATTGGGTGTT

CGGTGGAGGAACCAGACTGACTGTCCTA
```

Anti-TrkA Antibody 42A11:
Amino acid sequence of the heavy chain variable region:
(SEQ ID NO: 56)
```
QVQLQQPGAELVKPGASVKLSCKASGYTFTNYWMHWVKQRPGQGLEWIGEIYPSNGR

TNYNEKFKTKATLTVDKSSSTAYMHLSSLTSEDSAVYYCAGSRYDAMDFWGQGTSVTVSS
```

Nucleic acid sequence of the heavy chain variable region:
(SEQ ID NO: 79)
```
CAGGTCCAACTGCAGCAGCCTGGGGCTGAACTTGTGAAGCCTGGGGCTTCAGTGAA

GCTGTCCTGTAAGGCTTCTGGCTACACCTTCACCAACTACTGGATGCATTGGGTGAAACA

GAGGCCTGGACAAGGCCTTGAGTGGATTGGAGAGATTTATCCTAGCAACGGTCGTACTAA
```

-continued

CTACAATGAGAAGTTCAAGACCAAGGCCACACTGACTGTAGACAAATCCTCCAGCACAG

CCTACATGCATCTCAGCAGCCTGACATCTGAGGACTCTGCGGTCTATTACTGTGCAGGATC

GAGATACGATGCTATGGACTTCTGGGGTCAAGGAACCTCAGTCACCGTCTCCTCA

Amino acid sequence of the light chain variable region:

(SEQ ID NO: 64)

QIVLTQSPAIMSASPGEKVTMTCSASSIISYMHWYQQKSGTSPKRWIYDTSKLASGVPAR

FSGSGSGTSYSLTISGMEAEDAATYYCHQWTSNPLTFGGGTKLELK

Nucleic acid sequence of the light chain variable region:

(SEQ ID NO: 80)

CAAATTGTTCTCACCCAGTCTCCAGCAATCATGTCTGCATCTCCAGGGGAGAAGGTC

ACCATGACCTGCAGTGCCAGCTCAATTATAAGTTACATGCACTGGTACCAGCAGAAGTCA

GGCACCTCCCCCAAAAGATGGATTTATGACACTTCCAAACTGGCTTCTGGAGTCCCTGCTC

GCTTCAGTGGCAGTGGGTCTGGGACCTCTTACTCTCTCACAATCAGTGGCATGGAGGCTG

AAGATGCTGCCACTTATTACTGCCACCAGTGGACTAGTAACCCGCTCACGTTCGGTGGTG

GGACCAAGCTGGAACTGAAA

The CDRs defined by the Kabat and IMGT systems were obtained after sequence analysis. The following table (Table 7) lists the CDRs of the eight anti-TrkA antibodies defined on the basis of the Kabat and IMGT systems.

TABLE 7

| Anti-TrkA antibody CDRs defined according to Kabat and IMGT systems | | | | | | |
|---|---|---|---|---|---|---|
| Monoclonal antibody heavy chain CDRs: CDRs defined according to Kabat system are shown in black and bold; CDRs defined by IMGT are underlined. | | | | | | |
| Clone No. | CDR-H1 | SEQ ID No. | CDR-H2 | SEQ ID No. | CDR-H3 | SEQ ID No. |
| 5A3 | GYTFSRYWIE | 1 | EILPGRGVTNY NENFKG | 2 | ARSNYGDYDF | 3 |
| 11G8 | GYTFTSYWMH | 4 | EINPNNGLTNY DEKFKT | 5 | AKYGNYVAFAF | 6 |
| 26E9 | GYTFTNYWMH | 7 | EIYPSNGRTNY NEKFKN | 8 | ARSRYDPMED | 9 |
| 33H5 | GYTFTSYWIH | 10 | EINPNNGLTNYI EKFKN | 11 | AKYGNYVAFAY | 12 |
| 40D6 | GYTFSRYWIE | 13 | EILPGRSSTNY NEKFKG | 14 | TRVSQLHIYFDY | 15 |
| 42F5 | GYTFTNYWMH | 16 | EIYPNNGRVNY NEKFKN | 17 | ARSRYDPMED | 18 |
| 42H6 | GYTFTSYWMH | 19 | EIYSSNGLTNY NEKFKN | 20 | ARHWYVFLDH | 21 |
| 42A11 | GYTFTNYWMH | 22 | EIYPSNGRTNY NEKFKT | 23 | AGSRYDAMDF | 24 |
| Monoclonal antibody light chain CDRs: CDRs defined according to Kabat system are shown in black and bold; CDRs defined by IMGT are underlined. | | | | | | |
| Clone No. | CDR-L1 | SEQ ID No. | CDR-L2 | SEQ ID No. | CDR-L3 | SEQ ID No. |
| 5A3 | RSSSGAVTTSN HAN | 25 | GTNNRAP | 26 | ALWYSNHWV | 27 |
| 11G8 | RASENIYSYVA | 28 | NAKTLAE | 29 | QHHYGIPLT | 30 |
| 26E9 | SASSSVGYMH | 31 | DTSKLAS | 32 | QQWSSIPLT | 33 |

TABLE 7-continued

| Anti-TrkA antibody CDRs defined according to Kabat and IMGT systems | | | | | | |
|---|---|---|---|---|---|---|
| 33H5 | RASENIYTYLA | 34 | NTKTLAE | 35 | QHHYGVPLT | 36 |
| 40D6 | RSSKSLLHSNG NTYLY | 37 | RMSNLAS | 38 | MQHLEFPLT | 39 |
| 42F5 | SASSSVGYMH | 40 | DTSKLAS | 41 | QQWSSIPLT | 42 |
| 42H6 | RSSTGAVTTSN HAN | 43 | GINNRAP | 44 | ALWYSNHWV | 45 |
| 42A11 | SASSIISYMH | 46 | DTSKLAS | 47 | HQWTSNPLT | 48 |

Example 10: Humanization and Characterization of Murine Anti-TrkA Antibodies Humanization of Antibodies The light chain variable region (VL) and heavy chain variable region (VH) sequences of the antibodies secreted by the hybridoma cells obtained above were humanized. The amino acid sequences of murine antibody VL and VH were aligned and searched in the human embryonic antibody amino acid sequence database, to find human IGHV and IGKV sequences with high homology as humanization templates. The potential steric hindrance and interaction between the amino acids of the variable regions and the framework regions were analyzed by computer simulation technology, to determine the amino acids in the framework regions that are critical for maintaining the activity of the humanized antibodies. Such amino acids were retained during the humanization process. Humanization of the light and heavy chain variable regions was accomplished by CDR grafting technology. Then, the following humanized antibodies were obtained by using the selected antibody constant region templates.

The following exemplary antibodies were obtained after the humanization of the anti-TrkA antibody 42F5: 42F5-01, 42F5-03, 42F5-04, 42F5-05, 43F5-08 and 42F5-11. The humanized antibodies 42F5-01 and 42F5-03 were obtained with human IGHV1-2 as the heavy chain variable region template and human IGKV1-39 as the light chain variable region template; the humanized antibody 42F5-05 was obtained with human IGHV1-2 as the heavy chain variable region template and human IGKV1-6 as the light chain variable region template; the humanized antibody 42F5-11 was obtained with human IGHV1-2 as the heavy chain variable region and human IGKV3-11 as the light chain variable region template; the humanized antibody 42F5-04 was obtained with human IGHV1-69 as the heavy chain variable region template and human IGKV1-39 as the light chain variable region template; the humanized antibody 42F5-08 was obtained with human IGHV1-69 as the heavy chain variable region template and human IGKV1-6 as the light chain variable region template. Among the obtained humanized antibodies, the heavy chain variable region sequence of 42F5-01 is identical to that of 42F5-05, the heavy chain variable region sequence of the humanized antibody 42F5-03 is identical to that of 42F5-11, and the heavy chain variable region sequence of the humanized antibody 42F5-04 is identical to that of 42F5-08; the light chain variable region sequence of the humanized antibody 42F5-03 is identical to that of 42F5-04.

IGHV1-2, IGHV1-69, IGKV1-39, IGKV1-6 and IGKV3-11 are human germline IgG gene based on the human immunoglobulin gene database IMGT (The International ImMunoGeneTics Information System) and NCBI (The National Center for Biotechnology Information). In addition, since the antibody 42F5 comprises deamidation site NG in the heavy chain complementarity determining region sequences, the heavy chain variable regions of the humanized antibody 43F5-01 were further engineered in order to remove the potential impact of the site on the antibody. 42F5-01 was used as a template, the $NG_{55-56}$ in the heavy chain variable region was mutated to $SG_{55-56}$ or $QG_{55-56}$ or $NA_{55-56}$, respectively, resulting in humanized antibodies 42F5-13, 42F5-14 and 42F5-15.

For gene synthesis, the obtained humanized antibody heavy chain variable region sequence was grafted to the human IgG4 heavy chain constant region, and the light chain variable region sequence was grafted to the human Kappa light chain constant region. After enzymatic digestion, the fragments were ligated into the corresponding plasmids. The constructed plasmid was transiently transfected into CHO cells for expression. After 7-10 days of expression, the cell culture supernatant was purified with Mab Select column (GE Healthcare) pre-equilibrated with a corresponding buffer (such as phosphate buffered saline (pH 7.4)), and then eluted with sodium citrate or other buffers. The resulting antibodies were identified by SDS-PAGE or SEC-HPLC to determine purity and for subsequent characterizations.

Variable Region Sequences of the Humanized Antibodies of Anti-TrkA Antibody 42F5

The variable region sequences of the humanized anti-TrkA antibody 42F5: 42F5-01, 42F5-03, 42F5-04, 42F5-05, 42F5-08, 42F5-11, 42F5-13, 42F5-14 and 42F5-15 are as follows:

42F5-01:
Amino acid sequence of the heavy chain variable region:

(SEQ ID NO. 81)

QVQLVQSGAEVKKPGASVKVSCKSSGYTFTNYWMHWVRQAPGQGLEWMGEIYPNNG

RVNYNEKFKNRVTMTVDISISTAYMELSRLRSDDTAVYYCARSRYDPMEDWGQGTTVTVSS

Nucleic acid sequence of the heavy chain variable region:
(SEQ ID NO. 82)
CAGGTGCAGCTGGTGCAGAGCGGAGCTGAGGTGAAGAAGCCAGGAGCTTCCGTGA

AGGTGAGCTGCAAGTCCAGCGGCTACACCTTCACAAACTATTGGATGCACTGGGTGAGGC

AGGCTCCAGGACAGGGACTGGAGTGGATGGGCGAGATCTACCCTAACAATGGCAGGGTG

AACTACAACGAGAAGTTTAAGAACAGAGTGACCATGACAGTGGACATCAGCATCTCTACC

GCTTACATGGAGCTGTCTAGGCTGCGGTCCGACGATACAGCCGTGTACTATTGTGCTAGAT

CTCGCTATGACCCCATGGAGGATTGGGGCCAGGGCACCACAGTGACCGTGTCTTCC

Amino acid sequence of the light chain variable region:
(SEQ ID NO. 83)
DVQLTQSPSSLSASVGDRVTITCSASSSVGYMHWYQQKPGKAPKRLIYDTSKLASGVPS

RFSGSGSGTDYTLTISSLQPEDFATYFCQQWSSIPLTFGQGTRLEIK

Nucleic acid sequence of the light chain variable region:
(SEQ ID NO. 84)
GACGTGCAGCTGACCCAGTCTCCTTCCAGCCTGTCCGCCAGCGTGGGCGATAGAGTG

ACCATCACATGCTCCGCTTCTTCCAGCGTGGGCTACATGCACTGGTATCAGCAGAAGCCCG

GCAAGGCCCCTAAGAGGCTGATCTACGACACATCTAAGCTGGCTTCCGGAGTGCCAAGCC

GGTTCTCTGGCTCCGGCAGCGGAACCGACTACACCCTGACAATCTCTTCCCTGCAGCCAG

AGGATTTCGCCACATATTTTTGTCAGCAGTGGAGCTCTATCCCCCTGACCTTTGGCCAGGG

CACACGCCTGGAGATCAAG

42F5-03:
Amino acid sequence of the heavy chain variable region:
(SEQ ID NO. 85)
QVQLVQSGAEVKKPGASVKVSCKSSGYTFTNYWMHWVRQAPGQGLEWIGEIYPNNGR

VNYNEKFKNRATLTVDISISTAYMELSRLRSDDTAVYYCARSRYDPMEDWGQGTTVTVSS

Nucleic acid sequence of the heavy chain variable region:
(SEQ ID NO. 86)
CAGGTGCAGCTGGTGCAGAGCGGAGCTGAGGTGAAGAAGCCAGGAGCTTCCGTGA

AGGTGAGCTGCAAGTCCAGCGGCTACACCTTCACAAACTATTGGATGCACTGGGTGAGGC

AGGCTCCAGGACAGGGACTGGAGTGGATCGGCGAGATCTACCCTAACAATGGCAGGGTG

AACTACAACGAGAAGTTTAAGAACAGAGCCACCCTGACAGTGGACATCAGCATCTCTACC

GCTTACATGGAGCTGTCTAGGCTGCGGTCCGACGATACAGCCGTGTACTATTGTGCTAGAT

CTCGCTATGACCCCATGGAGGATTGGGGCCAGGGCACCACAGTGACCGTGTCTTCC

Amino acid sequence of the light chain variable region:
(SEQ ID NO. 87)
DVQLTQSPSSLSASVGDRVTITCSASSSVGYMHWYQQKPGKAPKRWIYDTSKLASGVPS

RFSGSGSGTDYTLTISSLQPEDFATYFCQQWSSIPLTFGQGTRLEIK

Nucleic acid sequence of the light chain variable region:
(SEQ ID NO. 88)
GACGTGCAGCTGACCCAGTCTCCTTCCAGCCTGTCCGCCAGCGTGGGCGATAGAGTG

ACCATCACATGCTCCGCTTCTTCCAGCGTGGGCTACATGCACTGGTATCAGCAGAAGCCCG

GCAAGGCCCCTAAGAGGTGGATCTACGACACATCTAAGCTGGCTTCCGGAGTGCCAAGCC

GGTTCTCTGGCTCCGGCAGCGGAACCGACTACACCCTGACAATCTCTTCCCTGCAGCCAG

AGGATTTCGCCACATATTTTTGTCAGCAGTGGAGCTCTATCCCCCTGACCTTTGGCCAGGG

CACACGCCTGGAGATCAAG

42F5-04:
Amino acid sequence of the heavy chain variable region:
                                                      (SEQ ID NO. 89)
QVQLVQSGAEVKKPGSSVKVSCKSSGYTFTNYWMHWVRQAPGQGLEWIGEIYPNNGR

VNYNEKFKNRATLTVDISTSTAYMELSSLRSEDTAVYYCARSRYDPMEDWGQGTTVTVSS

Nucleic acid sequence of the heavy chain variable region:
                                                      (SEQ ID NO. 90)
CAGGTGCAGCTGGTGCAGTCCGGAGCTGAGGTGAAGAAGCCAGGCTCCAGCGTGAA

GGTGAGCTGCAAGTCTTCCGGCTACACCTTCACAAACTATTGGATGCACTGGGTGAGGCA

GGCTCCAGGACAGGGACTGGAGTGGATCGGCGAGATCTACCCTAACAATGGCAGAGTGA

ACTACAACGAGAAGTTTAAGAACCGCGCCACCCTGACAGTGGACATCTCTACCTCCACAG

CTTACATGGAGCTGAGCTCTCTGAGAAGCGAGGATACCGCCGTGTACTATTGTGCTAGGTC

TCGGTATGACCCCATGGAGGATTGGGGCCAGGGCACCACAGTGACAGTGTCCAGC

Amino acid sequence of the light chain variable region:
                                                      (SEQ ID NO. 87)
Identical to that of 42F5-03

Nucleic acid sequence of the light chain variable region:
                                                      (SEQ ID NO. 88)
Identical to that of 42F5-03

42F5-05:
Amino acid sequence of the heavy chain variable region:
                                                      (SEQ ID NO. 81)
Identical to that of 42F5-01

Nucleic acid sequence of the heavy chain variable region:
                                                      (SEQ ID NO. 82)
Identical to that of 42F5-01

Amino acid sequence of the light chain variable region:
                                                      (SEQ ID NO. 91)
QVQLTQSPSSLSASVGDRVTITCSASSSVGYMHWYQQKPGKAPKRLIYDTSKLASGVPS

RFSGSGSGTDYTLTISSLQPEDFATYFCQQWSSIPLTFGQGTRLEIK

Nucleic acid sequence of the light chain variable region:
                                                      (SEQ ID NO. 92)
CAGGTGCAGCTGACCCAGTCTCCTTCCAGCCTGTCCGCCAGCGTGGGCGACAGAGT

GACCATCACATGCTCCGCTTCTTCCAGCGTGGGCTACATGCACTGGTATCAGCAGAAGCCC

GGCAAGGCCCCTAAGAGGCTGATCTACGATACATCTAAGCTGGCTTCCGGAGTGCCAAGC

CGGTTCTCTGGCTCCGGCAGCGGAACCGACTACACCCTGACAATCTCTTCCCTGCAGCCA

GAGGATTTCGCCACATATTTTTGTCAGCAGTGGAGCTCTATCCCCCTGACCTTTGGCCAGG

GCACACGCCTGGAGATCAAG

42F5-08
Amino acid sequence of the heavy chain variable region:
                                                      (SEQ ID NO. 89)
Identical to that of 42F5-04

Nucleic acid sequence of the heavy chain variable region:
                                                      (SEQ ID NO. 90)
Identical to that of 42F5-04

Amino acid sequence of the light chain variable region:
                                                      (SEQ ID NO. 93)
RFSGSGSGTDYTLTISSLQPEDFATYFCQQWSSIPLTFGQGTRLEIK Nucleic acid sequence of the light chain variable region:
                                                      (SEQ ID NO. 94)
CAGGTGCAGCTGACCCAGTCTCCTTCCAGCCTGTCCGCCAGCGTGGGCGACAGAGT

GACCATCACATGCTCCGCTTCTTCCAGCGTGGGCTACATGCACTGGTATCAGCAGAAGCCC

GGCAAGGCCCCTAAGAGGTGGATCTACGATACATCTAAGCTGGCTTCCGGAGTGCCAAGC

CGGTTCTCTGGCTCCGGCAGCGGAACCGACTACACCCTGACAATCTCTTCCCTGCAGCCA

GAGGATTTCGCCACATATTTTTGTCAGCAGTGGAGCTCTATCCCCCTGACCTTTGGCCAGG

GCACACGCCTGGAGATCAAG

42F5-11:
Amino acid sequence of the heavy chain variable region:
                                              (SEQ ID NO. 85)
Identical to that of 42F5-03

Nucleic acid sequence of the heavy chain variable region:
                                              (SEQ ID NO. 86)
Identical to that of 42F5-03

Amino acid sequence of the light chain variable region:
                                              (SEQ ID NO. 95)
EVVLTQSPATLSLSPGERATLSCSASSSVGYMHWYQQKPGQAPRRWIYDTSKLASGVPA

RFSGSGSGTDYTLTISSLEPEDAAVYFCQQWSSIPLTFGQGTRLEIK

Nucleic acid sequence of the light chain variable region:
                                              (SEQ ID NO. 96)
GAGGTGGTGCTGACCCAGTCCCCAGCCACACTGAGCCTGTCTCCAGGAGAGAGAGC

CACCCTGTCCTGCTCCGCCTCCAGCTCTGTGGGCTACATGCACTGGTATCAGCAGAAGCC

AGGACAGGCTCCTAGGCGGTGGATCTACGACACCTCTAAGCTGGCTTCCGGAGTGCCAGC

TCGCTTCTCTGGCTCCGGCAGCGGCACAGACTACACCCTGACAATCTCCAGCCTGGAGCC

TGAGGATGCCGCCGTGTACTTCTGTCAGCAGTGGTCTTCCATCCCACTGACCTTTGGCCAG

GGCACAAGGCTGGAGATCAAG

42F5-13:
Amino acid sequence of the heavy chain variable region:
                                              (SEQ ID NO. 97)
QVQLVQSGAEVKKPGASVKVSCKSSGYTFTNYWMHWVRQAPGQGLEWMGEIYPNSG

RVNYNEKFKNRVTMTVDISISTAYMELSRLRSDDTAVYYCARSRYDPMEDWGQGTTVTVSS

Nucleic acid sequence of the heavy chain variable region:
                                              (SEQ ID NO. 98)
CAGGTGCAGCTGGTGCAGTCCGGCGCCGAGGTGAAGAAGCCCGGCGCTTCTGTGAA

GGTGAGCTGCAAGAGCTCCGGCTACACCTTTACCAATTATTGGATGCACTGGGTGAGGCA

GGCTCCCGGCCAGGGACTGGAGTGGATGGGCGAGATATATCCCAATAGCGGCCGGGTGAA

TTATAATGAGAAGTTTAAGAATCGGGTGACCATGACCGTGGATATCAGCATCTCCACCGCC

TACATGGAGCTGAGCAGGCTGAGGAGCGATGACACCGCTGTGTACTACTGCGCTAGGTCC

AGGTATGACCCCATGGAGGATTGGGGCCAGGGCACCACCGTGACCGTGAGCAGC

Amino acid sequence of the light chain variable region:
                                              (SEQ ID NO. 83)
Identical to that of 42F5-01

Nucleic acid sequence of the light chain variable region:
                                              (SEQ ID NO. 84)
Identical to that of 42F5-01

42F5-14:
Amino acid sequence of the heavy chain variable region:
                                              (SEQ ID NO. 99)
QVQLVQSGAEVKKPGASVKVSCKSSGYTFTNYWMHWVRQAPGQGLEWMGEIYPNQG

RVNYNEKFKNRVTMTVDISISTAYMELSRLRSDDTAVYYCARSRYDPMEDWGQGTTVTVSS

Nucleic acid sequence of the heavy chain variable region:
                                              (SEQ ID NO. 100)
CAGGTGCAGCTGGTGCAGAGCGGCGCCGAGGTGAAGAAGCCCGGCGCTTCCGTGAA

GGTGTCCTGTAAGTCCAGCGGCTATACCTTCACCAACTATTGGATGCACTGGGTGAGGCA

GGCCCCTGGCCAGGGACTGGAGTGGATGGGCGAGATATATCCTAACCAGGGCCGGGTGA

ATTATAACGAGAAGTTCAAGAATAGGGTGACCATGACCGTGGACATCTCCATCAGCACCG

CTTACATGGAGCTGTCCAGGCTGCGGAGCGACGATACCGCCGTGTACTACTGTGCCAGGT

-continued

```
CCCGGTATGATCCCATGGAGGACTGGGGCCAGGGCACCACCGTGACCGTGAGCAGC
```

Amino acid sequence of the light chain variable region:
                                                (SEQ ID NO. 83)
Identical to that of 42F5-01

Nucleic acid sequence of the light chain variable region:
                                                (SEQ ID NO. 84)
Identical to that of 42F5-01

42F5-15:
Amino acid sequence of the heavy chain variable region:
                                                (SEQ ID NO. 101)
```
QVQLVQSGAEVKKPGASVKVSCKSSGYTFTNYWMHWVRQAPGQGLEWMGEIYPNNA

RVNYNEKFKNRVTMTVDISISTAYMELSRLRSDDTAVYYCARSRYDPMEDWGQGTTVTVSS
```

Nucleic acid sequence of the heavy chain variable region:
                                                (SEQ ID NO. 102)
```
CAGGTGCAGCTGGTGCAGTCCGGCGCCGAGGTGAAGAAGCCCGGCGCTTCTGTGAA

GGTGTCCTGTAAGAGCAGCGGCTACACCTTTACCAATTATTGGATGCACTGGGTGAGGCA

GGCCCCCGGCCAGGGATTGGAGTGGATGGGCGAGATATATCCTAACAATGCCAGGGTGAA

CTATAATGAGAAGTTTAAGAACCGGGTGACCATGACCGTGGACATCAGCATCTCCACCGC

CTATATGGAGCTGAGCCGGCTGCGGTCCGACGACACCGCTGTGTACTACTGCGCCCGGTC

CCGGTATGATCCTATGGAGGACTGGGGCCAGGGCACCACCGTGACCGTGAGCTCC
```

Amino acid sequence of the light chain variable region:
                                                (SEQ ID NO. 83)
Identical to that of 42F5-01

Nucleic acid sequence of the light chain variable region:
                                                (SEQ ID NO. 84)
Identical to that of 42F5-01

TABLE 8

Variable region sequences of the humanized antibodies of anti-TrkA antibody 42F5

| | Heavy chain | | Light chain | |
|---|---|---|---|---|
| Antibody number | Amino acid sequence of the heavy chain: | Nucleic acid sequence of the heavy chain: | Amino acid sequence of the light chain: | Nucleic acid sequence of the light chain: |
| 42F5-01 | SEQ ID NO. 81 | SEQ ID NO. 82 | SEQ ID NO. 83 | SEQ ID NO. 84 |
| 42F5-03 | SEQ ID NO. 85 | SEQ ID NO. 86 | SEQ ID NO. 87 | SEQ ID NO. 88 |
| 42F5-04 | SEQ ID NO. 89 | SEQ ID NO. 90 | SEQ ID NO. 87 | SEQ ID NO. 88 |
| 42F5-05 | SEQ ID NO. 81 | SEQ ID NO. 82 | SEQ ID NO. 91 | SEQ ID NO. 92 |
| 42F5-08 | SEQ ID NO. 89 | SEQ ID NO. 90 | SEQ ID NO. 93 | SEQ ID NO. 94 |
| 42F5-11 | SEQ ID NO. 85 | SEQ ID NO. 86 | SEQ ID NO. 95 | SEQ ID NO. 96 |
| 42F5-13 | SEQ ID NO. 97 | SEQ ID NO. 98 | SEQ ID NO. 83 | SEQ ID NO. 84 |
| 42F5-14 | SEQ ID NO. 99 | SEQ ID NO. 100 | SEQ ID NO. 83 | SEQ ID NO. 84 |
| 42F5-15 | SEQ ID NO. 101 | SEQ ID NO. 102 | SEQ ID NO. 83 | SEQ ID NO. 84 |

B. Characterization of Humanized Anti-TrkA Antibodies
1) The Binding of Humanized Antibodies to Human TrkA The affinities of humanized antibodies of anti-TrkA antibody 42F5 were studied with human TrkA extracellular region (33-417) protein containing mouse Fc. Each well of a 96-well microtiter plate was coated with 50 ng of human TrkA, washed and blocked, then added with serially diluted humanized antibodies, and incubated for 1 hour at room temperature. After washing three times, horseradish peroxidase-conjugated goat anti-human IgG antibody (ThermoFisher, A18817) was added and reacted at room temperature for 1 hour. After washing three time, tetramethylbenzidine (TMB, Biolegend) was added for color development. 1M HCl was used to terminate the color development, and the absorbance values were read at 450 nm with a microplate reader.

Figure 17:
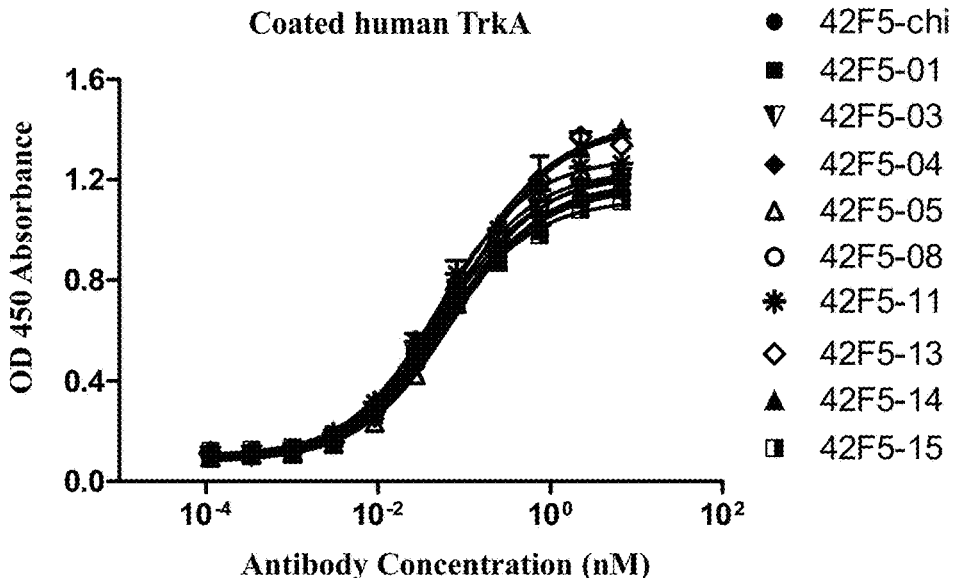
FIG. 17 shows the ELISA results of the binding of the humanized anti-TrkA antibodies of the present invention to human TrkA.

The binding results are shown in Table 9 and FIG. 17. All the humanized antibodies of anti-TrkA antibody 42F5 with different sequences have similar binding to human TrkA, and the level of binding is comparable to that of human-mouse chimeric antibody 42F5-Chi (which contains variable regions of murine anti-TrkA antibody 42F5 and constant regions of human antibody).

TABLE 9

| EC50 values of humanized antibodies of anti-TrkA antibody 42F5 binding to TrkA | | | | | | | | | |
|---|---|---|---|---|---|---|---|---|---|
| Antibodies | 42F5-Chi | 42F5-01 | 42F5-03 | 42F5-04 | 42F5-05 | 42F5-08 | 42F5-11 | 42F5-13 | 42F5-14 | 42F5-15 |
| EC50 (nM) | 0.062 | 0.061 | 0.056 | 0.070 | 0.072 | 0.055 | 0.050 | 0.087 | 0.071 | 0.054 |

2) The Binding of Humanized Antibodies to Cells Expressing TrkA/TrkB/TrkC

The specificities of the humanized antibodies of anti-TrkA antibody 42F5 were studied by using cell lines TrkA/CHO (ThermoFisher, K1516), TrkB/CHO (ThermoFisher, K1491) and TrkC/CHO (ThermoFisher, K1515) expressing TrkA, TrkB, and TrkC respectively. CHO-K1 was used as a negative control. The binding of the humanized antibodies to the four cell lines was detected by flow cytometry.

The cells were cultured according to the manufacturer's instruction. The cells were harvested in the logarithmic growth phase, re-suspended in flow buffer (PBS+2% FBS, pH 7.4), and added into 96-well plate, $10^5$ cells per well (50 µl). 50 µl of 100 µg/mL humanized anti-TrkA antibody was added, incubated at room temperature for 60 min, and centrifuged at 1200 rpm. The supernatant was discarded and the cells were washed 3 times. FITC-labeled goat anti-human Fc antibody (Abeam, ab97224) was diluted to 5 µg/mL with flow buffer and used to re-suspend the cells, incubated at room temperature for 30 min in the dark, centrifuged, and the supernatant was discarded. After washing 3 times, the cells were re-suspended with 7AAD solution (Biolegend, 420403), incubated for 10 min at room temperature, and the binding of the antibody was detected with a flow cytometer (BioRad, ZE5).

Figure 18:
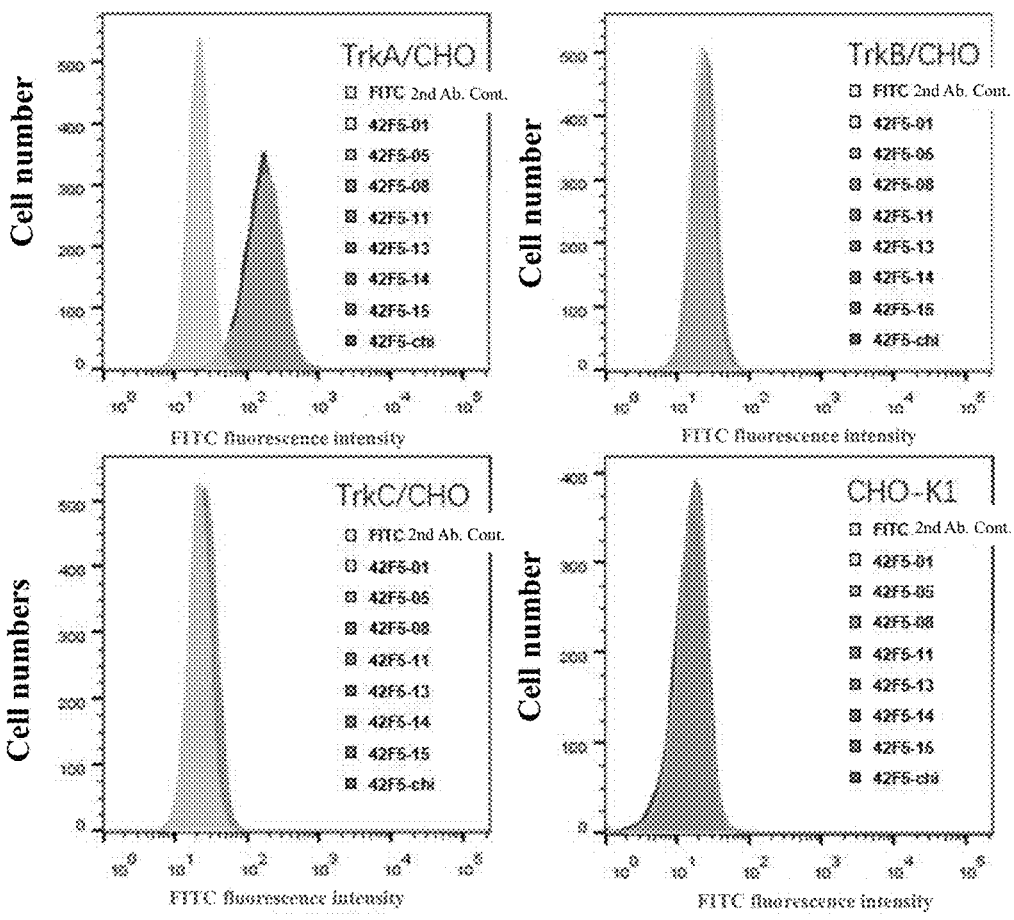
FIG. 18 shows the FACS results of the binding of the humanized anti-TrkA antibodies of the present invention to CHO cells expressing human TrkA, TrkB or TrkC protein.

The results are shown in FIG. 18. Similar to the human-mouse chimeric antibody 42F5-Chi, the humanized antibodies of anti-TrkA antibody 42F5 bind to TrkA/CHO cells, but do not bind to TrkB/CHO, TrkC/CHO or CHO-K1 cells, indicating that the humanized anti-TrkA antibodies have favorable specificities.

Figure 19:
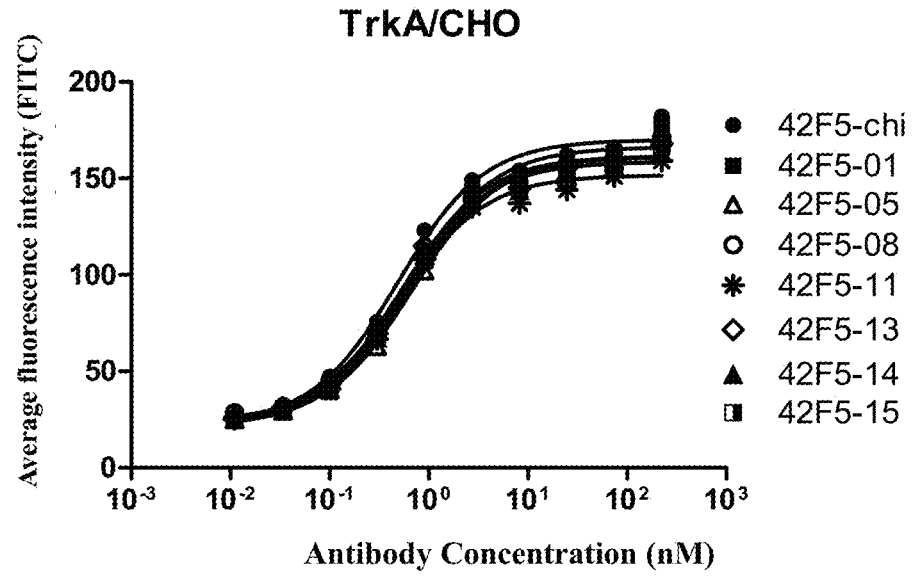
FIG. 19 shows the results of the binding of the humanized anti-TrkA antibodies of the present invention to CHO cells expressing human TrkA protein.

The binding curve of the humanized anti-TrkA antibodies and TrkA/CHO cells was detected with the same flow cytometry. The antibodies were diluted 3-fold from a concentration of 66.67 µg/mL for a total of 10 concentrations. The results are shown in FIG. 19. The humanized antibodies of anti-TrkA antibody 42F5 bind to TrkA/CHO cells at a level comparable to the human-mouse chimeric antibody 42F5-Chi. The EC50 values are summarized in Table 10.

TABLE 10

| EC50 values of the humanized antibodies of anti-TrkA antibody 42F5 binding to TrkA (nM) | | | | | | | |
|---|---|---|---|---|---|---|---|
| Antibodies | 42F5-chi | 42F5-01 | 42F5-05 | 42F5-08 | 42F5-11 | 42F5-13 | 42F5-14 | 42F5-15 |
| EC50 (nM) | 0.490 | 0.605 | 0.680 | 0.535 | 0.513 | 0.518 | 0.547 | 0.609 |

3) Assay of TF-1 Cell Proliferation Induced by NGF

Figure 20:
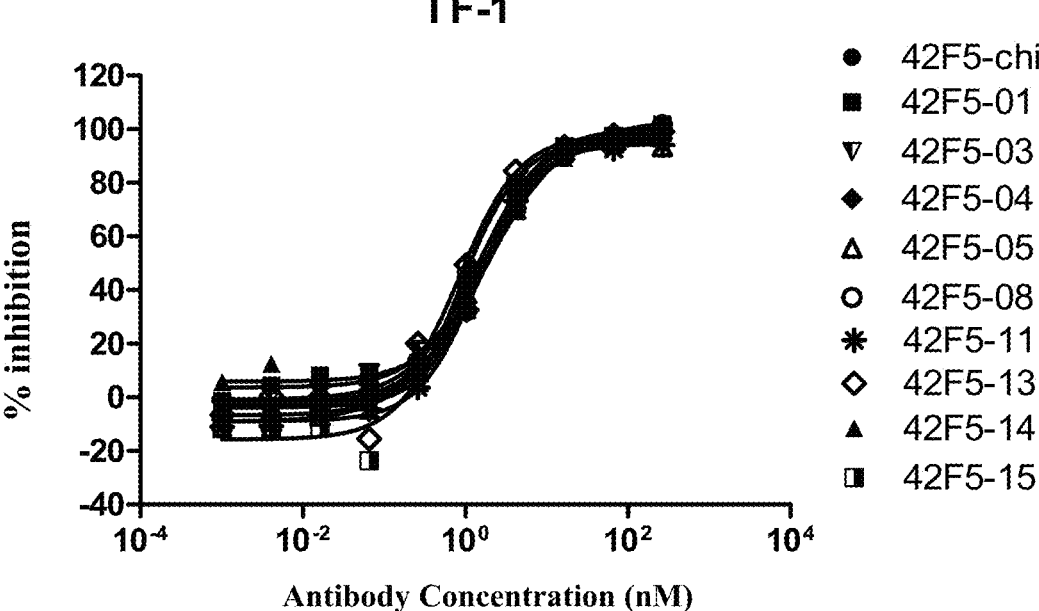
FIG. 20 shows efficiencies of the humanized anti-TrkA antibodies of the present invention to inhibit NGF-induced TF-1 cell proliferation.

The effects of the humanized antibodies of anti-TrkA antibody 42F5 on inhibiting the NGF/TrkA pathway were detected by TF-1 cell proliferation as described in Example 6A. The results are shown in FIG. 20, all the humanized antibodies of anti-TrkA antibody 42F5 can inhibit the proliferation of TF-1 cells induced by NGF, and inhibitory levels are comparable to that of the human-mouse chimeric antibody 42F5-Chi. The IC50 values are shown in Table 11.

TABLE 11

| IC50 values of the humanized antibodies of anti-TrkA antibody 42F5 inhibiting NGF-induced TF-1 cell proliferation | | | | | | | | | |
|---|---|---|---|---|---|---|---|---|---|
| Antibodies | 42F5-chi | 42F5-01 | 42F5-03 | 42F5-04 | 42F5-05 | 42F5-08 | 42F5-11 | 42F5-13 | 42F5-14 | 42F5-15 |
| IC50 (nM) | 1.547 | 1.566 | 1.431 | 1.691 | 1.483 | 1.649 | 1.404 | 0.867 | 1.940 | 0.850 |

4) Assay of NGF-Induced TrkA/Ba/F3 Cell Proliferation

Figure 21:
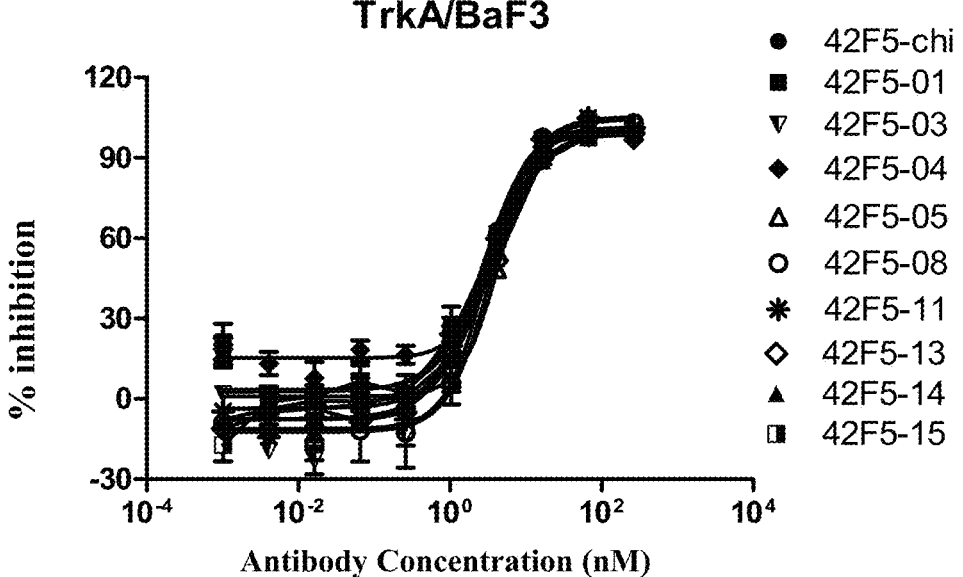
FIG. 21 shows efficiencies of the humanized anti-TrkA antibodies of the present invention to inhibit NGF-induced TrkA/Ba/F3 cell proliferation.

The effects of the humanized antibodies of anti-TrkA antibody 42F5 on inhibiting the NGF/TrkA pathway were detected by TrkA/Ba/F3 proliferation as described in Example 6B. The results are shown in FIG. 21, all the humanized anti-TrkA antibodies can inhibit the proliferation of TrkA/Ba/F3 cells induced by NGF, and inhibitory levels are comparable to that of the human-mouse chimeric antibody 42F5-Chi. The IC50 values are shown in Table 12.

TABLE 12

IC50 values of the humanized antibodies of anti-TrkA antibody 42F5 inhibiting NGF-
induced TrkA/Ba/F3 cell proliferation

| Antibodies | 42F5-chi | 42F5-01 | 42F5-03 | 42F5-04 | 42F5-05 | 42F5-08 | 42F5-11 | 42F5-13 | 42F5-14 | 42F5-15 |
|---|---|---|---|---|---|---|---|---|---|---|
| IC50 (nM) | 2.916 | 2.966 | 2.91 | 3.695 | 4.417 | 3.541 | 2.814 | 3.309 | 3.273 | 2.71 |

While specific embodiments of the present invention have been illustrated and described in detail, it should be appreciated that the present invention is not intended to be limited to the specific embodiments described.

---

What is claimed is:

1. An antibody or antigen-binding fragment thereof capable of specifically binding to TrkA, the antibody or antigen-binding fragment thereof comprising a heavy chain variable region VH and a light chain variable region VL:

the VH of the antibody or antigen-binding fragment thereof comprises: VH CDR1 as shown in SEQ ID NO: 1, VH CDR2 as shown in SEQ ID NO: 2, and VH CDR3 as shown in SEQ ID NO: 3; and the VL of the antibody or antigen-binding fragment thereof comprises: VL CDR1 as shown in SEQ ID NO: 25, VL CDR2 as shown in SEQ ID NO: 26, and VL CDR3 as shown in SEQ ID NO: 27; or the VH of the antibody or antigen-binding fragment thereof comprises: VH CDR1 as shown in SEQ ID NO: 4, VH CDR2 as shown in SEQ ID NO: 5, and VH CDR3 as shown in SEQ ID NO: 6; and the VL of the antibody or antigen-binding fragment thereof comprises: VL CDR1 as shown in SEQ ID NO: 28, VL CDR2 as shown in SEQ ID NO: 29, and VL CDR3 as shown in SEQ ID NO: 30; or the VH of the antibody or antigen-binding fragment thereof comprises: VH CDR1 as shown in SEQ ID NO: 7, VH CDR2 as shown in SEQ ID NO: 8, and VH CDR3 as shown in SEQ ID NO: 9; and the VL of the antibody or antigen-binding fragment thereof comprises: VL CDR1 as shown in SEQ ID NO: 31, VL CDR2 as shown in SEQ ID NO: 32, and VL CDR3 as shown in SEQ ID NO: 33; or the VH of the antibody or antigen-binding fragment thereof comprises: VH CDR1 as shown in SEQ ID NO: 10, VH CDR2 as shown in SEQ ID NO: 11, and VH CDR3 as shown in SEQ ID NO: 12; and the VL of the antibody or antigen-binding fragment thereof comprises: VL CDR1 as shown in SEQ ID NO: 34, VL CDR2 as shown in SEQ ID NO: 35, and VL CDR3 as shown in SEQ ID NO: 36; or the VH of the antibody or antigen-binding fragment thereof comprises: VH CDR1 as shown in SEQ ID NO:13, VH CDR2 as shown in SEQ ID NO:14 and VH CDR3 as shown in SEQ ID NO: 15, and the VL of the antibody or antigen-binding fragment thereof comprises: VL CDR1 as shown in SEQ ID NO: 37, VL CDR2 as shown in SEQ ID NO: 38, and VL CDR3 as shown in SEQ ID NO: 39; or the VH of the antibody or antigen-binding fragment thereof comprises: VH CDR1 as shown in SEQ ID NO:16, VH CDR2 as shown in SEQ ID NO:17 and VH CDR3 as shown in SEQ ID NO: 18, and the VL of the antibody or antigen-binding fragment thereof comprises: VL CDR1 as shown in SEQ ID NO: 40, VL CDR2 as shown in SEQ ID NO: 41, and VL CDR3 as shown in SEQ ID NO: 42; or the VH of the antibody or antigen-binding fragment thereof comprises: VH CDR1 as shown in SEQ ID NO:19, VH CDR2 as shown in SEQ ID NO:20 and VH CDR3 as shown in SEQ ID NO: 21, and the VL of the antibody or antigen-binding fragment thereof comprises: VL CDR1 as shown in SEQ ID NO: 43, VL CDR2 as shown in SEQ ID NO: 44, and VL CDR3 as shown in SEQ ID NO: 45; or the VH of the antibody or antigen-binding fragment thereof comprises: VH CDR1 as shown in SEQ ID NO: 22, VH CDR2 as shown in SEQ ID NO: 23, and VH CDR3 as shown in SEQ ID NO: 24, and the VL of the antibody or antigen-binding fragment thereof comprises: VL CDR1 as shown in SEQ ID NO: 46, VL CDR2 as shown in SEQ ID NO: 47, and VL CDR3 as shown in SEQ ID NO: 48.

2. The antibody or antigen-binding fragment thereof according to claim 1, wherein:

the antibody or antigen-binding fragment thereof comprises: a VH having sequence as shown in SEQ ID NO:49 and a VL having sequence as shown in SEQ ID NO: 57; or the antibody or antigen-binding fragment thereof comprises: a VH having sequence as shown in SEQ ID NO: 50 and a VL having sequence as shown in SEQ ID NO: 58; or the antibody or antigen-binding fragment thereof comprises: a VH having sequence as shown in SEQ ID NO:51 and a VL having sequence as shown in SEQ ID NO: 59; or the antibody or antigen-binding fragment thereof comprises: a VH having sequence as shown in SEQ ID NO: 52 and a VL having sequence as shown in SEQ ID NO: 60; or the antibody or antigen-binding fragment thereof comprises: a VH having sequence as shown in SEQ ID NO: 53 and a VL having sequence as shown in SEQ ID NO: 61; or the antibody or antigen-binding fragment thereof comprises: a VH having sequence as shown in SEQ ID NO: 54 and a VL having sequence as shown in SEQ ID NO: 62; or the antibody or antigen-binding fragment thereof comprises: a VH having sequence as shown in SEQ ID NO: 55 and a VL having sequence as shown in SEQ ID NO: 63; or the antibody or antigen-binding fragment thereof comprises: a VH having sequence as shown in SEQ ID NO: 56 and a VL having sequence as shown in SEQ ID NO: 64.

3. The antibody or antigen-binding fragment thereof of claim 1, wherein the antibody or antigen-binding fragment thereof further comprises:

(a) a heavy chain constant region (CH) of human immunoglobulin; and (b) a light chain constant region (CL) of human immunoglobulin.

4. The antibody or antigen-binding fragment thereof according to claim 1, wherein the antigen-binding fragment is selected from Fab, Fab', (Fab')$_2$, Fv, disulfide-linked Fv, scFv, and diabody; and/or, the antibody is a murine antibody, chimeric antibody, humanized antibody, bispecific antibody or multispecific antibody.

5. A pharmaceutical composition, comprising the antibody or antigen-binding fragment thereof of claim 1, and a pharmaceutically acceptable carrier and/or excipient.

* * * * *

SEQUENCE LISTING

<160> NUMBER OF SEQ ID NOS: 102

<210> SEQ ID NO 1
<211> LENGTH: 10
<212> TYPE: PRT
<213> ORGANISM: Artificial Sequence
<220> FEATURE:
<223> OTHER INFORMATION: Synthesized

<400> SEQUENCE: 1

Gly Tyr Thr Phe Ser Arg Tyr Trp Ile Glu
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Synthesized

<400> SEQUENCE: 2

Glu Ile Leu Pro Gly Arg Gly Val Thr Asn Tyr Asn Glu Asn Phe Lys
1               5                   10                  15

Gly

<210> SEQ ID NO 3
<211> LENGTH: 10
<212> TYPE: PRT
<213> ORGANISM: Artificial Sequence
<220> FEATURE:
<223> OTHER INFORMATION: Synthesized

<400> SEQUENCE: 3

Ala Arg Ser Asn Tyr Gly Asp Tyr Asp Phe
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthesized

<400> SEQUENCE: 4

Gly Tyr Thr Phe Thr Ser Tyr Trp Met His
1               5                   10

<210> SEQ ID NO 5
<211> LENGTH: 17
<212> TYPE: PRT
<213> ORGANISM: Artificial Sequence
<220> FEATURE:
<223> OTHER INFORMATION: Synthesized -continued

```
<400> SEQUENCE: 5

Glu Ile Asn Pro Asn Asn Gly Leu Thr Asn Tyr Asp Glu Lys Phe Lys
1               5                   10                  15

Thr

<210> SEQ ID NO 6
<211> LENGTH: 11
<212> TYPE: PRT
<213> ORGANISM: Artificial Sequence
<220> FEATURE:
<223> OTHER INFORMATION: Synthesized

<400> SEQUENCE: 6

Ala Lys Tyr Gly Asn Tyr Val Ala Phe Ala Phe
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Synthesized

<400> SEQUENCE: 7

Gly Tyr Thr Phe Thr Asn Tyr Trp Met His
1               5                   10

<210> SEQ ID NO 8
<211> LENGTH: 17
<212> TYPE: PRT
<213> ORGANISM: Artificial Sequence
<220> FEATURE:
<223> OTHER INFORMATION: Synthesized

<400> SEQUENCE: 8

Glu Ile Tyr Pro Ser Asn Gly Arg Thr Asn Tyr Asn Glu Lys Phe Lys
1               5                   10                  15

Asn

<210> SEQ ID NO 9
<211> LENGTH: 10
<212> TYPE: PRT
<213> ORGANISM: Artificial Sequence
<220> FEATURE:
<223> OTHER INFORMATION: Synthesized

<400> SEQUENCE: 9

Ala Arg Ser Arg Tyr Asp Pro Met Glu Asp
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Synthesized

<400> SEQUENCE: 10

Gly Tyr Thr Phe Thr Ser Tyr Trp Ile His
1               5                   10

<210> SEQ ID NO 11
<211> LENGTH: 17
<212> TYPE: PRT
```

```
<213> ORGANISM: Artificial Sequence
<220> FEATURE:
<223> OTHER INFORMATION: Synthesized

<400> SEQUENCE: 11

Glu Ile Asn Pro Asn Asn Gly Leu Thr Asn Tyr Ile Glu Lys Phe Lys
1               5                   10                  15

Asn

<210> SEQ ID NO 12
<211> LENGTH: 11
<212> TYPE: PRT
<213> ORGANISM: Artificial Sequence
<220> FEATURE:
<223> OTHER INFORMATION: Synthesized

<400> SEQUENCE: 12

Ala Lys Tyr Gly Asn Tyr Val Ala Phe Ala Tyr
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Synthesized

<400> SEQUENCE: 13

Gly Tyr Thr Phe Ser Arg Tyr Trp Ile Glu
1               5                   10

<210> SEQ ID NO 14
<211> LENGTH: 17
<212> TYPE: PRT
<213> ORGANISM: Artificial Sequence
<220> FEATURE:
<223> OTHER INFORMATION: Synthesized

<400> SEQUENCE: 14

Glu Ile Leu Pro Gly Arg Ser Ser Thr Asn Tyr Asn Glu Lys Phe Lys
1               5                   10                  15

Gly

<210> SEQ ID NO 15
<211> LENGTH: 12
<212> TYPE: PRT
<213> ORGANISM: Artificial Sequence
<220> FEATURE:
<223> OTHER INFORMATION: Synthesized

<400> SEQUENCE: 15

Thr Arg Val Ser Gln Leu His Ile Tyr Phe Asp Tyr
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Synthesized

<400> SEQUENCE: 16

Gly Tyr Thr Phe Thr Asn Tyr Trp Met His
1               5                   10
```

```
<210> SEQ ID NO 17
<211> LENGTH: 17
<212> TYPE: PRT
<213> ORGANISM: Artificial Sequence
<220> FEATURE:
<223> OTHER INFORMATION: Synthesized

<400> SEQUENCE: 17

Glu Ile Tyr Pro Asn Asn Gly Arg Val Asn Tyr Asn Glu Lys Phe Lys
1               5                   10                  15

Asn

<210> SEQ ID NO 18
<211> LENGTH: 10
<212> TYPE: PRT
<213> ORGANISM: Artificial Sequence
<220> FEATURE:
<223> OTHER INFORMATION: Synthesized

<400> SEQUENCE: 18

Ala Arg Ser Arg Tyr Asp Pro Met Glu Asp
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Synthesized

<400> SEQUENCE: 19

Gly Tyr Thr Phe Thr Ser Tyr Trp Met His
1               5                   10

<210> SEQ ID NO 20
<211> LENGTH: 17
<212> TYPE: PRT
<213> ORGANISM: Artificial Sequence
<220> FEATURE:
<223> OTHER INFORMATION: Synthesized

<400> SEQUENCE: 20

Glu Ile Tyr Ser Ser Asn Gly Leu Thr Asn Tyr Asn Glu Lys Phe Lys
1               5                   10                  15

Asn

<210> SEQ ID NO 21
<211> LENGTH: 10
<212> TYPE: PRT
<213> ORGANISM: Artificial Sequence
<220> FEATURE:
<223> OTHER INFORMATION: Synthesized

<400> SEQUENCE: 21

Ala Arg His Trp Tyr Val Phe Leu Asp His
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Synthesized

<400> SEQUENCE: 22

Gly Tyr Thr Phe Thr Asn Tyr Trp Met His
```

```
1               5                    10
```

```
<210> SEQ ID NO 23
<211> LENGTH: 17
<212> TYPE: PRT
<213> ORGANISM: Artificial Sequence
<220> FEATURE:
<223> OTHER INFORMATION: Synthesized

<400> SEQUENCE: 23

Glu Ile Tyr Pro Ser Asn Gly Arg Thr Asn Tyr Asn Glu Lys Phe Lys
1               5                    10                   15

Thr
```

```
<210> SEQ ID NO 24
<211> LENGTH: 10
<212> TYPE: PRT
<213> ORGANISM: Artificial Sequence
<220> FEATURE:
<223> OTHER INFORMATION: Synthesized

<400> SEQUENCE: 24

Ala Gly Ser Arg Tyr Asp Ala Met Asp Phe
1               5                    10
```

```
<210> SEQ ID NO 25
<211> LENGTH: 14
<212> TYPE: PRT
<213> ORGANISM: Artificial Sequence
<220> FEATURE:
<223> OTHER INFORMATION: Synthesized

<400> SEQUENCE: 25

Arg Ser Ser Ser Gly Ala Val Thr Thr Ser Asn His Ala Asn
1               5                    10
```

```
<210> SEQ ID NO 26
<211> LENGTH: 7
<212> TYPE: PRT
<213> ORGANISM: Artificial Sequence
<220> FEATURE:
<223> OTHER INFORMATION: Synthesized

<400> SEQUENCE: 26

Gly Thr Asn Asn Arg Ala Pro
1               5
```

```
<210> SEQ ID NO 27
<211> LENGTH: 9
<212> TYPE: PRT
<213> ORGANISM: Artificial Sequence
<220> FEATURE:
<223> OTHER INFORMATION: Synthesized

<400> SEQUENCE: 27

Ala Leu Trp Tyr Ser Asn His Trp Val
1               5
```

```
<210> SEQ ID NO 28
<211> LENGTH: 11
<212> TYPE: PRT
<213> ORGANISM: Artificial Sequence
<220> FEATURE:
<223> OTHER INFORMATION: Synthesized

<400> SEQUENCE: 28
```

```
Arg Ala Ser Glu Asn Ile Tyr Ser Tyr Val Ala
1               5                   10

<210> SEQ ID NO 29
<211> LENGTH: 7
<212> TYPE: PRT
<213> ORGANISM: Artificial Sequence
<220> FEATURE:
<223> OTHER INFORMATION: Synthesized

<400> SEQUENCE: 29

Asn Ala Lys Thr Leu Ala Glu
1               5

<210> SEQ ID NO 30
<211> LENGTH: 9
<212> TYPE: PRT
<213> ORGANISM: Artificial Sequence
<220> FEATURE:
<223> OTHER INFORMATION: Synthesized

<400> SEQUENCE: 30

Gln His His Tyr Gly Ile Pro Leu Thr
1               5

<210> SEQ ID NO 31
<211> LENGTH: 10
<212> TYPE: PRT
<213> ORGANISM: Artificial Sequence
<220> FEATURE:
<223> OTHER INFORMATION: Synthesized

<400> SEQUENCE: 31

Ser Ala Ser Ser Ser Val Gly Tyr Met His
1               5                   10

<210> SEQ ID NO 32
<211> LENGTH: 7
<212> TYPE: PRT
<213> ORGANISM: Artificial Sequence
<220> FEATURE:
<223> OTHER INFORMATION: Synthesized

<400> SEQUENCE: 32

Asp Thr Ser Lys Leu Ala Ser
1               5

<210> SEQ ID NO 33
<211> LENGTH: 9
<212> TYPE: PRT
<213> ORGANISM: Artificial Sequence
<220> FEATURE:
<223> OTHER INFORMATION: Synthesized

<400> SEQUENCE: 33

Gln Gln Trp Ser Ser Ile Pro Leu Thr
1               5

<210> SEQ ID NO 34
<211> LENGTH: 11
<212> TYPE: PRT
<213> ORGANISM: Artificial Sequence
<220> FEATURE:
<223> OTHER INFORMATION: Synthesized

<400> SEQUENCE: 34

Arg Ala Ser Glu Asn Ile Tyr Thr Tyr Leu Ala
```

-continued

```
1              5              10

<210> SEQ ID NO 35
<211> LENGTH: 7
<212> TYPE: PRT
<213> ORGANISM: Artificial Sequence
<220> FEATURE:
<223> OTHER INFORMATION: Synthesized

<400> SEQUENCE: 35

Asn Thr Lys Thr Leu Ala Glu
1              5

<210> SEQ ID NO 36
<211> LENGTH: 9
<212> TYPE: PRT
<213> ORGANISM: Artificial Sequence
<220> FEATURE:
<223> OTHER INFORMATION: Synthesized

<400> SEQUENCE: 36

Gln His His Tyr Gly Val Pro Leu Thr
1              5

<210> SEQ ID NO 37
<211> LENGTH: 16
<212> TYPE: PRT
<213> ORGANISM: Artificial Sequence
<220> FEATURE:
<223> OTHER INFORMATION: Synthesized

<400> SEQUENCE: 37

Arg Ser Ser Lys Ser Leu Leu His Ser Asn Gly Asn Thr Tyr Leu Tyr
1              5                  10                 15

<210> SEQ ID NO 38
<211> LENGTH: 7
<212> TYPE: PRT
<213> ORGANISM: Artificial Sequence
<220> FEATURE:
<223> OTHER INFORMATION: Synthesized

<400> SEQUENCE: 38

Arg Met Ser Asn Leu Ala Ser
1              5

<210> SEQ ID NO 39
<211> LENGTH: 9
<212> TYPE: PRT
<213> ORGANISM: Artificial Sequence
<220> FEATURE:
<223> OTHER INFORMATION: Synthesized

<400> SEQUENCE: 39

Met Gln His Leu Glu Phe Pro Leu Thr
1              5

<210> SEQ ID NO 40
<211> LENGTH: 10
<212> TYPE: PRT
<213> ORGANISM: Artificial Sequence
<220> FEATURE:
<223> OTHER INFORMATION: Synthesized

<400> SEQUENCE: 40

Ser Ala Ser Ser Ser Val Gly Tyr Met His
1              5                  10
```

<210> SEQ ID NO 41
<211> LENGTH: 7
<212> TYPE: PRT
<213> ORGANISM: Artificial Sequence
<220> FEATURE:
<223> OTHER INFORMATION: Synthesized

<400> SEQUENCE: 41

Asp Thr Ser Lys Leu Ala Ser
1               5

<210> SEQ ID NO 42
<211> LENGTH: 9
<212> TYPE: PRT
<213> ORGANISM: Artificial Sequence
<220> FEATURE:
<223> OTHER INFORMATION: Synthesized

<400> SEQUENCE: 42

Gln Gln Trp Ser Ser Ile Pro Leu Thr
1               5

<210> SEQ ID NO 43
<211> LENGTH: 14
<212> TYPE: PRT
<213> ORGANISM: Artificial Sequence
<220> FEATURE:
<223> OTHER INFORMATION: Synthesized

<400> SEQUENCE: 43

Arg Ser Ser Thr Gly Ala Val Thr Thr Ser Asn His Ala Asn
1               5                   10

<210> SEQ ID NO 44
<211> LENGTH: 7
<212> TYPE: PRT
<213> ORGANISM: Artificial Sequence
<220> FEATURE:
<223> OTHER INFORMATION: Synthesized

<400> SEQUENCE: 44

Gly Ile Asn Asn Arg Ala Pro
1               5

<210> SEQ ID NO 45
<211> LENGTH: 9
<212> TYPE: PRT
<213> ORGANISM: Artificial Sequence
<220> FEATURE:
<223> OTHER INFORMATION: Synthesized

<400> SEQUENCE: 45

Ala Leu Trp Tyr Ser Asn His Trp Val
1               5

<210> SEQ ID NO 46
<211> LENGTH: 10
<212> TYPE: PRT
<213> ORGANISM: Artificial Sequence
<220> FEATURE:
<223> OTHER INFORMATION: Synthesized

<400> SEQUENCE: 46

Ser Ala Ser Ser Ile Ile Ser Tyr Met His
1               5                   10

```
<210> SEQ ID NO 47
<211> LENGTH: 7
<212> TYPE: PRT
<213> ORGANISM: Artificial Sequence
<220> FEATURE:
<223> OTHER INFORMATION: Synthesized

<400> SEQUENCE: 47

Asp Thr Ser Lys Leu Ala Ser
1               5

<210> SEQ ID NO 48
<211> LENGTH: 9
<212> TYPE: PRT
<213> ORGANISM: Artificial Sequence
<220> FEATURE:
<223> OTHER INFORMATION: Synthesized

<400> SEQUENCE: 48

His Gln Trp Thr Ser Asn Pro Leu Thr
1               5

<210> SEQ ID NO 49
<211> LENGTH: 117
<212> TYPE: PRT
<213> ORGANISM: Artificial Sequence
<220> FEATURE:
<223> OTHER INFORMATION: Synthesized

<400> SEQUENCE: 49

Gln Val Gln Leu Gln Gln Ser Gly Ala Glu Leu Met Lys Pro Gly Ala
1               5                   10                  15

Ser Val Lys Ile Ser Cys Lys Ala Ile Gly Tyr Thr Phe Ser Arg Tyr
            20                  25                  30

Trp Ile Glu Trp Val Lys Gln Arg Pro Gly His Gly Leu Glu Trp Ile
        35                  40                  45

Gly Glu Ile Leu Pro Gly Arg Gly Val Thr Asn Tyr Asn Glu Asn Phe
    50                  55                  60

Lys Gly Lys Ala Thr Phe Thr Val Asp Ile Ser Ser Thr Thr Thr Tyr
65                  70                  75                  80

Ile Gln Phe Ser Ser Leu Thr Ser Glu Asp Ser Ala Val Tyr Tyr Cys
                85                  90                  95

Ala Arg Ser Asn Tyr Gly Asp Tyr Asp Phe Trp Gly Gln Gly Thr Ser
            100                 105                 110

Leu Thr Val Ser Ser
        115

<210> SEQ ID NO 50
<211> LENGTH: 118
<212> TYPE: PRT
<213> ORGANISM: Artificial Sequence
<220> FEATURE:
<223> OTHER INFORMATION: Synthesized

<400> SEQUENCE: 50

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45
```

```
Gly Glu Ile Asn Pro Asn Asn Gly Leu Thr Asn Tyr Asp Glu Lys Phe
    50              55              60

Lys Thr Lys Ala Thr Leu Thr Ile Asp Lys Ser Ser Arg Thr Ala Tyr
65              70              75              80

Ile Gln Leu Ser Ser Leu Thr Ser Glu Asp Ser Ala Val Tyr Tyr Cys
                85              90              95

Ala Lys Tyr Gly Asn Tyr Val Ala Phe Ala Phe Trp Gly Gln Gly Thr
            100             105             110

Leu Val Thr Val Ser Ala
        115

<210> SEQ ID NO 51
<211> LENGTH: 117
<212> TYPE: PRT
<213> ORGANISM: Artificial Sequence
<220> FEATURE:
<223> OTHER INFORMATION: Synthesized

<400> SEQUENCE: 51

Gln Val Gln Leu Gln Gln Pro Gly Ala Glu Leu Val Lys Pro Gly Ala
1               5               10              15

Ser Val Lys Leu Ser Cys Lys Ser Ser Gly Tyr Thr Phe Thr Asn Tyr
            20              25              30

Trp Met His Trp Val Lys Gln Arg Pro Gly Gln Gly Leu Glu Trp Ile
        35              40              45

Gly Glu Ile Tyr Pro Ser Asn Gly Arg Thr Asn Tyr Asn Glu Lys Phe
    50              55              60

Lys Asn Arg Ala Thr Leu Thr Val Asp Ile Ser Ser Thr Ala Tyr
65              70              75              80

Met Gln Leu Ser Ser Leu Thr Ser Glu Asp Ser Ala Val Tyr Tyr Cys
                85              90              95

Ala Arg Ser Arg Tyr Asp Pro Met Glu Asp Trp Gly Gln Gly Thr Ser
            100             105             110

Val Thr Val Ser Ser
        115

<210> SEQ ID NO 52
<211> LENGTH: 118
<212> TYPE: PRT
<213> ORGANISM: Artificial Sequence
<220> FEATURE:
<223> OTHER INFORMATION: Synthesized

<400> SEQUENCE: 52

Gln Val Gln Leu Gln Gln Pro Gly Ala Glu Leu Val Lys Pro Gly Ala
1               5               10              15

Ser Val Gln Leu Ser Cys Lys Ala Ser Gly Tyr Thr Phe Thr Ser Tyr
            20              25              30

Trp Ile His Trp Val Lys Gln Arg Pro Gly Gln Gly Leu Glu Trp Ile
        35              40              45

Gly Glu Ile Asn Pro Asn Asn Gly Leu Thr Asn Tyr Ile Glu Lys Phe
    50              55              60

Lys Asn Lys Ala Thr Leu Thr Ile Asp Lys Ser Ser Asn Thr Ala Tyr
65              70              75              80

Met Gln Leu Ser Gly Leu Thr Pro Glu Asp Ser Ala Val Tyr Tyr Cys
                85              90              95

Ala Lys Tyr Gly Asn Tyr Val Ala Phe Ala Tyr Trp Gly Gln Gly Thr
            100             105             110
```

-continued

---

Leu Val Thr Val Ser Ala
      115

<210> SEQ ID NO 53
<211> LENGTH: 119
<212> TYPE: PRT
<213> ORGANISM: Artificial Sequence
<220> FEATURE:
<223> OTHER INFORMATION: Synthesized

<400> SEQUENCE: 53

Gln Val Gln Leu Gln Gln Ser Gly Thr Glu Leu Met Lys Pro Gly Ala
1               5                   10                  15

Ser Val Lys Ile Ser Cys Lys Ala Thr Gly Tyr Thr Phe Ser Arg Tyr
            20                  25                  30

Trp Ile Glu Trp Val Lys Gln Arg Pro Gly His Gly Leu Glu Trp Ile
        35                  40                  45

Gly Glu Ile Leu Pro Gly Arg Ser Ser Thr Asn Tyr Asn Glu Lys Phe
    50                  55                  60

Lys Gly Lys Ala Thr Phe Thr Ala Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Thr Arg Val Ser Gln Leu His Ile Tyr Phe Asp Tyr Trp Gly Gln Gly
            100                 105                 110

Thr Thr Val Thr Val Ser Ser
      115

<210> SEQ ID NO 54
<211> LENGTH: 117
<212> TYPE: PRT
<213> ORGANISM: Artificial Sequence
<220> FEATURE:
<223> OTHER INFORMATION: Synthesized

<400> SEQUENCE: 54

Gln Val Gln Leu Gln Gln Pro Gly Ala Glu Leu Val Lys Pro Gly Ala
1               5                   10                  15

Ser Val Lys Leu Ser Cys Lys Ser Ser Gly Tyr Thr Phe Thr Asn Tyr
            20                  25                  30

Trp Met His Trp Val Arg Gln Arg Pro Gly Gln Gly Leu Glu Trp Ile
        35                  40                  45

Gly Glu Ile Tyr Pro Asn Asn Gly Arg Val Asn Tyr Asn Glu Lys Phe
    50                  55                  60

Lys Asn Arg Ala Thr Leu Thr Val Asp Ile Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Arg Tyr Asp Pro Met Glu Asp Trp Gly Gln Gly Thr Ser
            100                 105                 110

Val Thr Val Ser Ser
      115

<210> SEQ ID NO 55
<211> LENGTH: 117
<212> TYPE: PRT
<213> ORGANISM: Artificial Sequence
<220> FEATURE:
<223> OTHER INFORMATION: Synthesized

```
<400> SEQUENCE: 55

Gln Val Gln Leu Gln Gln Pro Gly Val Glu Leu Val Lys Pro Gly Ala
1               5                   10                  15

Ser Val Lys Leu Ser Cys Lys Thr Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Tyr Ser Ser Asn Gly Leu Thr Asn Tyr Asn Glu Lys Phe
    50                  55                  60

Lys Asn Lys Ala Thr Leu Thr Val Asp Lys Ser Ser Ser Thr Ala Tyr
65                  70                  75                  80

Met Gln Leu Thr Ser Leu Thr Ser Glu Asp Ser Ala Ile Tyr Tyr Cys
                85                  90                  95

Ala Arg His Trp Tyr Val Phe Leu Asp His Trp Gly Gln Gly Thr Thr
            100                 105                 110

Leu Thr Val Ser Ser
        115

<210> SEQ ID NO 56
<211> LENGTH: 117
<212> TYPE: PRT
<213> ORGANISM: Artificial Sequence
<220> FEATURE:
<223> OTHER INFORMATION: Synthesized

<400> SEQUENCE: 56

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Asn Tyr
            20                  25                  30

Trp Met His Trp Val Lys Gln Arg Pro Gly Gln Gly Leu Glu Trp Ile
        35                  40                  45

Gly Glu Ile Tyr Pro Ser Asn Gly Arg Thr Asn Tyr Asn Glu Lys Phe
    50                  55                  60

Lys Thr Lys Ala Thr Leu Thr Val Asp Lys Ser Ser Ser Thr Ala Tyr
65                  70                  75                  80

Met His Leu Ser Ser Leu Thr Ser Glu Asp Ser Ala Val Tyr Tyr Cys
                85                  90                  95

Ala Gly Ser Arg Tyr Asp Ala Met Asp Phe Trp Gly Gln Gly Thr Ser
            100                 105                 110

Val Thr Val Ser Ser
        115

<210> SEQ ID NO 57
<211> LENGTH: 109
<212> TYPE: PRT
<213> ORGANISM: Artificial Sequence
<220> FEATURE:
<223> OTHER INFORMATION: Synthesized

<400> SEQUENCE: 57

Gln Thr Val Val Thr Gln Glu Ser Ala Leu Thr Thr Ser Pro Gly Glu
1               5                   10                  15

Thr Val Thr Leu Thr Cys Arg Ser Ser Ser Gly Ala Val Thr Thr Ser
            20                  25                  30

Asn His Ala Asn Trp Val Gln Glu Lys Pro Asp His Leu Phe Thr Ser
        35                  40                  45
```

-continued

---

Leu Met Gly Gly Thr Asn Asn Arg Ala Pro Gly Val Pro Ala Arg Phe
    50             55             60

Ser Gly Ser Leu Ile Gly Asp Lys Ala Ala Leu Thr Ile Thr Gly Ala
65             70             75             80

Gln Thr Glu Asp Glu Ala Ile Tyr Phe Cys Ala Leu Trp Tyr Ser Asn
            85            90            95

His Trp Val Phe Gly Gly Gly Thr Lys Leu Thr Val Leu
        100            105

<210> SEQ ID NO 58
<211> LENGTH: 107
<212> TYPE: PRT
<213> ORGANISM: Artificial Sequence
<220> FEATURE:
<223> OTHER INFORMATION: Synthesized

<400> SEQUENCE: 58

Asp Ile Gln Met Thr Gln Ser Pro Ala Ser Leu Ser Ala Thr Val Gly
1            5            10            15

Glu Thr Val Thr Ile Thr Cys Arg Ala Ser Glu Asn Ile Tyr Ser Tyr
            20            25            30

Val Ala Trp Tyr Gln Gln Lys Gln Gly Lys Ser Pro Gln Leu Leu Val
        35            40            45

His Asn Ala Lys Thr Leu Ala Glu Gly Val Pro Ser Arg Phe Ser Gly
    50              55              60

Ser Gly Ser Gly Thr Gln Phe Ser Leu Lys Ile Asn Gly Leu His Pro
65             70             75             80

Glu Asp Phe Gly Ser Tyr Tyr Cys Gln His His Tyr Gly Ile Pro Leu
            85            90            95

Thr Phe Gly Ala Gly Thr Lys Leu Glu Leu Lys
        100            105

<210> SEQ ID NO 59
<211> LENGTH: 106
<212> TYPE: PRT
<213> ORGANISM: Artificial Sequence
<220> FEATURE:
<223> OTHER INFORMATION: Synthesized

<400> SEQUENCE: 59

Gln Ile Val Leu Thr Gln Ser Pro Ala Ile Met Ser Ala Ser Pro Gly
1            5            10            15

Glu Lys Val Thr Met Thr Cys Ser Ala Ser Ser Ser Val Gly Tyr Met
            20            25            30

His Trp Tyr Gln Gln Lys Ser Gly Thr Ser Pro Lys Arg Trp Ile Tyr
        35            40            45

Asp Thr Ser Lys Leu Ala Ser Gly Val Pro Thr Arg Phe Ser Gly Ser
    50              55              60

Gly Ser Gly Thr Ser Tyr Ser Leu Thr Ile Ser Ser Met Glu Ala Glu
65             70             75             80

Asp Ala Ala Thr Tyr Tyr Cys Gln Gln Trp Ser Ser Ile Pro Leu Thr
            85            90            95

Phe Gly Ser Gly Thr Lys Leu Glu Ile Lys
        100            105

<210> SEQ ID NO 60
<211> LENGTH: 107
<212> TYPE: PRT

<213> ORGANISM: Artificial Sequence
<220> FEATURE:
<223> OTHER INFORMATION: Synthesized

<400> SEQUENCE: 60

```
Asp Ile Gln Met Thr Gln Ser Pro Ala Ser Leu Ser Ala Ser Val Gly
1               5                   10                  15

Asp Thr Val Thr Ile Thr Cys Arg Ala Ser Glu Asn Ile Tyr Thr Tyr
            20                  25                  30

Leu Ala Trp Tyr Gln Gln Lys Gln Gly Lys Ser Pro Gln Leu Leu Val
        35                  40                  45

His Asn Thr Lys Thr Leu Ala Glu Gly Val Pro Ser Arg Phe Ser Gly
    50                  55                  60

Ser Gly Ser Gly Thr Gln Phe Ser Leu Lys Ile Ser Ser Leu Gln Pro
65                  70                  75                  80

Glu Asp Phe Gly Thr Tyr Tyr Cys Gln His His Tyr Gly Val Pro Leu
                85                  90                  95

Thr Phe Gly Ala Gly Thr Lys Leu Glu Leu Lys
            100                 105
```

<210> SEQ ID NO 61
<211> LENGTH: 112
<212> TYPE: PRT
<213> ORGANISM: Artificial Sequence
<220> FEATURE:
<223> OTHER INFORMATION: Synthesized

<400> SEQUENCE: 61

```
Asp Ile Val Met Thr Gln Val Val Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Gln Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Ala Phe Tyr Tyr Cys Met Gln His
            85                  90                  95

Leu Glu Phe Pro Leu Thr Phe Gly Ala Gly Thr Lys Leu Glu Leu Lys
            100                 105                 110
```

<210> SEQ ID NO 62
<211> LENGTH: 106
<212> TYPE: PRT
<213> ORGANISM: Artificial Sequence
<220> FEATURE:
<223> OTHER INFORMATION: Synthesized

<400> SEQUENCE: 62

```
Gln Val Val Leu Thr Gln Ser Pro Ala Ile Met Ser Ala Ser Pro Gly
1               5                   10                  15

Glu Lys Val Thr Met Thr Cys Ser Ala Ser Ser Ser Val Gly Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Thr Arg Phe Ser Gly Ser
    50                  55                  60
```

Gly Ser Gly Thr Ser Tyr Ser Leu Thr Ile Ser Ser Met Glu Ala Glu
65                  70                  75                  80

Asp Ala Ala Thr Tyr Phe Cys Gln Gln Trp Ser Ser Ile Pro Leu Thr
                85                  90                  95

Phe Gly Ser Gly Thr Arg Leu Glu Ile Lys
            100                 105

<210> SEQ ID NO 63
<211> LENGTH: 109
<212> TYPE: PRT
<213> ORGANISM: Artificial Sequence
<220> FEATURE:
<223> OTHER INFORMATION: Synthesized

<400> SEQUENCE: 63

Gln Ala Val Val Thr Gln Glu Ser Ala Leu Thr Thr Ser Pro Gly Glu
1                   5                   10                  15

Thr Val Thr Leu Thr Cys Arg Ser Ser Thr Gly Ala Val Thr Thr Ser
                20                  25                  30

Asn His Ala Asn Trp Val Gln Glu Lys Pro Asp His Leu Phe Thr Gly
            35                  40                  45

Leu Ile Gly Gly Ile Asn Asn Arg Ala Pro Gly Val Pro Ala Arg Phe
        50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Trp Val Phe Gly Gly Gly Thr Arg Leu Thr Val Leu
            100                 105

<210> SEQ ID NO 64
<211> LENGTH: 106
<212> TYPE: PRT
<213> ORGANISM: Artificial Sequence
<220> FEATURE:
<223> OTHER INFORMATION: Synthesized

<400> SEQUENCE: 64

Gln Ile Val Leu Thr Gln Ser Pro Ala Ile Met Ser Ala Ser Pro Gly
1                   5                   10                  15

Glu Lys Val Thr Met Thr Cys Ser Ala Ser Ser Ile Ile Ser Tyr Met
                20                  25                  30

His Trp Tyr Gln Gln Lys Ser Gly Thr Ser Pro Lys Arg Trp Ile Tyr
            35                  40                  45

Asp Thr Ser Lys Leu Ala Ser Gly Val Pro Ala Arg Phe Ser Gly Ser
        50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys His Gln Trp Thr Ser Asn Pro Leu Thr
                85                  90                  95

Phe Gly Gly Gly Thr Lys Leu Glu Leu Lys
            100                 105

<210> SEQ ID NO 65
<211> LENGTH: 351
<212> TYPE: DNA
<213> ORGANISM: Artificial Sequence
<220> FEATURE:
<223> OTHER INFORMATION: Synthesized

<400> SEQUENCE: 65
caggttcagc tgcagcagtc tggagctgag ctgatgaagc ctggggcctc agtgaagata        60
tcctgcaagg ctattgggta cacattcagt aggtactgga tagagtgggt aaagcagagg       120
cctggacatg gccttgagtg gattggagag attttacctg gaagaggtgt tactaactac       180
aatgagaact tcaagggcaa ggccacattc actgtagata tatcctccac cacaacctac       240
attcaattca gcagcctgac atctgaggac tctgccgtct attactgtgc aagatcgaat       300
tatggtgact acgacttctg gggccaaggc acctctctca cagtctcctc a               351

<210> SEQ ID NO 66
<211> LENGTH: 327
<212> TYPE: DNA
<213> ORGANISM: Artificial Sequence
<220> FEATURE:
<223> OTHER INFORMATION: Synthesized

<400> SEQUENCE: 66
cagactgttg tgactcagga atctgcactc accacatcac ctggtgaaac agtcacactc        60
acttgtcgct caagttctgg ggctgttaca actagtaacc atgccaactg ggtccaagaa       120
aaacctgatc atttattcac tagtctaatg ggtggtacca ataaccgagc tccaggtgtt       180
cctgccagat tctcaggctc cctgattggc gacaaggctg ccctcaccat cacaggggcg       240
cagactgagg atgaggcaat atatttctgt gctctctggt acagcaacca ttgggtgttc       300
ggtggaggaa ctaaactgac tgtccta                                           327

<210> SEQ ID NO 67
<211> LENGTH: 354
<212> TYPE: DNA
<213> ORGANISM: Artificial Sequence
<220> FEATURE:
<223> OTHER INFORMATION: Synthesized

<400> SEQUENCE: 67
caggtccaac tgcagcagcc tggggctgaa ctggtgaagc ctggggcttc agtgaagctg        60
tcctgcaagg cttccggcta cacctttacc agctactgga tgcactgggt gaagcagagg       120
cctggacaag gccttgagtg gattggagag attaatccta caacggtct tactaactac        180 gatgagaaat tcaagaccaa ggccacactg accatagaca atcctccag aacagcctac        240 atacaactca gcagcctgac atctgaggac tctgcggtct attactgtgc aaaatatggt       300
aactacgtcg cgtttgcttt ctggggccaa gggactctgg tcactgtctc tgca             354

<210> SEQ ID NO 68
<211> LENGTH: 321
<212> TYPE: DNA
<213> ORGANISM: Artificial Sequence
<220> FEATURE:
<223> OTHER INFORMATION: Synthesized

<400> SEQUENCE: 68
gacattcaga tgactcagtc tccagcctcc ctatctgcaa ctgtgggaga aactgtcacc        60
atcacatgtc gagcaagtga aaatatttac agttatgtag catggtatca gcagaaacag       120
ggaaaatctc ctcaactcct ggtccataat gcaaaaacct tagcagaagg tgtaccatca       180
aggttcagtg gcagtggatc aggcacacag ttttctctga agatcaacgg cctgcaccct       240
gaagattttg ggagttatta ctgtcaacat cattatggta ttccgctcac gttcggcgct       300

-continued

```
gggaccaagc tggagctgaa a                                          321

<210> SEQ ID NO 69
<211> LENGTH: 351
<212> TYPE: DNA
<213> ORGANISM: Artificial Sequence
<220> FEATURE:
<223> OTHER INFORMATION: Synthesized

<400> SEQUENCE: 69
caggtccaac tgcagcagcc tggggctgaa ctggtgaagc ctggggcttc tgtgaagctg    60
tcctgcaagt cttctggcta taccttcacc aactactgga tgcactgggt gaagcagcgg   120
cctggacaag gccttgagtg gattggagag atttatccta gcaacggtcg tactaactac   180
aatgagaagt tcaaaaacag ggccacactg actgtagaca tttcctccag cacagcctac   240
atgcaactca gcagcctgac atctgaggac tctgcggtct attactgtgc aaggagtagg   300
tacgacccta tggaagactg gggtcaagga acctcagtca ccgtctcctc t             351

<210> SEQ ID NO 70
<211> LENGTH: 318
<212> TYPE: DNA
<213> ORGANISM: Artificial Sequence
<220> FEATURE:
<223> OTHER INFORMATION: Synthesized

<400> SEQUENCE: 70
caaattgttc tcacccagtc tccagcaatc atgtctgcat ctccagggga gaaggtcacc    60
atgacctgca gtgccagctc aagtgtgggt tacatgcact ggtaccagca gaagtcaggc   120
acctccccca aaagatggat ttatgacaca tccaaactgg cttctggagt cccaactcgc   180
ttcagtggca gtgggtctgg gacctcttac tctctcacaa tcagcagcat ggaggctgag   240
gatgctgcca cttattactg ccagcagtgg agtagtatcc cactcacgtt cggctcgggg   300
acaaagttgg aaataaag                                                  318

<210> SEQ ID NO 71
<211> LENGTH: 354
<212> TYPE: DNA
<213> ORGANISM: Artificial Sequence
<220> FEATURE:
<223> OTHER INFORMATION: Synthesized

<400> SEQUENCE: 71
caggtccaac tgcagcagcc tggggctgaa ctggtgaagc ctggggcttc agtgcagctg    60
tcctgcaagg cttctggcta caccttcacc agttactgga tacactgggt gaaacagagg   120
cctggacaag gccttgagtg gattggagag attaatccta caacggtct tactaactac     180 attgagaaat tcaagaacaa ggccacactg actattgaca atcctccaa cacagcctac      240 atgcaactca gcggcctgac acctgaggac tctgcggtct attactgtgc aaaatatggt    300
aactacgtcg cgtttgctta ctggggccag gggactctgg tcactgtctc tgca          354

<210> SEQ ID NO 72
<211> LENGTH: 321
<212> TYPE: DNA
<213> ORGANISM: Artificial Sequence
<220> FEATURE:
<223> OTHER INFORMATION: Synthesized

<400> SEQUENCE: 72
gacatccaga tgactcagtc tccagcctcc ctatctgcat ctgtgggaga cactgtcacc    60
```

-continued

```
atcacatgtc gagcaagtga aaatatctac acttatttag cttggtatca gcagaaacag        120
ggaaaatctc ctcaactcct ggtccataat acaaaaacct tagcagaagg tgtgccctca        180
aggttcagtg gcagtggatc aggcacacag ttttctctga agatcagcag cctgcagcct        240
gaagattttg ggacttatta ctgtcaacat cattatggtg ttccgctcac gttcggtgct        300
gggaccaagc tggagctgaa a                                                  321
```

```
<210> SEQ ID NO 73
<211> LENGTH: 357
<212> TYPE: DNA
<213> ORGANISM: Artificial Sequence
<220> FEATURE:
<223> OTHER INFORMATION: Synthesized

<400> SEQUENCE: 73
caggttcagc tgcagcagtc tggaactgaa ctgatgaagc ctggggcctc agtgaagata         60
tcctgcaagg ctactggcta cacattcagt agatactgga tagagtgggt aaaacagagg        120
cctggacatg gccttgagtg gattggagag attttacctg gaaggagtag tactaactac        180
aatgagaagt tcaagggcaa ggccacattc actgccgata catcctccaa cacagcctac        240
atgcaactca gcagcctgac atctgaggac tctgccgtct attactgtac aagagtttcc        300
caactgcaca tttactttga ctactggggc caagggacca ctgtcacagt ctcctcc          357
```

```
<210> SEQ ID NO 74
<211> LENGTH: 336
<212> TYPE: DNA
<213> ORGANISM: Artificial Sequence
<220> FEATURE:
<223> OTHER INFORMATION: Synthesized

<400> SEQUENCE: 74
gatattgtga tgactcaggt tgtaccctct gtacctgtca ctcctggaga gtcagtatcc         60
atctcctgca ggtctagtaa gagtctcctg catagtaatg gcaacactta cttatattgg        120
ttccagcaga ggccaggcca gtctcctcag ctcctgatat atcggatgtc caaccttgcc        180
tcaggagtcc cagacaggtt cagtggcagt gggtcaggaa ctgctttcac attgagaatc        240
agtagagtgg aggctgagga tgtggctttt tattactgta tgcaacatct agaatttccg        300
ctcacgttcg gtgctgggac caagttggag ctgaaa                                  336
```

```
<210> SEQ ID NO 75
<211> LENGTH: 351
<212> TYPE: DNA
<213> ORGANISM: Artificial Sequence
<220> FEATURE:
<223> OTHER INFORMATION: Synthesized

<400> SEQUENCE: 75
caggtccaac tgcagcagcc tggggctgaa ctggtgaaac ctggggcttc agtgaagctg         60
tcctgcaagt cttctggcta taccttcacc aactactgga tgcactgggt gaggcagagg        120
cctggacaag gccttgagtg gattggagag atctatccta caacggtcg tgttaactac         180 aatgagaagt tcaagaacag gccacactg actgtagaca tatcctccag cacagcctac         240
atgcaactca gcagcctgac atctgaggac tctgcggtct attactgtgc aaggagtagg        300 tacgaccta tggaagactg gggtcaagga acctcagtca ccgtctcctc t                  351
```

```
<210> SEQ ID NO 76
```

```
<211> LENGTH: 318
<212> TYPE: DNA
<213> ORGANISM: Artificial Sequence
<220> FEATURE:
<223> OTHER INFORMATION: Synthesized

<400> SEQUENCE: 76
caagttgttc tcacccagtc tccagcaatc atgtctgcat ctccagggga gaaggtcacc       60
atgacctgca gtgccagctc aagtgtaggt tacatgcact ggtaccagca gaagtcaggc      120 acctcccccca aaagatggat ttatgacaca tccaaactgg cttctggagt cccaactcgc      180
ttcagtggca gtgggtctgg gacctcttac tctctcacaa tcagcagcat ggaggctgag      240
gatgctgcca cttatttctg ccagcagtgg agtagtatcc cactcacgtt cggctcgggg      300
acaaggttgg aaataaag                                                     318

<210> SEQ ID NO 77
<211> LENGTH: 351
<212> TYPE: DNA
<213> ORGANISM: Artificial Sequence
<220> FEATURE:
<223> OTHER INFORMATION: Synthesized

<400> SEQUENCE: 77
caggtccaac tgcagcagcc tggggttgaa ctggtgaagc ctggggcttc agtgaagctg       60
tcctgcaaga cttctggcta caccttcacc agctactgga tgcactgggt gaagcagagg      120
cctggacaag gccttgaatg gattggagag atttattcca gtaacggtct tactaactac      180
aatgagaagt tcaagaataa ggccacactg actgtagata atcctccag cacagcctac       240 atgcaactca ccagcctgac atctgaagac tctgcgatct attactgtgc aagacattgg      300
tacgtcttcc ttgaccactg gggccaaggc accactctca cagtctcctc a               351

<210> SEQ ID NO 78
<211> LENGTH: 327
<212> TYPE: DNA
<213> ORGANISM: Artificial Sequence
<220> FEATURE:
<223> OTHER INFORMATION: Synthesized

<400> SEQUENCE: 78
caggctgttg tgactcagga atctgcactc accacatcac ctggtgaaac agtcacactc       60
acttgtcgct caagtactgg ggctgttaca actagtaacc atgccaactg ggtccaagaa      120
aaaccagatc atttattcac tggtctaata ggtggtatca acaaccgagc tccaggtgtt      180
cctgccagat tctcaggctc cctgattgga gacaaggctg ccctcaccat cacaggggca      240
cagactgagg atgaggcaat atatttctgt gctctatggt acagcaatca ttgggtgttc      300
ggtggaggaa ccagactgac tgtccta                                          327

<210> SEQ ID NO 79
<211> LENGTH: 351
<212> TYPE: DNA
<213> ORGANISM: Artificial Sequence
<220> FEATURE:
<223> OTHER INFORMATION: Synthesized

<400> SEQUENCE: 79
caggtccaac tgcagcagcc tggggctgaa cttgtgaagc ctggggcttc agtgaagctg       60
tcctgtaagg cttctggcta caccttcacc aactactgga tgcattgggt gaaacagagg      120
cctggacaag gccttgagtg gattggagag atttatccta gcaacggtcg tactaactac      180
```

-continued

```
aatgagaagt tcaagaccaa ggccacactg actgtagaca aatcctccag cacagcctac        240
atgcatctca gcagcctgac atctgaggac tctgcggtct attactgtgc aggatcgaga        300
tacgatgcta tggacttctg gggtcaagga acctcagtca ccgtctcctc a                351

<210> SEQ ID NO 80
<211> LENGTH: 318
<212> TYPE: DNA
<213> ORGANISM: Artificial Sequence
<220> FEATURE:
<223> OTHER INFORMATION: Synthesized

<400> SEQUENCE: 80
caaattgttc tcacccagtc tccagcaatc atgtctgcat ctccagggga gaaggtcacc         60
atgacctgca gtgccagctc aattataagt tacatgcact ggtaccagca gaagtcaggc        120
acctccccca aaagatggat ttatgacact tccaaactgg cttctggagt ccctgctcgc        180
ttcagtggca gtgggtctgg gacctcttac tctctcacaa tcagtggcat ggaggctgaa        240
gatgctgcca cttattactg ccaccagtgg actagtaacc cgctcacgtt cggtggtggg        300
accaagctgg aactgaaa                                                      318

<210> SEQ ID NO 81
<211> LENGTH: 117
<212> TYPE: PRT
<213> ORGANISM: Artificial Sequence
<220> FEATURE:
<223> OTHER INFORMATION: Synthesized

<400> SEQUENCE: 81

Gln Val Gln Leu Val Gln Ser Gly Ala Glu Val Lys Lys Pro Gly Ala
1               5                   10                  15

Ser Val Lys Val Ser Cys Lys Ser Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Glu Ile Tyr Pro Asn Asn Gly Arg Val Asn Tyr Asn Glu Lys Phe
    50                  55                  60

Lys Asn Arg Val Thr Met Thr Val Asp Ile Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Arg Tyr Asp Pro Met Glu Asp Trp Gly Gln Gly Thr Thr
            100                 105                 110

Val Thr Val Ser Ser
        115

<210> SEQ ID NO 82
<211> LENGTH: 351
<212> TYPE: DNA
<213> ORGANISM: Artificial Sequence
<220> FEATURE:
<223> OTHER INFORMATION: Synthesized

<400> SEQUENCE: 82
caggtgcagc tggtgcagag cggagctgag gtgaagaagc caggagcttc cgtgaaggtg         60
agctgcaagt ccagcggcta caccttcaca aactattgga tgcactgggt gaggcaggct        120
ccaggacagg gactggagtg gatgggcgag atctacccta caatggcag ggtgaactac         180
```

-continued

```
aacgagaagt ttaagaacag agtgaccatg acagtggaca tcagcatctc taccgcttac      240
atggagctgt ctaggctgcg gtccgacgat acagccgtgt actattgtgc tagatctcgc      300
tatgacccca tggaggattg gggccagggc accacagtga ccgtgtcttc c              351
```

<210> SEQ ID NO 83
<211> LENGTH: 106
<212> TYPE: PRT
<213> ORGANISM: Artificial Sequence
<220> FEATURE:
<223> OTHER INFORMATION: Synthesized

<400> SEQUENCE: 83

```
Asp Val Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Gly Tyr Met
            20                  25                  30

His Trp Tyr Gln Gln Lys Pro Gly Lys Ala Pro Lys Arg Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Phe Cys Gln Gln Trp Ser Ser Ile Pro Leu Thr
                85                  90                  95

Phe Gly Gln Gly Thr Arg Leu Glu Ile Lys
            100                 105
```

<210> SEQ ID NO 84
<211> LENGTH: 318
<212> TYPE: DNA
<213> ORGANISM: Artificial Sequence
<220> FEATURE:
<223> OTHER INFORMATION: Synthesized

<400> SEQUENCE: 84

```
gacgtgcagc tgacccagtc tccttccagc ctgtccgcca gcgtgggcga tagagtgacc       60
atcacatgct ccgcttcttc cagcgtgggc tacatgcact ggtatcagca gaagcccggc      120
aaggccccta gaggctgat ctacgacaca tctaagctgg cttccggagt gccaagccgg       180
ttctctggct ccggcagcgg aaccgactac accctgacaa tctcttccct gcagccagag      240
gatttcgcca catattttg tcagcagtgg agctctatcc ccctgacctt tggccagggc       300
acacgcctgg agatcaag                                                    318
```

<210> SEQ ID NO 85
<211> LENGTH: 117
<212> TYPE: PRT
<213> ORGANISM: Artificial Sequence
<220> FEATURE:
<223> OTHER INFORMATION: Synthesized

<400> SEQUENCE: 85

```
Gln Val Gln Leu Val Gln Ser Gly Ala Glu Val Lys Lys Pro Gly Ala
1               5                   10                  15

Ser Val Lys Val Ser Cys Lys Ser Ser Gly Tyr Thr Phe Thr Asn Tyr
            20                  25                  30

Trp Met His Trp Val Arg Gln Ala Pro Gly Gln Gly Leu Glu Trp Ile
        35                  40                  45

Gly Glu Ile Tyr Pro Asn Asn Gly Arg Val Asn Tyr Asn Glu Lys Phe
```

```
        50              55              60

Lys Asn Arg Ala Thr Leu Thr Val Asp Ile Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Arg Tyr Asp Pro Met Glu Asp Trp Gly Gln Gly Thr Thr
                100                 105                 110

Val Thr Val Ser Ser
        115
```

<210> SEQ ID NO 86
<211> LENGTH: 351
<212> TYPE: DNA
<213> ORGANISM: Artificial Sequence
<220> FEATURE:
<223> OTHER INFORMATION: Synthesized

<400> SEQUENCE: 86

```
caggtgcagc tggtgcagag cggagctgag gtgaagaagc caggagcttc cgtgaaggtg      60
agctgcaagt ccagcggcta caccttcaca aactattgga tgcactgggt gaggcaggct     120
ccaggacagg gactggagtg gatcggcgag atctacccta acaatggcag ggtgaactac     180
aacgagaagt ttaagaacag agccaccctg acagtggaca tcagcatctc taccgcttac     240
atggagctgt ctaggctgcg gtccgacgat acagccgtgt actattgtgc tagatctcgc     300 tatgaccccca tggaggattg gggccagggc accacagtga ccgtgtcttc c             351
```

<210> SEQ ID NO 87
<211> LENGTH: 106
<212> TYPE: PRT
<213> ORGANISM: Artificial Sequence
<220> FEATURE:
<223> OTHER INFORMATION: Synthesized

<400> SEQUENCE: 87

```
Asp Val Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Gly Tyr Met
                20                  25                  30

His Trp Tyr Gln Gln Lys Pro Gly Lys Ala Pro Lys Arg Trp Ile Tyr
            35                  40                  45

Asp Thr Ser Lys Leu Ala Ser Gly Val Pro Ser Arg Phe Ser Gly Ser
        50                  55                  60

Gly Ser Gly Thr Asp Tyr Thr Leu Thr Ile Ser Ser Leu Gln Pro Glu
65                  70                  75                  80

Asp Phe Ala Thr Tyr Phe Cys Gln Gln Trp Ser Ser Ile Pro Leu Thr
                85                  90                  95

Phe Gly Gln Gly Thr Arg Leu Glu Ile Lys
            100                 105
```

<210> SEQ ID NO 88
<211> LENGTH: 318
<212> TYPE: DNA
<213> ORGANISM: Artificial Sequence
<220> FEATURE:
<223> OTHER INFORMATION: Synthesized

<400> SEQUENCE: 88

```
gacgtgcagc tgacccagtc tccttccagc ctgtccgcca gcgtgggcga tagagtgacc      60
```

```
atcacatgct ccgcttcttc cagcgtgggc tacatgcact ggtatcagca gaagcccggc        120
aaggccccta agaggtggat ctacgacaca tctaagctgg cttccggagt gccaagccgg        180
ttctctggct ccggcagcgg aaccgactac accctgacaa tctcttccct gcagccagag        240
gatttcgcca catattttg tcagcagtgg agctctatcc ccctgacctt tggccagggc        300
acacgcctgg agatcaag                                                      318
```

```
<210> SEQ ID NO 89
<211> LENGTH: 117
<212> TYPE: PRT
<213> ORGANISM: Artificial Sequence
<220> FEATURE:
<223> OTHER INFORMATION: Synthesized

<400> SEQUENCE: 89

Gln Val Gln Leu Val Gln Ser Gly Ala Glu Val Lys Lys Pro Gly Ser
1               5                   10                  15

Ser Val Lys Val Ser Cys Lys Ser Ser Gly Tyr Thr Phe Thr Asn Tyr
            20                  25                  30

Trp Met His Trp Val Arg Gln Ala Pro Gly Gln Gly Leu Glu Trp Ile
        35                  40                  45

Gly Glu Ile Tyr Pro Asn Asn Gly Arg Val Asn Tyr Asn Glu Lys Phe
    50                  55                  60

Lys Asn Arg Ala Thr Leu Thr Val Asp Ile Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Tyr Asp Pro Met Glu Asp Trp Gly Gln Gly Thr Thr
            100                 105                 110

Val Thr Val Ser Ser
        115
```

```
<210> SEQ ID NO 90
<211> LENGTH: 351
<212> TYPE: DNA
<213> ORGANISM: Artificial Sequence
<220> FEATURE:
<223> OTHER INFORMATION: Synthesized

<400> SEQUENCE: 90
caggtgcagc tggtgcagtc cggagctgag gtgaagaagc caggctccag cgtgaaggtg        60
agctgcaagt cttccggcta caccttcaca aactattgga tgcactgggt gaggcaggct       120
ccaggacagg gactggagtg gatcggcgag atctacccta caatggcag agtgaactac        180 aacgagaagt ttaagaaccg cgccaccctg acagtggaca tctctacctc cacagcttac       240
atggagctga gctctctgag aagcgaggat accgccgtgt actattgtgc taggtctcgg       300
tatgacccca tggaggattg gggccagggc accacagtga cagtgtccag c                351
```

```
<210> SEQ ID NO 91
<211> LENGTH: 106
<212> TYPE: PRT
<213> ORGANISM: Artificial Sequence
<220> FEATURE:
<223> OTHER INFORMATION: Synthesized

<400> SEQUENCE: 91

Gln Val Gln Leu Thr Gln Ser Pro Ser Ser Leu Ser Ala Ser Val Gly
1               5                   10                  15
```

```
Asp Arg Val Thr Ile Thr Cys Ser Ala Ser Ser Ser Val Gly Tyr Met
            20              25              30

His Trp Tyr Gln Gln Lys Pro Gly Lys Ala Pro Lys Arg Leu Ile Tyr
        35              40              45

Asp Thr Ser Lys Leu Ala Ser Gly Val Pro Ser Arg Phe Ser Gly Ser
    50              55              60

Gly Ser Gly Thr Asp Tyr Thr Leu Thr Ile Ser Ser Leu Gln Pro Glu
65              70              75              80

Asp Phe Ala Thr Tyr Phe Cys Gln Gln Trp Ser Ser Ile Pro Leu Thr
                85              90              95

Phe Gly Gln Gly Thr Arg Leu Glu Ile Lys
            100             105
```

<210> SEQ ID NO 92
<211> LENGTH: 318
<212> TYPE: DNA
<213> ORGANISM: Artificial Sequence
<220> FEATURE:
<223> OTHER INFORMATION: Synthesized

<400> SEQUENCE: 92

```
caggtgcagc tgacccagtc tccttccagc ctgtccgcca gcgtgggcga cagagtgacc      60
atcacatgct ccgcttcttc cagcgtgggc tacatgcact ggtatcagca gaagcccggc     120 aaggcccccta agaggctgat ctacgataca tctaagctgg cttccggagt gccaagccgg     180
ttctctggct ccggcagcgg aaccgactac accctgacaa tctcttccct gcagccagag     240
gatttcgcca catatttttg tcagcagtgg agctctatcc ccctgacctt tggccagggc     300
acacgcctgg agatcaag                                                   318
```

<210> SEQ ID NO 93
<211> LENGTH: 106
<212> TYPE: PRT
<213> ORGANISM: Artificial Sequence
<220> FEATURE:
<223> OTHER INFORMATION: Synthesized

<400> SEQUENCE: 93

```
Gln Val Gln Leu Thr Gln Ser Pro Ser Ser Leu Ser Ala Ser Val Gly
1               5               10              15

Asp Arg Val Thr Ile Thr Cys Ser Ala Ser Ser Ser Val Gly Tyr Met
            20              25              30

His Trp Tyr Gln Gln Lys Pro Gly Lys Ala Pro Lys Arg Trp Ile Tyr
        35              40              45

Asp Thr Ser Lys Leu Ala Ser Gly Val Pro Ser Arg Phe Ser Gly Ser
    50              55              60

Gly Ser Gly Thr Asp Tyr Thr Leu Thr Ile Ser Ser Leu Gln Pro Glu
65              70              75              80

Asp Phe Ala Thr Tyr Phe Cys Gln Gln Trp Ser Ser Ile Pro Leu Thr
                85              90              95

Phe Gly Gln Gly Thr Arg Leu Glu Ile Lys
            100             105
```

<210> SEQ ID NO 94
<211> LENGTH: 318
<212> TYPE: DNA
<213> ORGANISM: Artificial Sequence
<220> FEATURE:
<223> OTHER INFORMATION: Synthesized

<400> SEQUENCE: 94

```
caggtgcagc tgacccagtc tccttccagc ctgtccgcca gcgtgggcga cagagtgacc      60
atcacatgct ccgcttcttc cagcgtgggc tacatgcact ggtatcagca gaagcccggc     120
aaggccccta gaggtggat ctacgataca tctaagctgg cttccggagt gccaagccgg     180
ttctctggct ccggcagcgg aaccgactac accctgacaa tctcttccct gcagccagag     240
gatttcgcca catattttg tcagcagtgg agctctatcc ccctgacctt tggccagggc     300
acacgcctgg agatcaag                                                  318
```

<210> SEQ ID NO 95
<211> LENGTH: 106
<212> TYPE: PRT
<213> ORGANISM: Artificial Sequence
<220> FEATURE:
<223> OTHER INFORMATION: Synthesized

<400> SEQUENCE: 95

```
Glu Val Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Gly Tyr Met
            20                  25                  30

His Trp Tyr Gln Gln Lys Pro Gly Gln Ala Pro Arg Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Ala Ala Val Tyr Phe Cys Gln Gln Trp Ser Ser Ile Pro Leu Thr
                85                  90                  95

Phe Gly Gln Gly Thr Arg Leu Glu Ile Lys
            100                 105
```

<210> SEQ ID NO 96
<211> LENGTH: 318
<212> TYPE: DNA
<213> ORGANISM: Artificial Sequence
<220> FEATURE:
<223> OTHER INFORMATION: Synthesized

<400> SEQUENCE: 96

```
gaggtggtgc tgacccagtc cccagccaca ctgagcctgt ctccaggaga gagagccacc      60
ctgtcctgct ccgcctccag ctctgtgggc tacatgcact ggtatcagca gaagccagga     120
caggctccta ggcggtggat ctacgacacc tctaagctgg cttccggagt gccagctcgc     180
ttctctggct ccggcagcgg cacagactac accctgacaa tctccagcct ggagcctgag     240
gatgccgccg tgtacttctg tcagcagtgg tcttccatcc cactgacctt tggccagggc     300
acaaggctgg agatcaag                                                  318
```

<210> SEQ ID NO 97
<211> LENGTH: 117
<212> TYPE: PRT
<213> ORGANISM: Artificial Sequence
<220> FEATURE:
<223> OTHER INFORMATION: Synthesized

<400> SEQUENCE: 97

```
Gln Val Gln Leu Val Gln Ser Gly Ala Glu Val Lys Lys Pro Gly Ala
1               5                   10                  15
```

-continued

```
Ser Val Lys Val Ser Cys Lys Ser Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Glu Ile Tyr Pro Asn Ser Gly Arg Val Asn Tyr Asn Glu Lys Phe
    50                  55                  60

Lys Asn Arg Val Thr Met Thr Val Asp Ile Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Arg Tyr Asp Pro Met Glu Asp Trp Gly Gln Gly Thr Thr
                100                 105                 110

Val Thr Val Ser Ser
        115
```

```
<210> SEQ ID NO 98
<211> LENGTH: 351
<212> TYPE: DNA
<213> ORGANISM: Artificial Sequence
<220> FEATURE:
<223> OTHER INFORMATION: Synthesized

<400> SEQUENCE: 98
caggtgcagc tggtgcagtc cggcgccgag gtgaagaagc ccggcgcttc tgtgaaggtg      60
agctgcaaga gctccggcta cacctttacc aattattgga tgcactgggt gaggcaggct     120
cccggccagg gactggagtg gatgggcgag atatatccca atagcggccg ggtgaattat     180
aatgagaagt ttaagaatcg ggtgaccatg accgtggata tcagcatctc caccgcctac     240
atggagctga gcaggctgag gagcgatgac accgctgtgt actactgcgc taggtccagg     300
tatgacccca tggaggattg gggccagggc accaccgtga ccgtgagcag c              351
```

```
<210> SEQ ID NO 99
<211> LENGTH: 117
<212> TYPE: PRT
<213> ORGANISM: Artificial Sequence
<220> FEATURE:
<223> OTHER INFORMATION: Synthesized

<400> SEQUENCE: 99

Gln Val Gln Leu Val Gln Ser Gly Ala Glu Val Lys Lys Pro Gly Ala
1               5                   10                  15

Ser Val Lys Val Ser Cys Lys Ser Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Glu Ile Tyr Pro Asn Gln Gly Arg Val Asn Tyr Asn Glu Lys Phe
    50                  55                  60

Lys Asn Arg Val Thr Met Thr Val Asp Ile Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Arg Tyr Asp Pro Met Glu Asp Trp Gly Gln Gly Thr Thr
                100                 105                 110

Val Thr Val Ser Ser
        115
```

-continued

```
<210> SEQ ID NO 100
<211> LENGTH: 351
<212> TYPE: DNA
<213> ORGANISM: Artificial Sequence
<220> FEATURE:
<223> OTHER INFORMATION: Synthesized

<400> SEQUENCE: 100
caggtgcagc tggtgcagag cggcgccgag gtgaagaagc ccggcgcttc cgtgaaggtg      60
tcctgtaagt ccagcggcta taccttcacc aactattgga tgcactgggt gaggcaggcc     120
cctggccagg gactggagtg gatgggcgag atatatccta accagggccg ggtgaattat     180
aacgagaagt tcaagaatag ggtgaccatg accgtggaca tctccatcag caccgcttac     240
atggagctgt ccaggctgcg gagcgacgat accgccgtgt actactgtgc caggtcccgg     300
tatgatccca tggaggactg gggccagggc accaccgtga ccgtgagcag c             351

<210> SEQ ID NO 101
<211> LENGTH: 117
<212> TYPE: PRT
<213> ORGANISM: Artificial Sequence
<220> FEATURE:
<223> OTHER INFORMATION: Synthesized

<400> SEQUENCE: 101

Gln Val Gln Leu Val Gln Ser Gly Ala Glu Val Lys Lys Pro Gly Ala
1               5                   10                  15

Ser Val Lys Val Ser Cys Lys Ser Ser Gly Tyr Thr Phe Thr Asn Tyr
                20                  25                  30

Trp Met His Trp Val Arg Gln Ala Pro Gly Gln Gly Leu Glu Trp Met
            35                  40                  45

Gly Glu Ile Tyr Pro Asn Asn Ala Arg Val Asn Tyr Asn Glu Lys Phe
        50                  55                  60

Lys Asn Arg Val Thr Met Thr Val Asp Ile Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Arg Tyr Asp Pro Met Glu Asp Trp Gly Gln Gly Thr Thr
            100                 105                 110

Val Thr Val Ser Ser
        115

<210> SEQ ID NO 102
<211> LENGTH: 351
<212> TYPE: DNA
<213> ORGANISM: Artificial Sequence
<220> FEATURE:
<223> OTHER INFORMATION: Synthesized

<400> SEQUENCE: 102
caggtgcagc tggtgcagtc cggcgccgag gtgaagaagc ccggcgcttc tgtgaaggtg      60
tcctgtaaga gcagcggcta cacctttaccaattattgga tgcactgggt gaggcaggcc     120
cccggccagg gattggagtg gatgggcgag atatatccta caaatgccag ggtgaactat     180
aatgagaagt ttaagaaccg ggtgaccatg accgtggaca tcagcatctc caccgcctat     240
atggagctga ccggctgcg gtccgacgac accgctgtgt actactgcgc ccggtcccgg     300
tatgatccta tggaggactg gggccagggc accaccgtga ccgtgagctc c             351
```